United States Patent
Khan et al.

(10) Patent No.: US 7,976,503 B2
(45) Date of Patent: Jul. 12, 2011

(54) HAEMOSTASIS DEVICE

(75) Inventors: Mazhar M. Khan, Belfast (IE); Aidan Mulloy, Dublin (IE); David Ronan, County Galway (IE); Gerard Brett, Galway (IE); Liam Mulloy, Galway (IE)

(73) Assignee: Vascular Solutions Zerusa Limited, Galway (IE)

( * ) Notice: Subject to any disclaimer, the term of this patent is extended or adjusted under 35 U.S.C. 154(b) by 2010 days.

(21) Appl. No.: 10/926,362

(22) Filed: Aug. 26, 2004

(65) Prior Publication Data
US 2005/0085789 A1 Apr. 21, 2005

Related U.S. Application Data

(60) Provisional application No. 60/497,570, filed on Aug. 26, 2003.

(51) Int. Cl.
*A61M 5/178* (2006.01)
(52) U.S. Cl. .................................. 604/167.06
(58) Field of Classification Search .................. None
See application file for complete search history.

(56) References Cited

U.S. PATENT DOCUMENTS

| | | | |
|---|---|---|---|
| 3,766,916 A | 10/1973 | Moorehead et al. | 128/214 |
| 3,977,400 A * | 8/1976 | Moorehead | 604/168.01 |
| 4,610,469 A | 9/1986 | Wolff-Mooij | 285/260 |
| 4,723,550 A | 2/1988 | Bales et al. | 128/344 |
| 4,935,010 A | 6/1990 | Cox et al. | 604/122 |
| 5,125,915 A | 6/1992 | Berry et al. | 604/283 |
| 5,195,980 A | 3/1993 | Catlin | 604/167 |
| 5,324,271 A | 6/1994 | Abiuso et al. | 604/167 |
| 5,338,314 A | 8/1994 | Ryan | 604/284 |
| 5,346,480 A * | 9/1994 | Hess et al. | 604/197 |
| 5,458,640 A | 10/1995 | Gerrone | 604/264 |
| 5,591,137 A | 1/1997 | Stevens | 604/256 |
| 5,693,025 A | 12/1997 | Stevens | 604/167 |
| 5,911,710 A | 6/1999 | Barry et al. | 604/249 |
| 5,921,968 A | 7/1999 | Lampropoulos | 604/246 |
| 6,206,851 B1 | 3/2001 | Prosl | 604/93 |
| 6,287,280 B1 | 9/2001 | Lampropoulos | 604/167 |
| 6,402,723 B1 | 6/2002 | Lampropoulos | 604/256 |
| 6,488,674 B2 | 12/2002 | Becker et al. | 604/533 |

(Continued)

FOREIGN PATENT DOCUMENTS
EP 0267584 A2 5/1988
(Continued)

OTHER PUBLICATIONS

Specification of U.S. Appl. No. 11/781,289, filed Jul. 23, 2007, Applicant David Ronan et al., entitled "A Device" (62 pages).

*Primary Examiner* — Nicholas D Lucchesi
*Assistant Examiner* — Pritesh Patel
(74) *Attorney, Agent, or Firm* — Finnegan, Henderson, Farabow, Garrett & Dunner LLP

(57) ABSTRACT

A haemostasis device (200) comprises a low pressure seal (206) and a high pressure seal (208). A tubular bayonet (201) is movable from a retracted configuration to an inserted configuration to move the low pressure seal (206) between a closed configuration and an open configuration. With the low pressure seal (206) in the open configuration, a guidewire (222) may be inserted through the low pressure seal (206), and with the low pressure seal (206) in the closed configuration, the guidewire (222) may be passed through the low pressure seal (206) while maintaining sealing around the guidewire (222). A collet (209) is movable in a radial direction to move the high pressure seal (208) between an open configuration and a sealing configuration. With the high pressure seal (208) in the sealing configuration, the guidewire (222) is locked in position.

64 Claims, 54 Drawing Sheets

U.S. PATENT DOCUMENTS

| | | |
|---|---|---|
| 6,520,939 B2 | 2/2003 | Lafontaine ............ 604/167 |
| 2001/0021825 A1* | 9/2001 | Becker et al. ......... 604/167.01 |
| 2002/0010425 A1 | 1/2002 | Guo et al. ............ 604/167 |
| 2002/0111585 A1 | 8/2002 | Lafontaine ............ 604/167 |
| 2003/0116731 A1* | 6/2003 | Hartley ............... 251/7 |

FOREIGN PATENT DOCUMENTS

| | | |
|---|---|---|
| EP | 0426407 A2 | 5/1991 |
| EP | 0875262 B1 | 1/2002 |
| WO | WO03/022351 | 3/2003 |
| WO | WO03/077982 | 9/2003 |

* cited by examiner

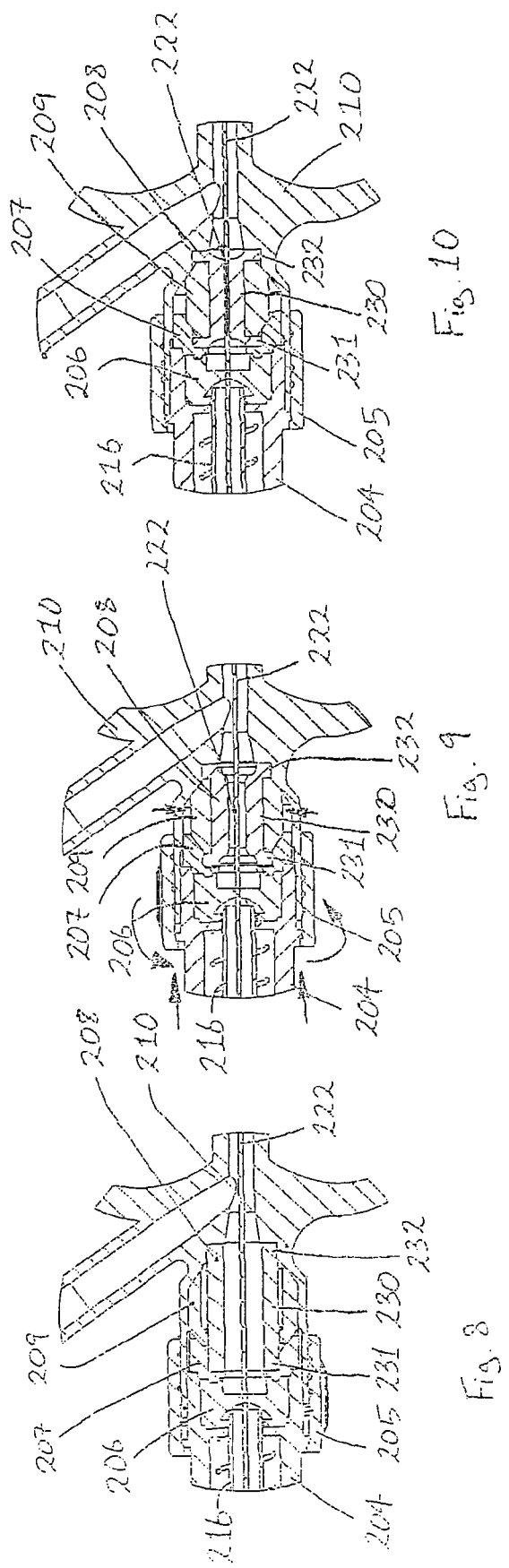

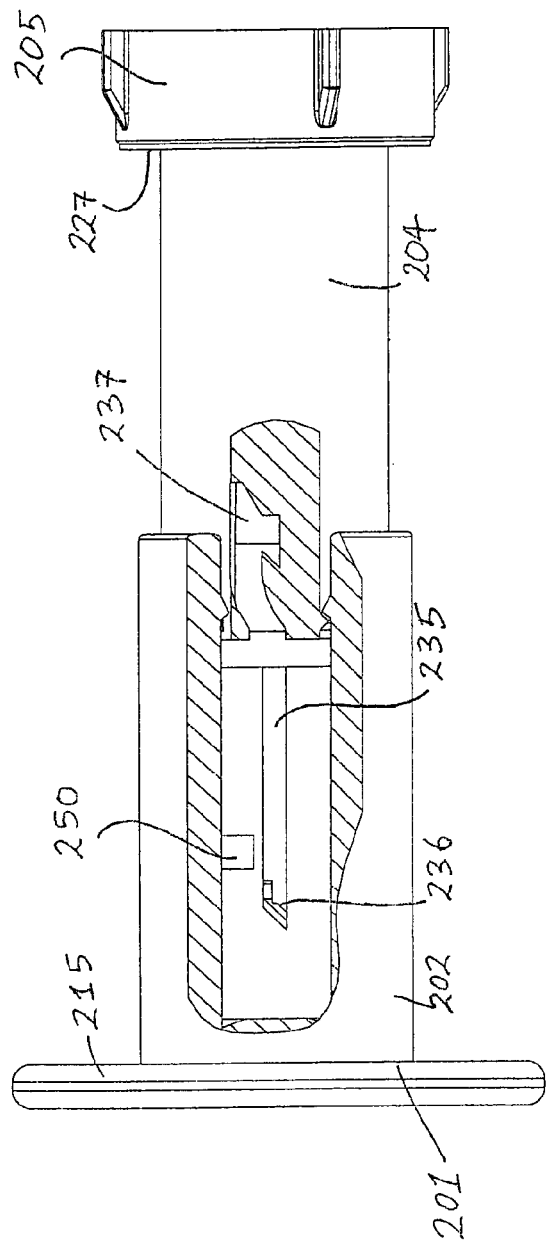
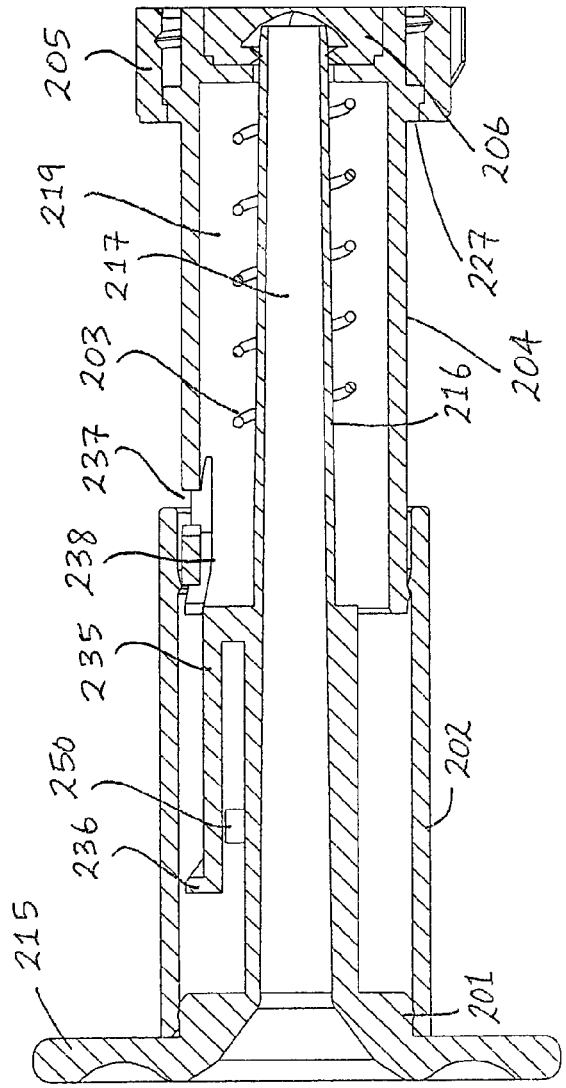
Fig. 15
Fig. 14

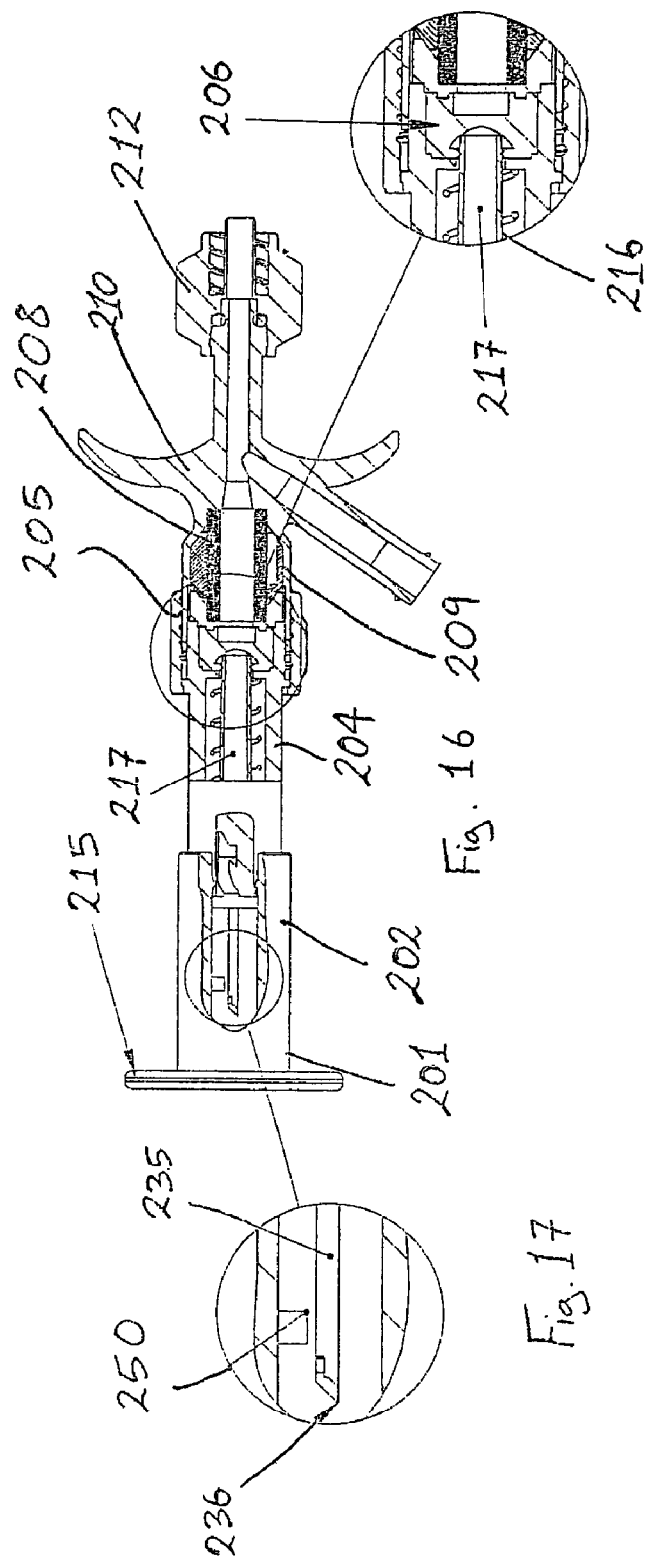

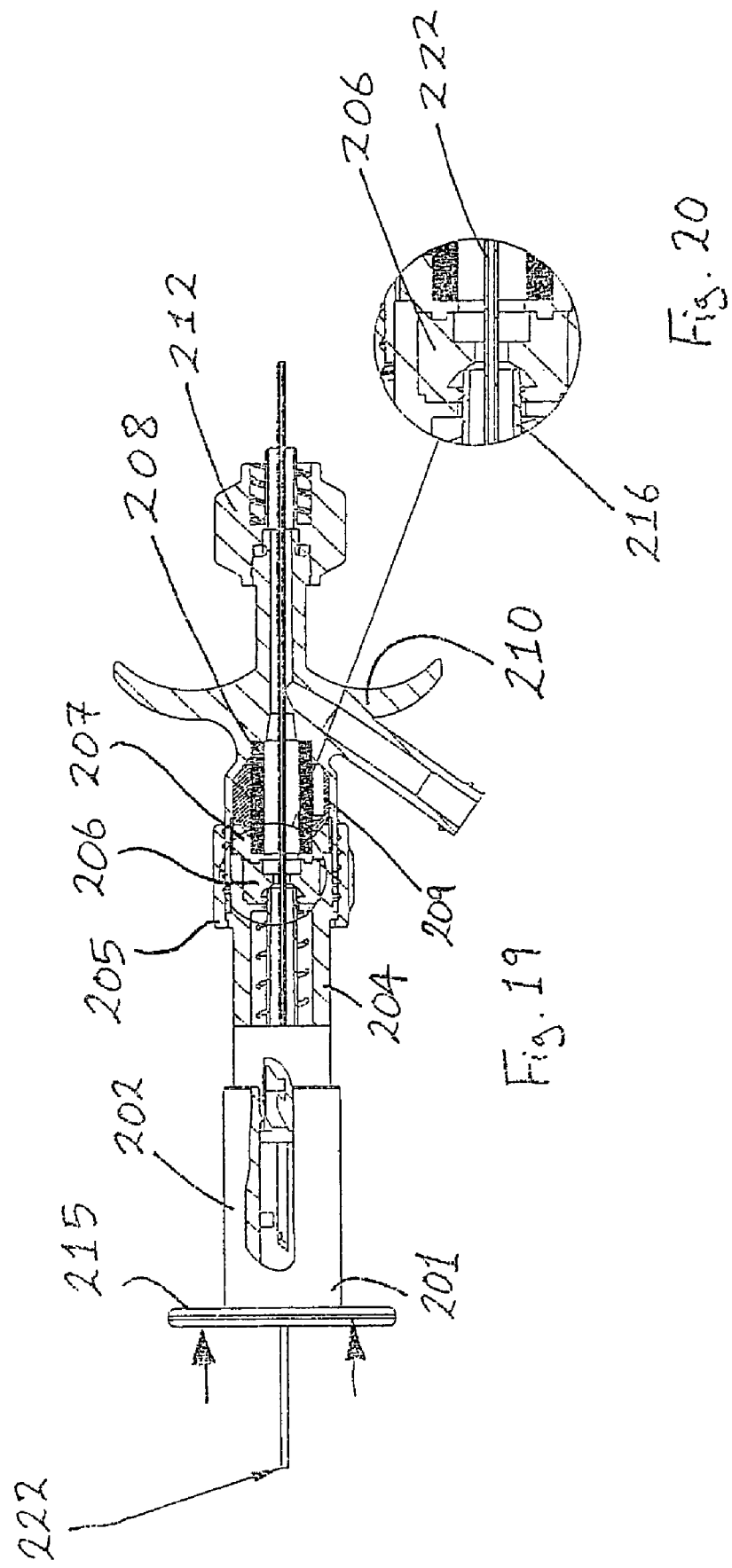

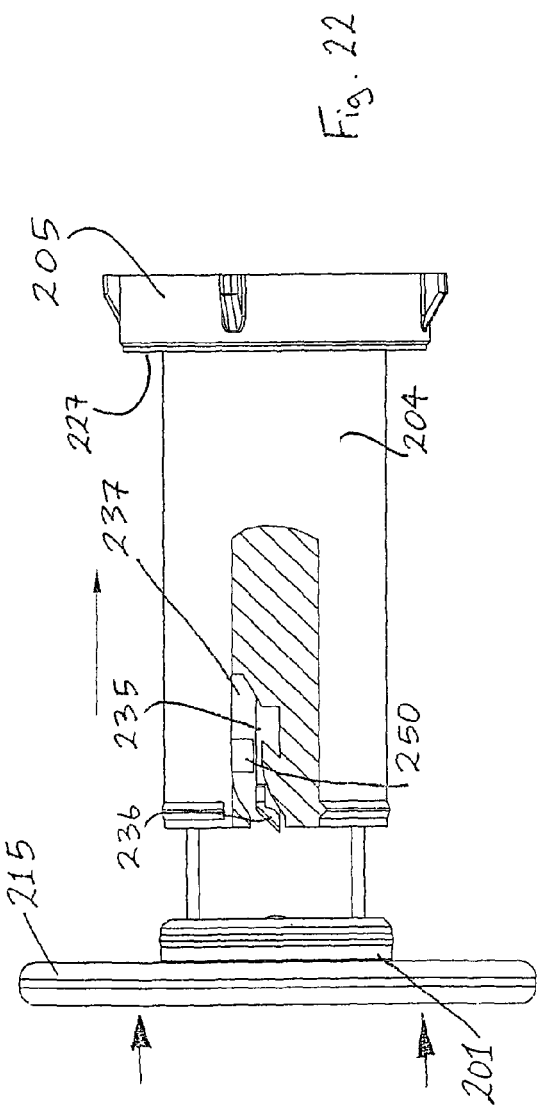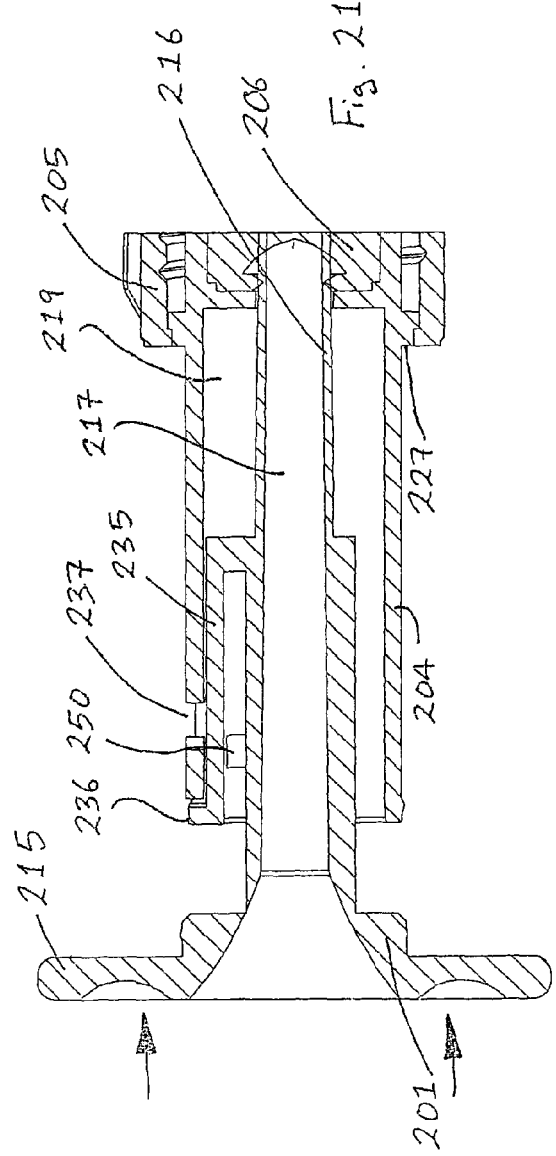

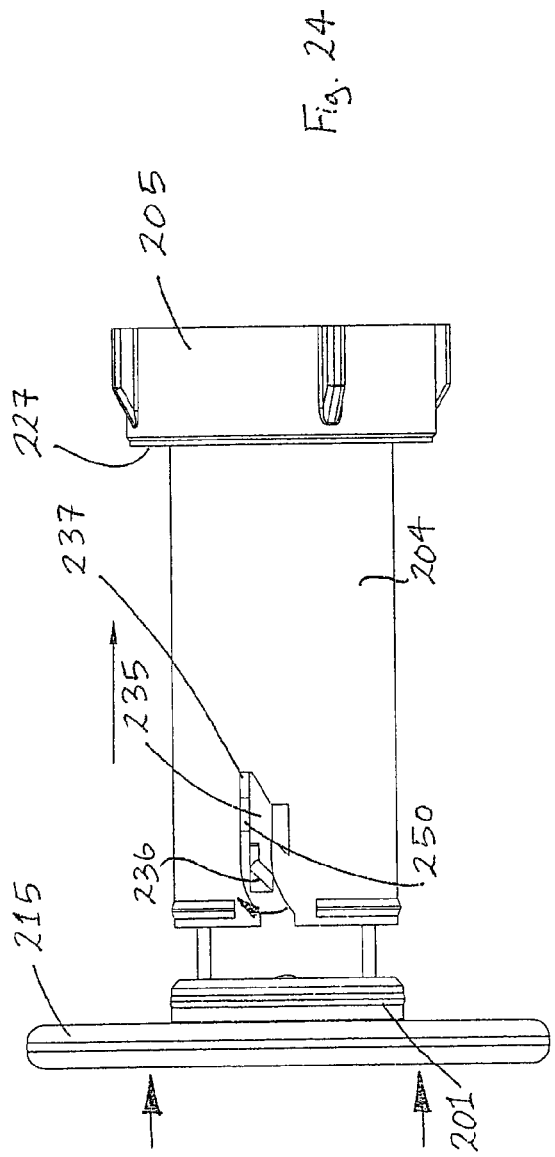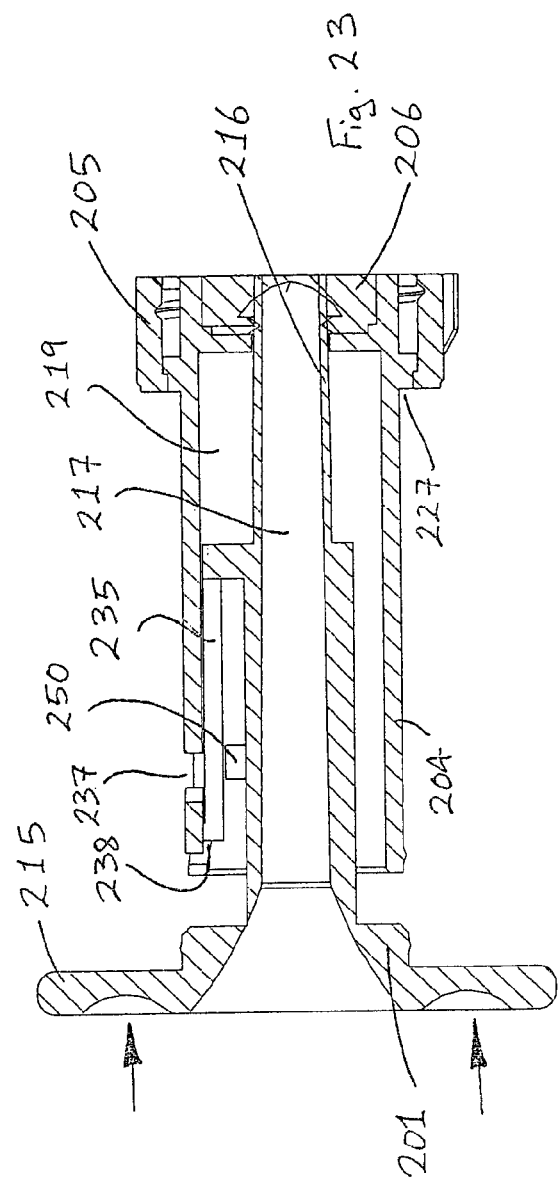

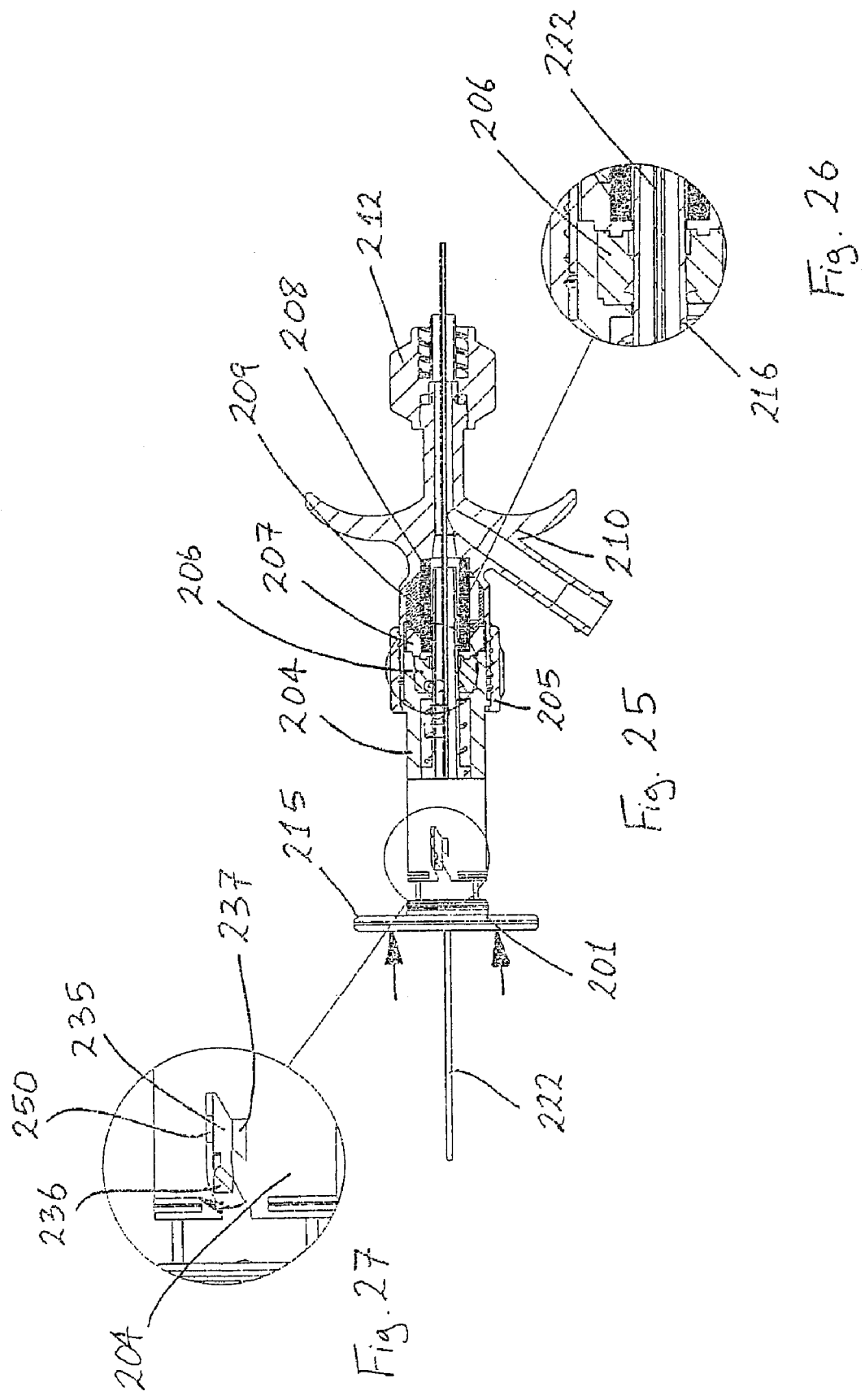

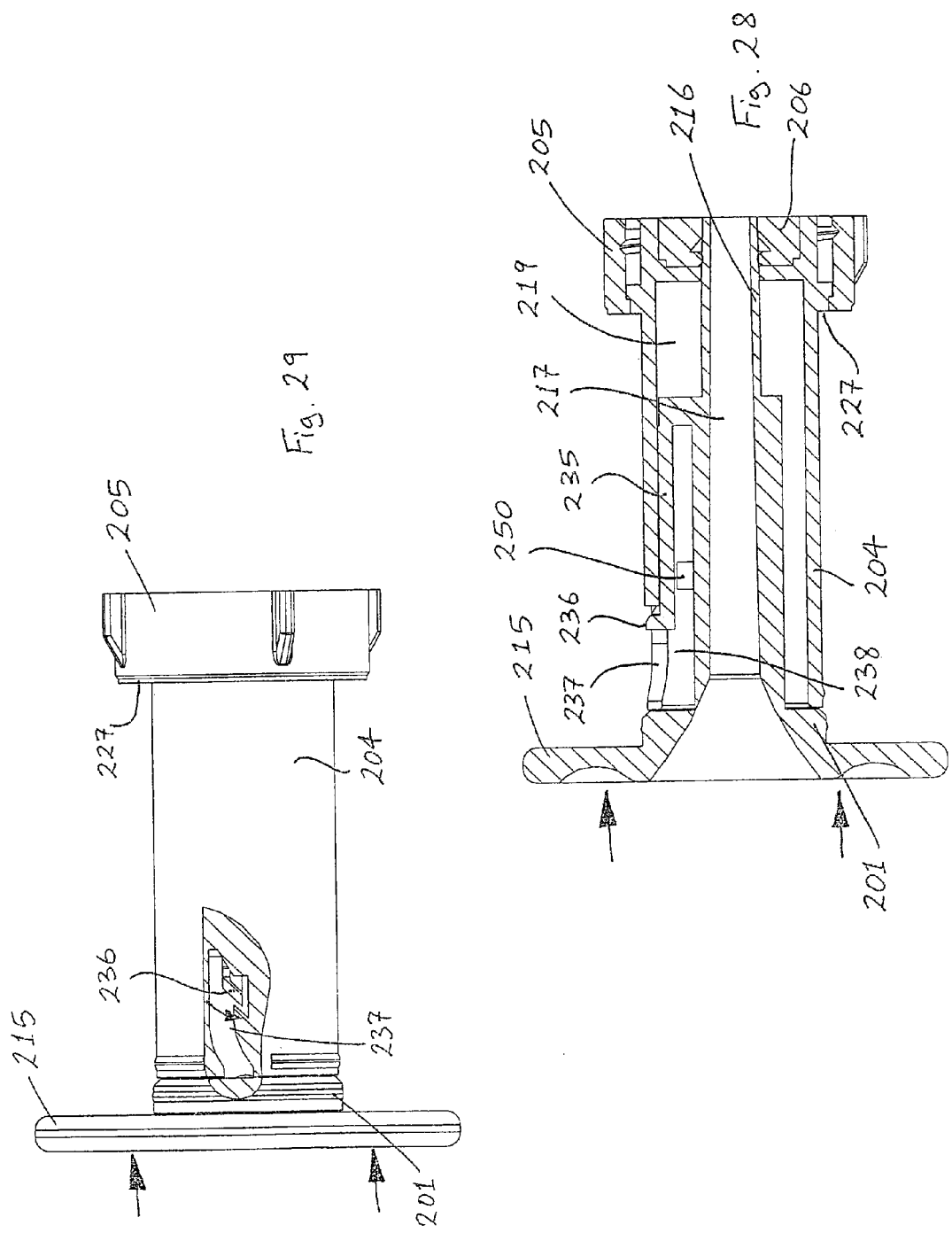

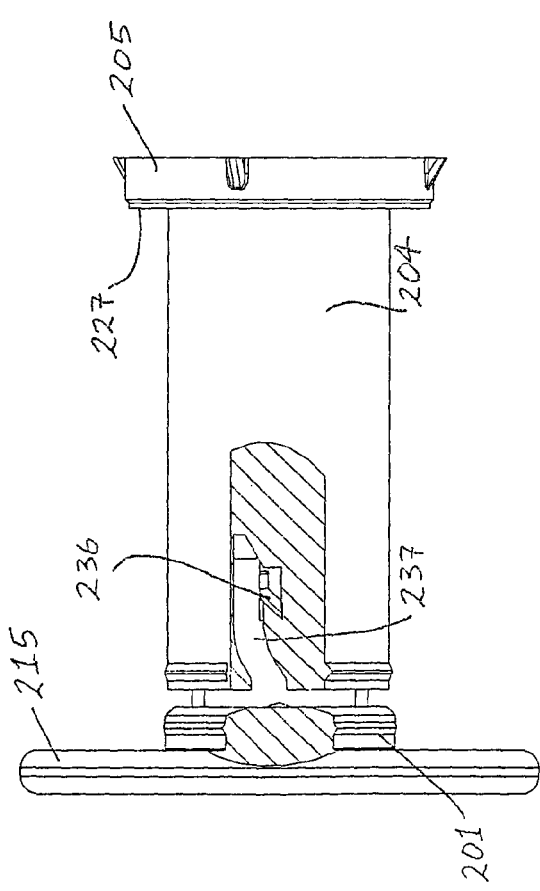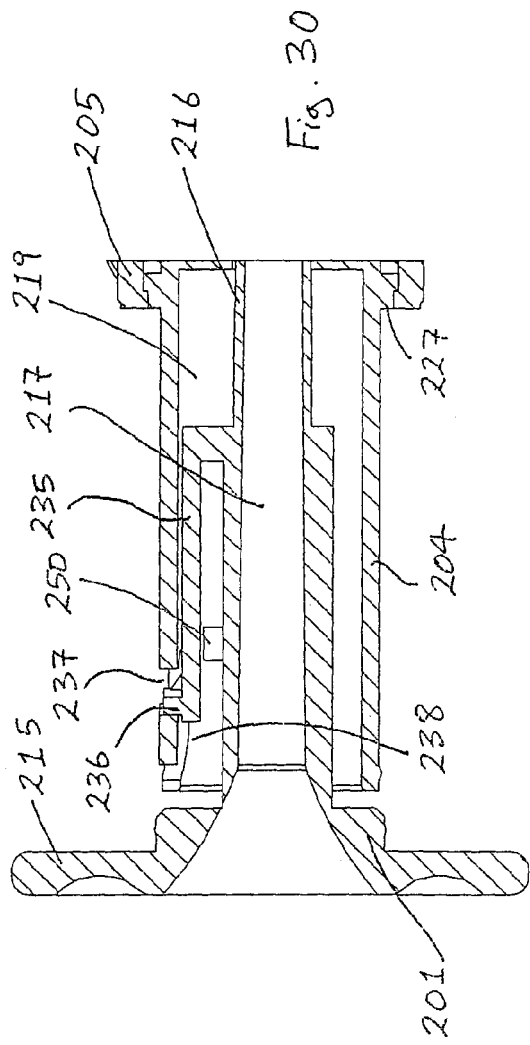

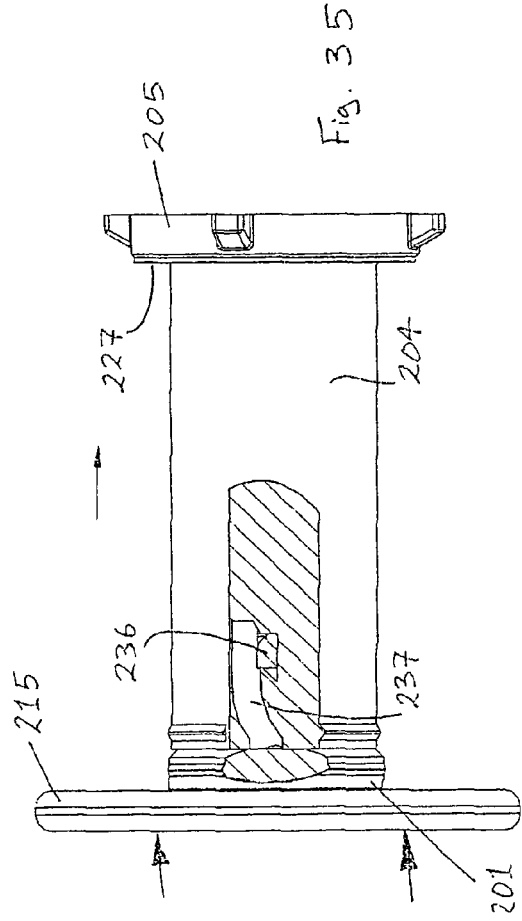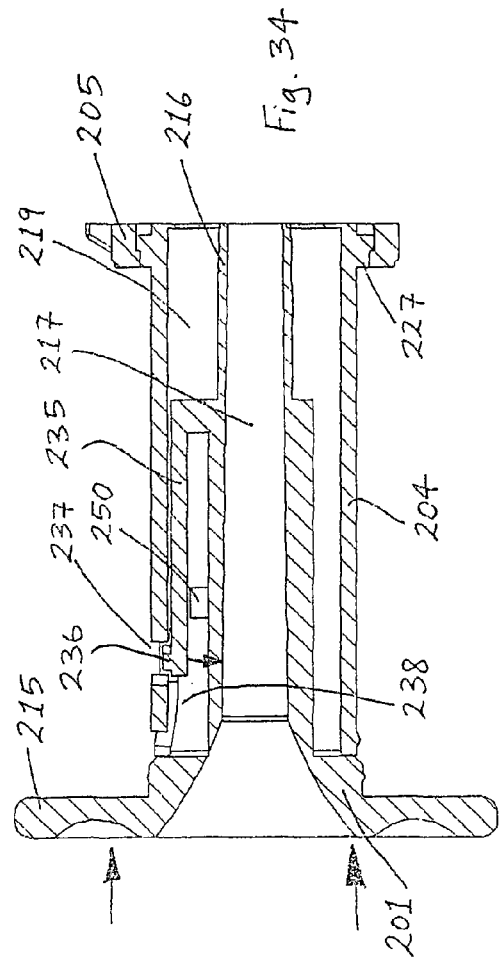

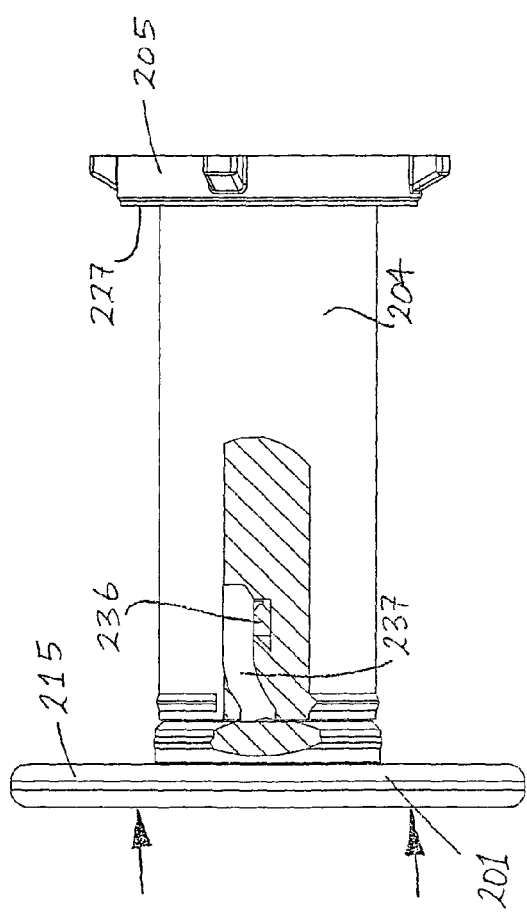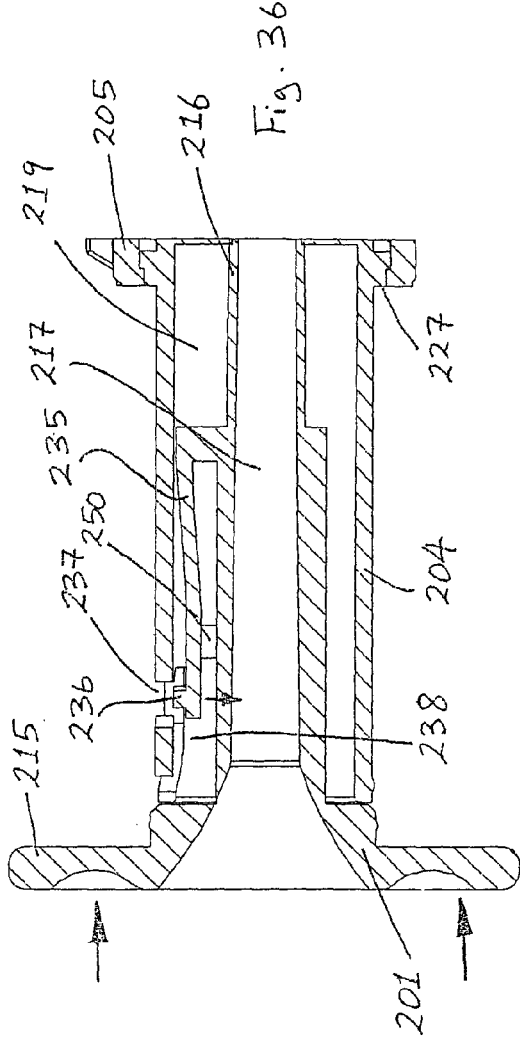

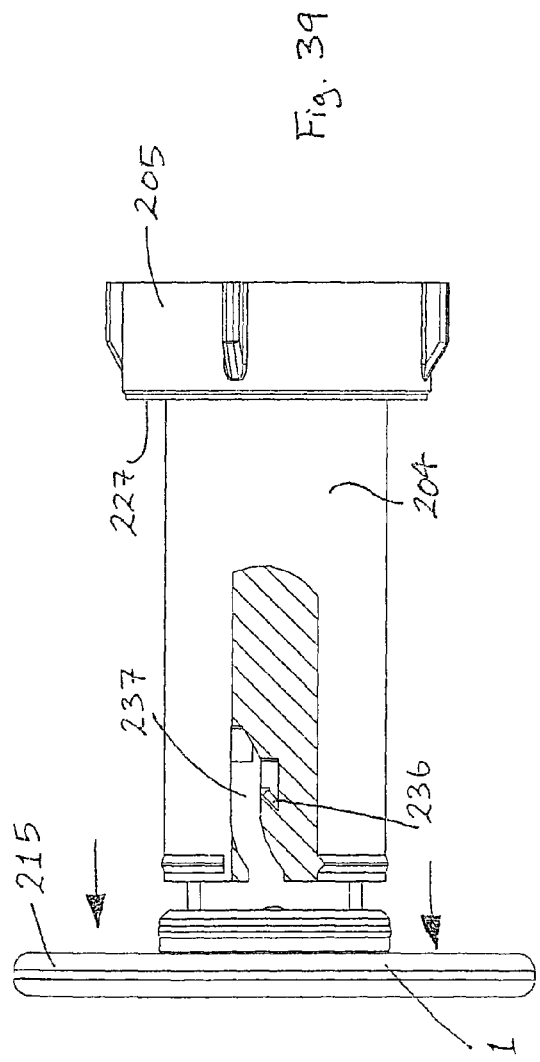
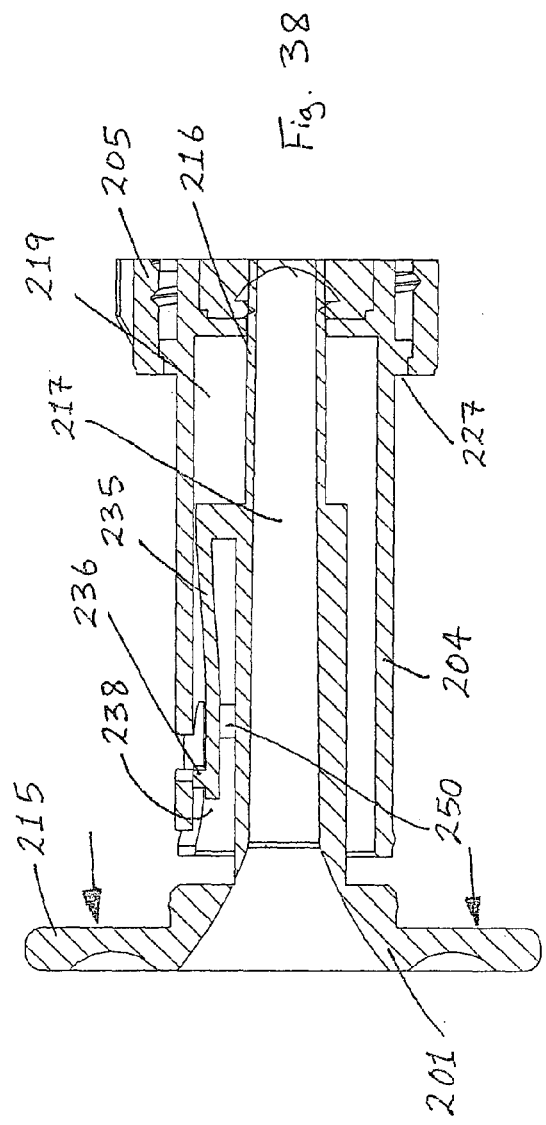

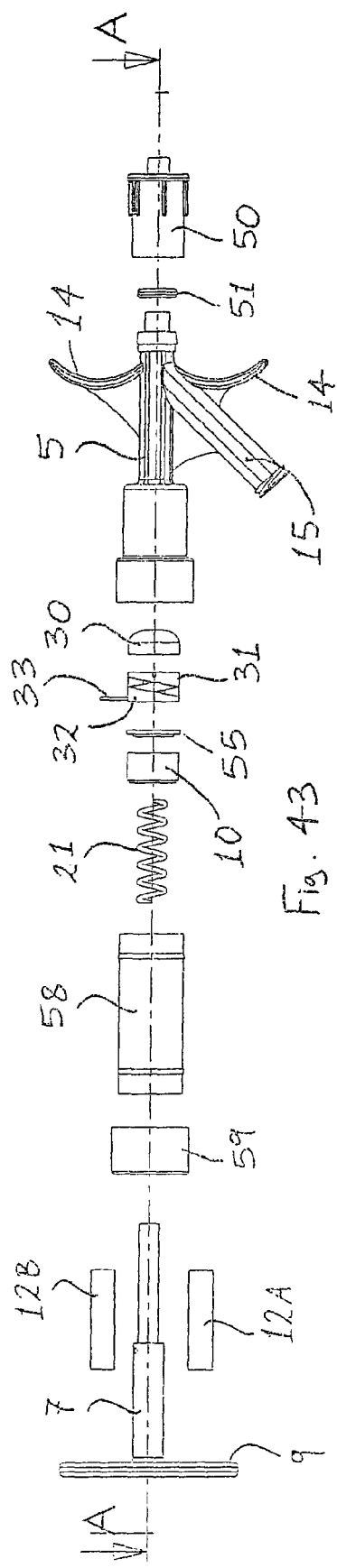
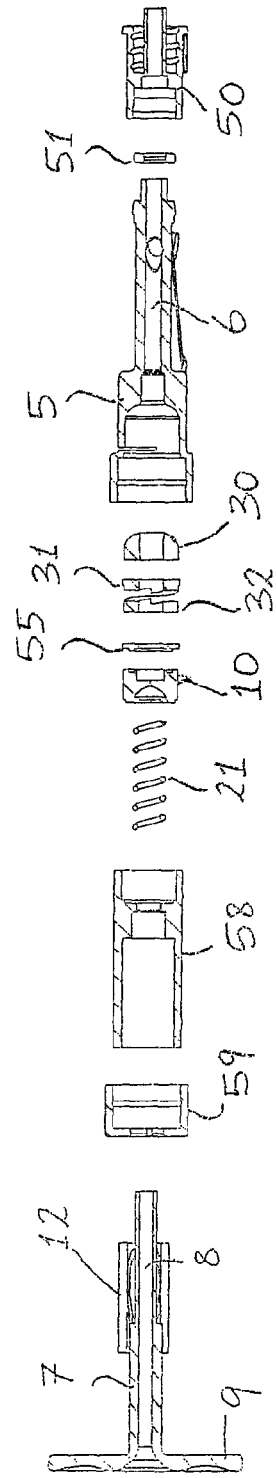
Fig. 43
Fig. 44

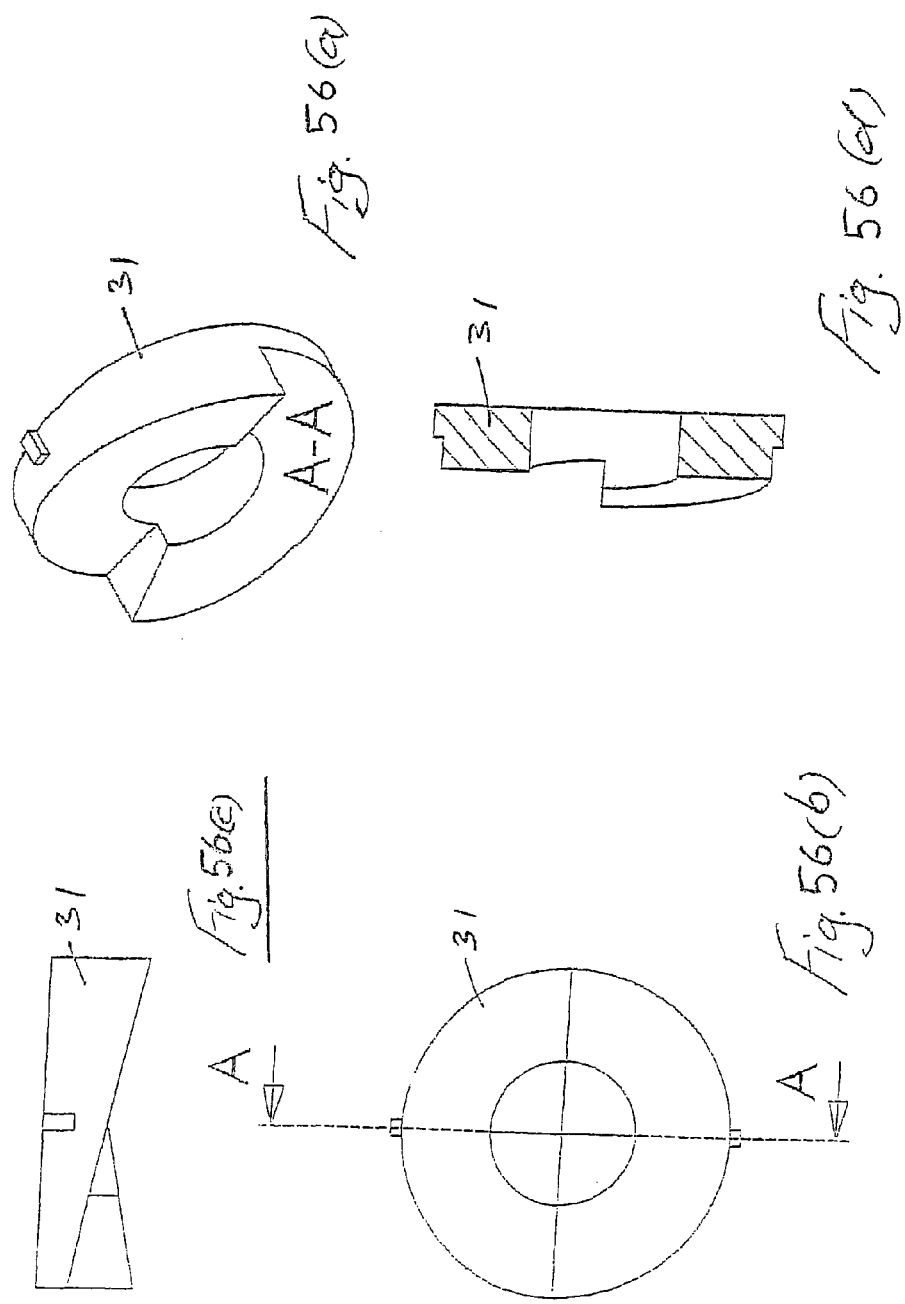

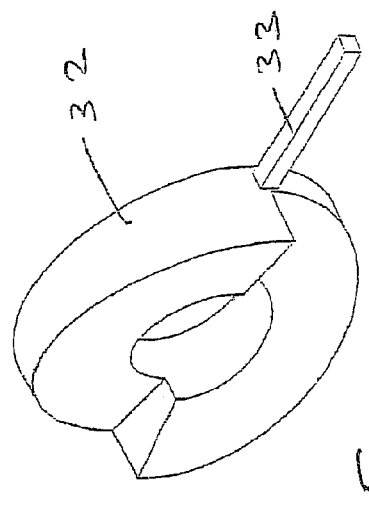
Fig. 57(a)
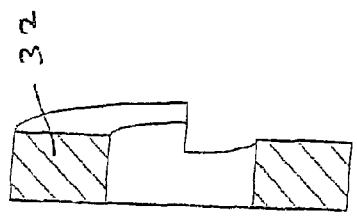
Fig. 57(d) B-B
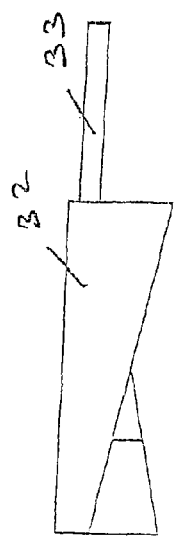
Fig. 57(c)
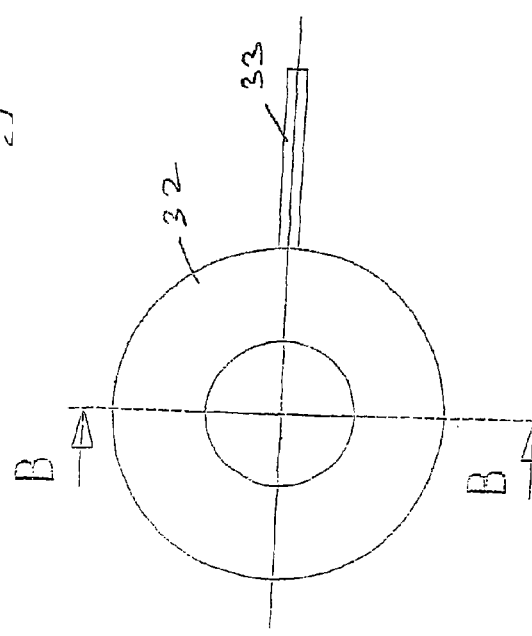
Fig. 57(b)

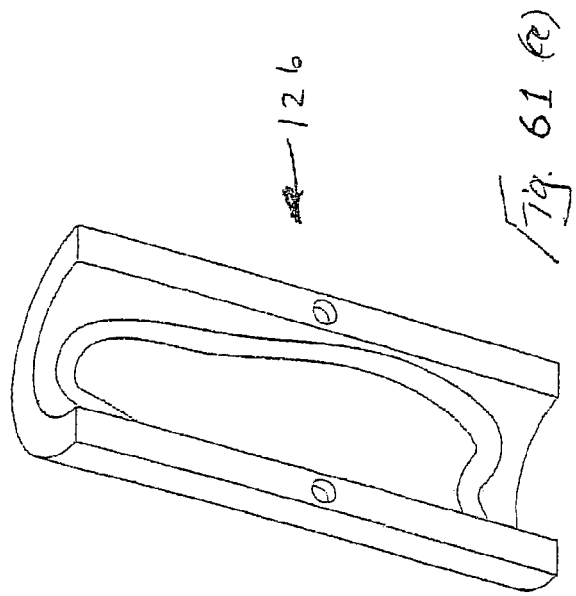
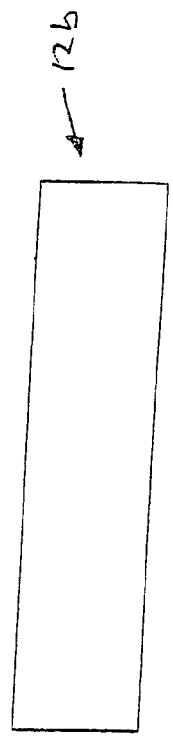
Fig. 61(a)
Fig. 61(d)
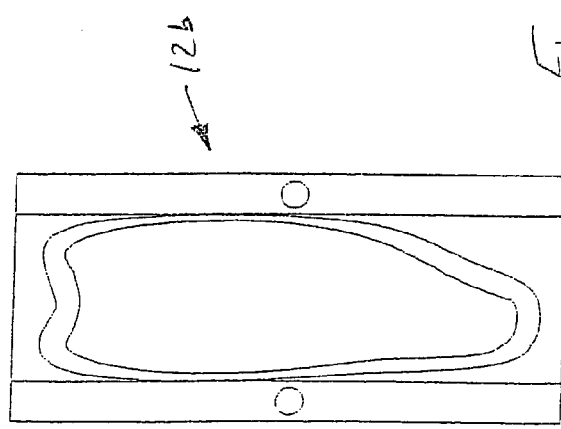
Fig. 61(b)
Fig. 61(c)

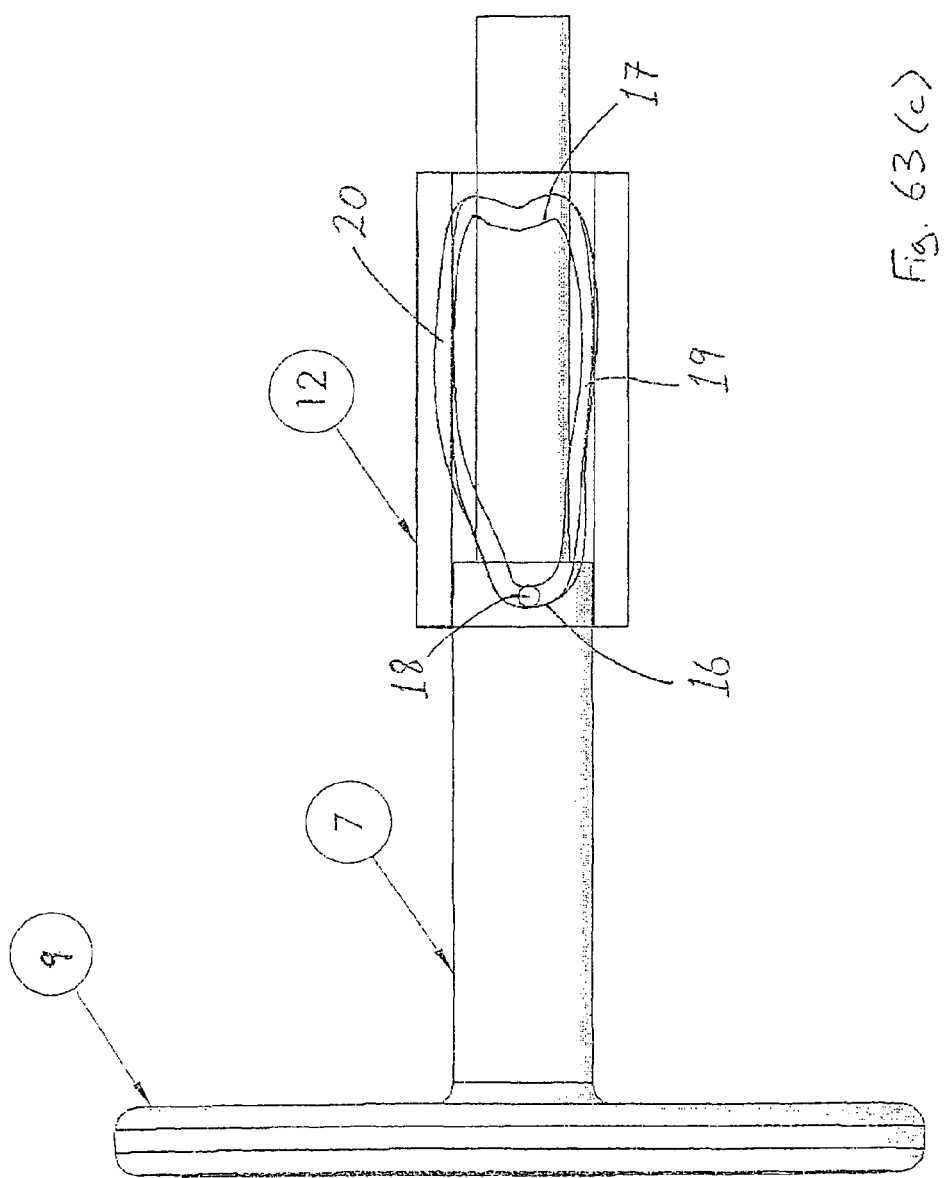

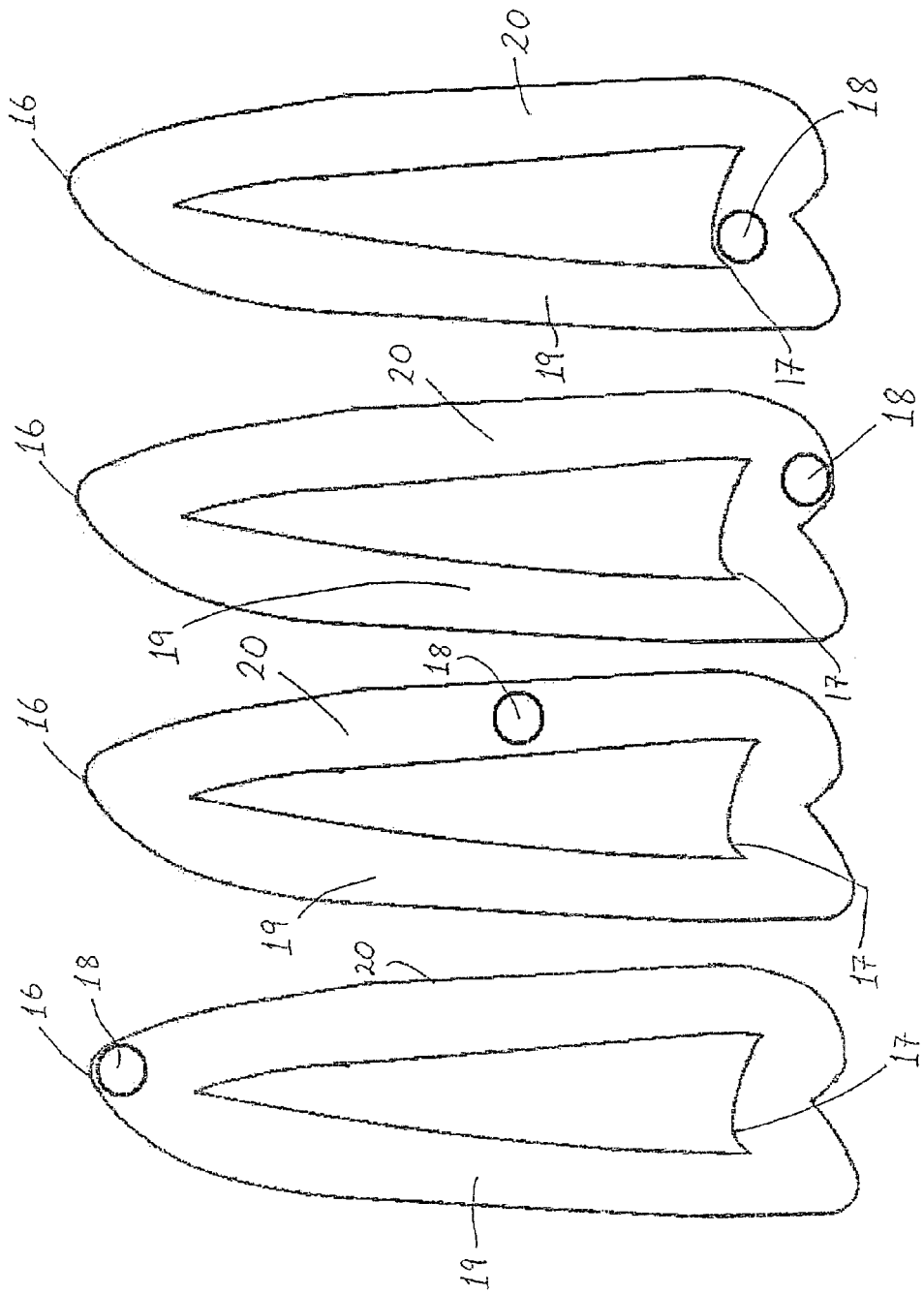

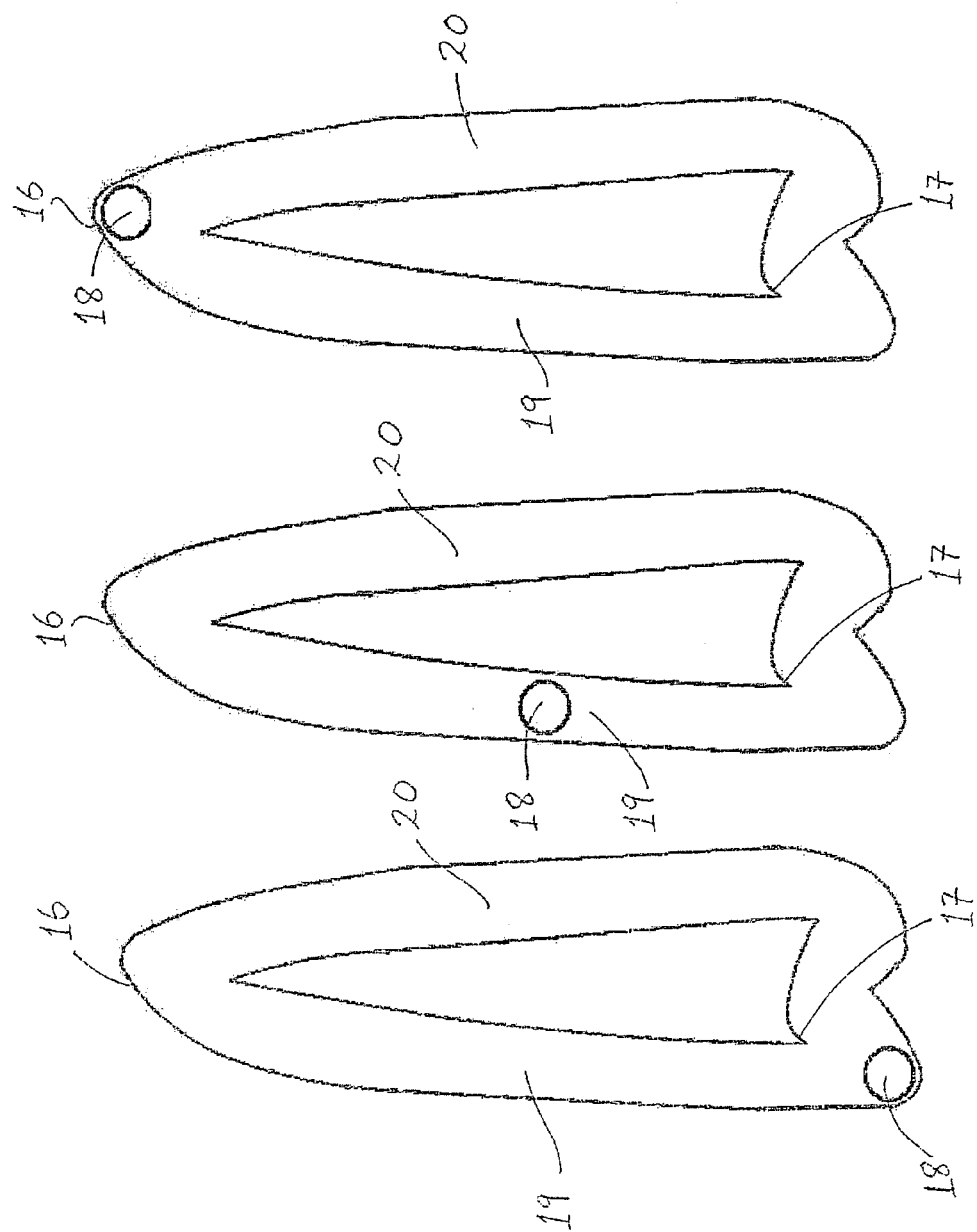

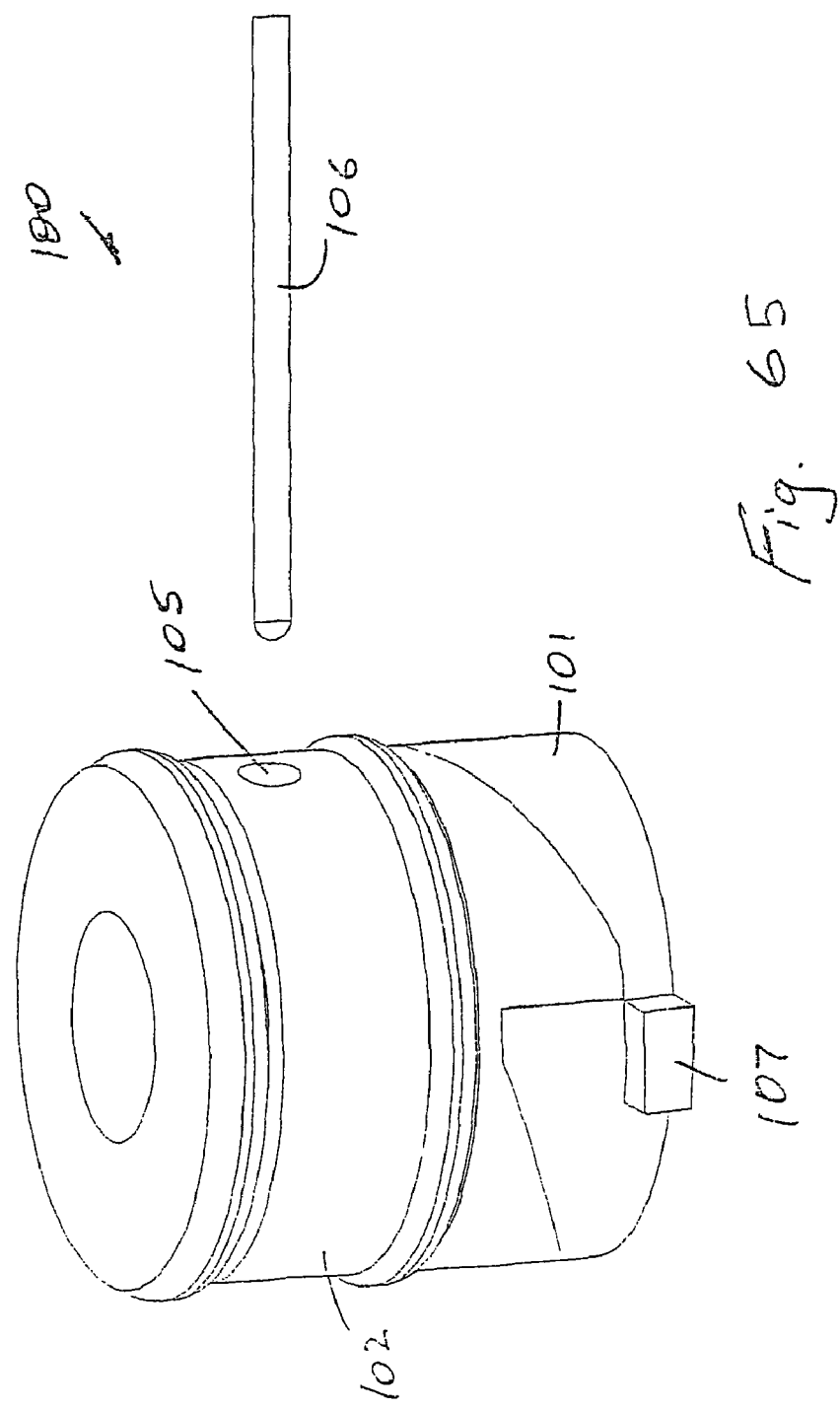

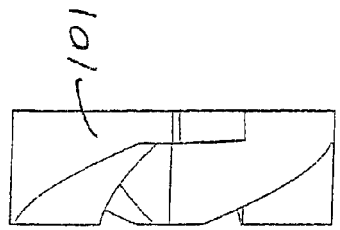
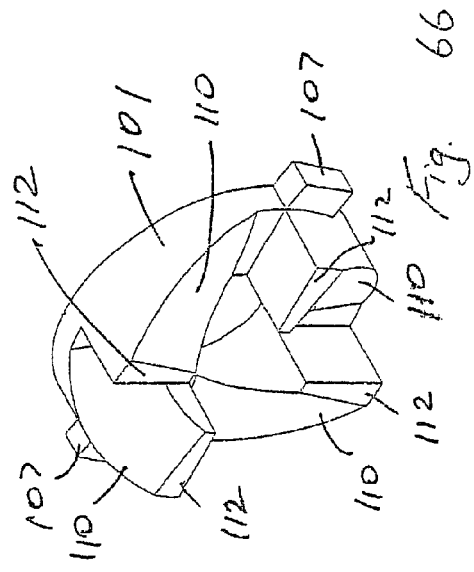
Fig. 67
Fig. 66
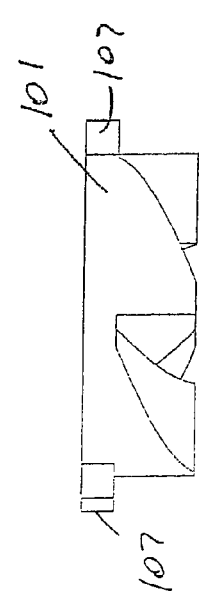
Fig. 68
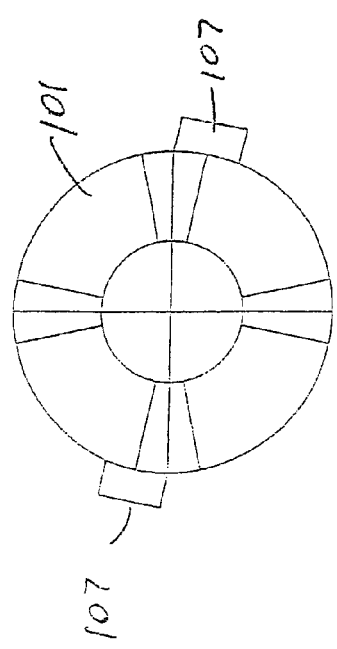
Fig. 69

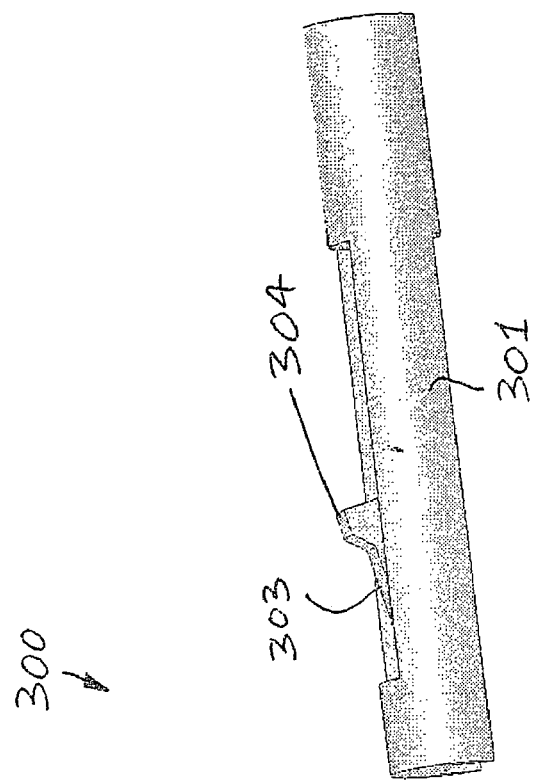
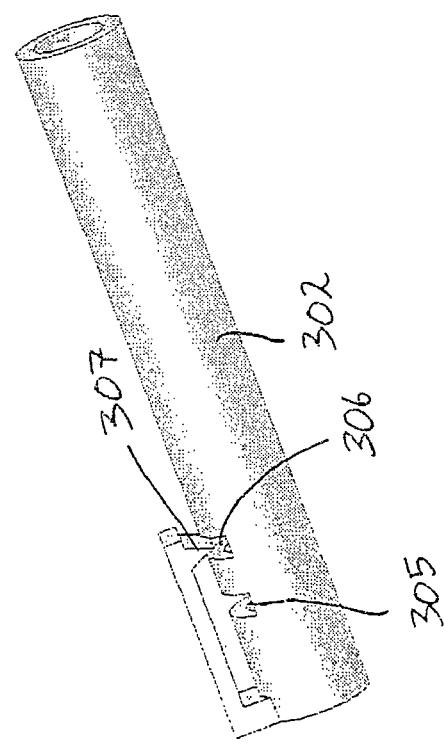
Fig. 74

HAEMOSTASIS DEVICE

This is a complete application claiming benefit of provisional 60/497,570 filed Aug. 26, 2003.

This invention relates to a haemostasis device.

It is known to employ a haemostasis device for providing haemostasis while facilitating passage of a medical device, for example an elongated member, such as a guidewire or a catheter, through the haemostasis device and into a vasculature. Such a haemostasis device may be used, for example, in an interventional procedure, such as a balloon angioplasty and/or a stenting procedure.

Currently available haemostasis devices have a number of disadvantages. They can be cumbersome and time-consuming to use by a clinician. Some devices require manual threading of caps, and it can be difficult to effect adequate sealing properties. If valves are left open or partially open, this can lead to patient blood loss through seal leakage, with consequent reduced blood pressure. If users are unclear about the valves being open, half-open or closed, this can lead to expensive stents getting damaged by being pulled through half-open seals. In conventional systems there is some concern about stents/balloons with value-added payloads, such as drug-eluting coatings, coming into direct contact with the seal materials.

This invention is directed towards providing an improved haemostasis device.

STATEMENTS OF INVENTION

According to the invention there is provided a haemostasis device comprising:
a housing defining a lumen extending therethrough;
a first seal having a closed configuration to seal across the lumen, and an open configuration to facilitate passage of a medical device through the lumen;
a tubular member selectively moveable between a retracted configuration and an inserted configuration for movement of the first seal between the closed configuration and the open configuration; and
a guide element movable along a first guide path upon movement of the tubular member from the retracted configuration to the inserted configuration, and movable along a second guide path upon movement of the tubular member from the inserted configuration to the retracted configuration.

In one case the first seal comprises a low pressure seal.

The tubular member provides a simple, visual means of indicating to the user whether the low pressure seal is in the closed configuration or in the open configuration. The user can therefore avoid blood loss through a partially open seal, and can avoid attempting to pass a medical device, such as a stent, through a partially open seal.

The two guide path arrangement results in a fail-safe haemostasis device which is particularly important in the case of medical devices. In particular the two guide path arrangement ensures that the tubular member can only come to rest in either the retracted configuration with the low pressure seal fully closed or in the inserted configuration with the low pressure seal fully open. It is not possible for the tubular member to come to rest in an intermediate configuration with the seal partially open. Thus a user will always be clear about whether the seal is open or closed. It is therefore highly unlikely that a potentially expensive medical device, such as a stent, will be damaged by being inadvertently pulled through a half-open seal.

In one embodiment of the invention the first guide path is offset from the second guide path. The first guide path may be circumferentially offset from the second guide path. The first guide path may be radially offset from the second guide path.

Preferably the housing defines at least one of the guide paths. Ideally the housing defines the first guide path and the second guide path.

In one case at least one of the guide paths comprises a slot in a wall of the housing. Preferably the first guide path comprises a slot in a wall of the housing.

In another case at least one of the guide paths comprises a passage radially inwardly of a wall of the housing. Preferably the second guide path comprises a passage radially inwardly of a wall of the housing.

In another embodiment the guide element is carried by the tubular member. Preferably at least part of the guide element is movable relative to the tubular member. Ideally the guide element comprises a cantilever arm element. At least part of the cantilever arm element may be movable relative to the tubular member in a radial direction. At least part of the cantilever arm element may be movable relative to the tubular member in a circumferential direction. In one case the cantilever arm element comprises a finger element. Preferably the finger element is provided substantially at the free end of the cantilever arm element.

The device may comprise a shield extending over the guide element. The shield prevents external contact with the guide element resulting in inadvertent movement of the tubular member. In this way the seal will be maintained in the desired open or closed configuration. Preferably the shield is provided radially outwardly of the guide element. Ideally the shield is carried by the tubular member.

In one case the tubular member comprises a finger grip configured to be engaged by a finger of a user. The finger grip will typically be engaged by a thumb of a user. Preferably the finger grip is provided at a proximal end of the tubular member. Ideally the finger grip comprises an end cap.

The tubular member may be biased towards the retracted configuration. Preferably the device comprises a biasing element to bias the tubular member towards the retracted configuration. Ideally the biasing element comprises a coiled spring.

In a further embodiment the tubular member is movable through the first seal to move the first seal from the closed configuration to the open configuration. The tubular member may be movable distally through the first seal.

The tubular member preferably defines a lumen extending therethrough aligned with the lumen of the housing.

In one case the tubular member comprises a plunger.

The first seal may be biased towards the closed configuration. Preferably the first seal is of a resilient material. Ideally the first seal comprises polyisoprene rubber.

In one case the first seal comprises a low pressure seal.

In a further embodiment the device comprises a shuttle. Preferably the shuttle defines at least one of the guide paths. Ideally the shuttle defines the first guide path and the second guide path. The shuttle may have a locator for holding the tubular member in at least one position. Ideally the shuttle has first and second spaced-apart locators for holding the tubular member in the retracted and inserted configurations respectively. Most preferably the shuttle comprises a pathway between the first and second locators. In one case the shuttle comprises a first pathway between the first and second locators for movement of the tubular member from the retracted configuration to the inserted configuration, and a second pathway between the second and first locators for movement of the tubular member from the inserted configuration to the retracted configuration. Preferably the tubular member comprises a lug for engagement with the locator of the shuttle.

In another aspect of the invention there is provided a haemostasis device comprising:
a main body portion defining a lumen extending longitudinally therethrough;
a second seal having an open configuration to facilitate passage of a medical device through the lumen, and a sealing configuration to seal around a medical device passing through the lumen; and
a collar member selectively moveable in a substantially radial direction for movement of the second seal between the open configuration and the sealing configuration.

The radial motion of the collar member enables a particularly effective seal to be achieved while minimising the force required to effect the seal. As a result, high pressures may be accommodated to allow, for instance, contrast medium injections to take place.

The collar member is especially effective in achieving a seal between the seal and a flexible element, such as a guidewire. It will also allow the flexible element, such as the guidewire, to be locked in place should it be required by the physician.

The haemostasis device is suitable for effecting a low pressure seal when the pressure differential across the seal is in the range of from 10 psi to 100 psi, typically approximately 40 psi.

The invention also provides in a further aspect a medical device comprising:
a main body portion defining a lumen extending longitudinally therethrough;
a seal having an open configuration and a sealing configuration to seal the lumen; and
a collar member selectively movable in a substantially radial direction for movement of the seal between the open configuration and the sealing configuration.

In one embodiment the device comprises an actuator member engagable with the collar member to selectively move the collar member in a substantially radial direction. Preferably the actuator member is movable longitudinally relative to the main body portion to selectively move the collar member in a substantially radial direction. Ideally at least part of the actuator member is rotatable relative to the main body portion to move the actuator member longitudinally relative to the main body portion. The actuator member may be slidably engagable with the collar member to selectively move the collar member in a substantially radial direction. Most preferably the actuator member comprises a first wedge surface and the collar member comprises a second wedge surface, and the first wedge surface of the actuator member is engagable with the second wedge surface of the collar member to selectively move the collar member in a substantially radial direction. The first wedge surface is preferably slidably engagable with the second wedge surface.

In another embodiment the main body portion is engagable with the collar member to selectively move the collar member in a substantially radial direction. Preferably the main body portion is slidably engagable with the collar member to selectively move the collar member in a substantially radial direction. The main body portion may comprise a third wedge surface and the collar member may comprise a fourth wedge surface, and the third wedge surface of the main body portion may be engagable with the fourth wedge surface of the collar member to selectively move the collar member in a substantially radial direction. In one case the third wedge surface is slidably engagable with the fourth wedge surface.

The collar member may be radially compressible from an open configuration to a sealing configuration. Preferably the collar member comprises a longitudinally extending slit. Ideally the collar member is biased towards the open configuration. Most preferably the collar member comprises a collet.

In another case the second seal comprises a sealing portion movable in a substantially radial direction relative to the main body portion between the open configuration and the sealing configuration. Preferably the collar member extends longitudinally along the sealing portion. Ideally the longitudinal length of the sealing portion is at least 6 mm. Most preferably the longitudinal length of the sealing portion is approximately 9 mm. The length of the sealing portion results in a relatively long sealing contact area. In this manner the sealing force is spread out to achieve an even seal. The long sealing contact area reduces the risk of damage being caused to a guidewire or a catheter when the seal is in the sealing configuration sealing around the guidewire/catheter.

The second seal preferably comprises at least one anchor portion, the radial position of which is fixed relative to the main body portion. Ideally the anchor portion is provided at an end of the second seal. Most preferably the second seal comprises a distal anchor portion at a distal end of the second seal and a proximal anchor portion at a proximal end of the second seal.

In one case the second seal is biased towards the open configuration. Preferably the second seal is of a resilient material. Ideally the seal is of an elastomeric material. The second seal may comprise silicon rubber.

In one case the second seal comprises a high pressure seal. The second seal may comprise a locking seal.

In another embodiment the device comprises a user activated operator member for movement of the second seal between the open configuration and the sealing configuration. Preferably the operator member has two defined positions corresponding to the open configuration and the sealing configuration. Ideally the operator member comprises a pair of camming members movable relative to one another for movement of the second seal between the open configuration and the sealing configuration. At least one of the camming members may be movable relative to the main body portion. In one case the camming member comprises a handle. Preferably the camming member is movable upon rotation of the handle.

In a further embodiment the device comprises a housing defining a lumen, the housing being mateable with the main body portion with the lumen of the housing aligned with the lumen of the main body portion. Preferably the housing and the main body portion comprise corresponding alignment parts for alignment of the housing relative to the main body portion upon mating. In one case one alignment part comprises a male protrusion and the other alignment part comprises a corresponding female recess for receiving the male protrusion. Ideally the male protrusion and the female recess extend longitudinally. The housing may comprise the male protrusion and the main body portion may comprise the female recess.

Preferably the main body portion extends distally of a distal end of the housing.

In one case the device comprises a first seal having a closed configuration to seal across the lumen, and an open configuration to facilitate passage of a medical device through the lumen. Preferably the first seal is located proximally of the second seal. Ideally the device comprises a tubular member selectively movable between a retracted configuration and an inserted configuration for movement of the first seal between the closed configuration and the open configuration. In the inserted configuration, the tubular member may extend distally of the second seal.

In conventional haemostasis devices, there is a possibility that a part of the medical device, such as a stent or an angioplasty balloon, with a value-added payload, such as a drug-eluting coating, could directly contact the seal. This could result in damage to the medical device, for example, a coating of a stent being scraped-off as the medical device passes through the seal. In the haemostasis device of the invention, because the tubular member extends through both of the seals when activated, the tubular member effectively cannulates both seals to ensure no inadvertent contact between a medical device, such as a stent, and the seals.

Desirably the device comprises a guide element movable along a first guide path upon movement of the tubular member from the retracted configuration to the inserted configuration, and movable along a second guide path upon movement of the tubular member from the inserted configuration to the retracted configuration.

In a further case the device comprises:
a gripping element to facilitate gripping of the device by a user; the gripping element comprising a first finger grip configured to be engaged by a first finger of the user, and a second finger grip configured to be engaged by a second finger of the user.

The device may comprise a side port in communication with the lumen. Preferably the side port is located distally of the seal. Ideally the finger grip is located distally of the side port. Most preferably the device comprises an injector member for injecting a fluid into the side port. The finger grip is preferably located distally of the seal.

According to a further aspect of the invention there is provided a haemostasis device comprising:
a housing defining a lumen extending therethrough;
a first seal having a closed configuration to seal across the lumen, and an open configuration to facilitate passage of a medical device through the lumen;
a tubular member selectively movable between a retracted configuration and an inserted configuration for movement of the first seal between the closed configuration and the open configuration; and
a stop element to selectively hold the tubular member in the retracted configuration and/or in the inserted configuration.

In one embodiment the stop element is movable between an engaging position for holding the tubular member in the retracted configuration and/or in the inserted configuration, and a release position for movement of the tubular member between the retracted configuration and the inserted configuration. Preferably the stop element is biased towards the engaging position.

The stop element may comprise a male protruding part for reception in a corresponding female recess to selectively hold the tubular member in the retracted configuration and/or in the inserted configuration.

In one case the stop element is carried by the tubular member. Preferably the stop element is movable relative to the tubular member. Ideally the stop element comprises a cantilever arm element. The cantilever arm element may comprise a finger element. Most preferably the finger element is provided substantially at the free end of the cantilever arm element.

In one case, in the engaging position, the stop element is engagable with the housing. Preferably the housing comprises an opening for receiving at least part of the stop element.

The stop element may be configured to selectively hold the tubular member in the retracted configuration and in the inserted configuration.

The invention also provides in another aspect a delivery device comprising:
a main body portion defining a lumen extending therethrough, through which a medical device may be passed; and
a gripping element to facilitate gripping of the device by a user;
the gripping element comprising a first finger grip configured to be engaged by a first finger of the user, and a second finger grip configured to be engaged by a second finger of the user.

The two finger grips enable a user to grip the device in a more secure, balanced manner.

Typically one finger grip is engaged by an index finger of the user and the other finger grip is engaged by a long finger of the same hand.

Alternatively one finger grip may be engaged by a small finger of the user and the other finger grip may be engaged by a ring finger of the same hand. The user could then use the index finger and thumb of the same hand to manipulate a guidewire passing through the device.

It will be appreciated that the finger grips may be engaged in any suitable manner by the user.

Preferably the finger grip extends outwardly from the main body portion. The finger grip may be substantially arcuate in shape. The arcuate shape of the finger grip enhances the ergonomic suitability of the finger grip. Ideally the concave side of the arcuate finger grip faces substantially distally.

The finger grip may be attached to the main body portion. In one case the first finger grip is provided on an opposite side of the main body portion to the second finger grip. Preferably the finger grips diametrically oppose one another. Most preferably the first finger grip is provided at substantially the same region along the length of the main body portion as the second finger grip.

In another embodiment the main body portion comprises a side port in communication with the lumen. The finger grip is preferably located distally of the side port. The device may comprise an injector member for injecting a fluid into the side port.

In another case the device comprises a second seal movable between an open configuration facilitating passage of a medical device through the lumen, and a sealing configuration sealing around a medical device passing through the lumen. Preferably the finger grip is located distally of the second seal.

Desirably the device comprises a haemostasis device.

In a further embodiment the device comprises a connector member for connecting a distal end of the device to a proximal end of a catheter. Preferably the connector member comprises at least one gripping element upstanding from an outer surface of the connector member to facilitate gripping of the connector member by a user.

In another aspect of the invention there is provided a delivery device comprising:
a main body portion defining a lumen extending therethrough, through which a medical device may be passed; and
a connector member for connecting a distal end of the main body portion to a proximal end of a catheter;
the connector member comprising at least one gripping element upstanding from an outer surface of the connector member to facilitate gripping of the connector member by a user.

In one embodiment the gripping element extends substantially longitudinally along the connector member. Preferably the gripping element is substantially elongate. The elongate nature of the finger grip enables a user to more easily grip the connector member. Ideally the gripping element comprises a side wing.

The gripping element preferably upstands by at least 2 mm from the outer surface of the connector member. Ideally the gripping element upstands by approximately 3 mm from the outer surface of the connector member. It has been found that by ensuring that the gripping element upstands from the connector member outer surface by a relatively large distance, it is easier for a user to grip the connector member to achieve connection to a catheter.

The device may comprise a first gripping element configured to be engaged by a first finger of a user, and a second gripping element configured to be engaged by a second finger of a user. Typically one finger grip is engaged by a thumb of the user and the other finger grip is engaged by an index finger of the same hand. Preferably the first gripping element is provided on an opposite side of the connector member to the second gripping element. Ideally the gripping elements diametrically oppose one another.

Most preferably the outer surface of the connector member is substantially smooth between the at least one gripping element.

The connector member may be rotatably coupled to the main body portion. In one case the connector member comprises a coupling part for coupling the connector member to a catheter. Ideally the coupling part comprises a thread formation on the connector member.

In a preferred case the connector member comprises a luer.

In a particularly preferred case the device comprises a haemostasis device.

The medical device may comprise a guidewire, and/or a catheter, such as a balloon angioplasty catheter or a stent delivery catheter.

The invention further provides in another aspect a method of performing a haemostasis procedure, the method comprising the steps of:
providing a haemostasis device comprising a seal and a tubular member;
moving the tubular member between a retracted configuration and an inserted configuration to move the seal between a closed configuration sealing the haemostasis device, and an open configuration facilitating passage of a medical device through the haemostasis device;
guiding at least part of the tubular member along a first guide path upon movement of the tubular member from the retracted configuration to the inserted configuration; and
guiding at least part of the tubular member along a second guide path upon movement of the tubular member from the inserted configuration to the retracted configuration.

In one case the method comprises the step of passing a medical device through the seal in the open configuration, the tubular member having previously been moved from the retracted configuration to the inserted configuration to move the seal from the closed configuration to the open configuration.

In another aspect the invention provides a method of performing a haemostasis procedure, the method comprising the steps of:
providing a haemostasis device comprising a seal and a tubular member;
moving the tubular member from a retracted configuration to an inserted configuration to move the seal from a closed configuration sealing the haemostasis device to an open configuration;
inserting a medical device through the seal in the open configuration;
moving the tubular member from the inserted configuration to the retracted configuration to move the seal from the open configuration to the closed configuration sealing around the medical device; and
passing the medical device through the seal in the closed configuration.

The invention provides in a further aspect a method of performing a haemostasis procedure, the method comprising the steps of:
providing a haemostasis device comprising a seal and a collar member; and
moving the collar member in a substantially radial direction to move the seal between an open configuration facilitating passage of a medical device through the haemostasis device, and a sealing configuration sealing around the medical device.

In one embodiment the method comprises the step of longitudinally moving an actuator member to move the collar member in the substantially radial direction. Preferably at least part of the actuator member is rotated to longitudinally move the actuator member. At least part of the actuator member may slidably engage the collar member to move the collar member in the substantially radial direction.

In one embodiment the method comprises the step of passing a medical device through the seal in the open configuration, the collar member subsequently being moved in the substantially radial direction to move the seal from the open configuration to the sealing configuration.

The method may comprise the step of connecting a distal end of the haemostasis device to a proximal end of a catheter.

The medical device may comprise a guidewire, and/or a catheter, such as a balloon angioplasty catheter or a stent delivery catheter.

The haemostasis device of the invention provides a simple, easy-to-use mechanism, whereby open/close positions are readily recognisable. This substantially reduces the risk of stents getting damaged inadvertently through seals being half-open. It is ideally suited to the delivery of fragile loads on balloon catheters or stent-delivery systems, such as drug-eluting stents, in particular through the avoidance of any seal contact. Moreover, correct use of the sealing mechanism can lead to a significant reduction in blood loss. As well as saving time through the avoidance of wearisome threading/re-threading of valves, it also affords improved ergonomics for the user by the design of the enhanced cap and the addition of finger rests.

BRIEF DESCRIPTION OF THE DRAWINGS

The invention will be more clearly understood from the following description of some embodiments thereof, given by way of example only, with reference to the accompanying drawings, in which:

FIGS. 8 to 10 are enlarged, cross-sectional, side views of the device and the guidewire of FIG. 7, in use;

FIGS. 14, 15, 21 to 24, 28 to 31 and 34 to 39 are views similar to FIGS. 11 and 12 of the device, in use;

FIG. 16 is a partially cross-sectional, side view of the device of FIG. 3 in an in-use position corresponding to FIGS. 14 and 15;

FIGS. 17 and 18 are enlarged views of parts of the device of FIG. 16;

FIG. 19 is a partially cross-sectional, side view of the device of FIG. 3 in another in-use position;

FIG. 20 is an enlarged view of a part of the device of FIG. 19;

FIG. 25 is a partially cross-sectional, side view of the device of FIG. 3 in an in-use position corresponding to FIGS. 23 and 24;

FIGS. 26 and 27 are enlarged views of parts of the device of FIG. 25;

FIG. 43 is an elevational view of the device of FIG. 42;

FIG. 44 is a cross sectional view on the line A-A in FIG. 43;

FIGS. 56(a) to 56(d) are views of a first cam element of the device;

FIGS. 57(a) to 57(d) are views of a second cam element of the device;

FIGS. 61(a) to 61(d) are views of the other half of the shuttle;

FIGS. 63(a) to 63(c) are perspective views also illustrating the movement of the plunger relative to the shuttle;

FIGS. 64(a) to 64(g) are views on a large scale illustrating the movement of the plunger lugs relative to the shuttle;

FIG. 65 is a perspective view of an alternative cam system for the haemostasis device;

FIGS. 66 to 69 are views of a lower cam of the cam system of FIG. 65;

FIG. 74 is a perspective view of two parts of another haemostasis device according to the invention;

DETAILED DESCRIPTION

Referring to FIGS. 1 to 39, there is illustrated a haemostasis device 200 according to the invention. The device 200 is a rotating haemostasis valve and comprises two sealing mechanisms. The device 200 is constructed using injection moulded plastic. Each sealing mechanism has an elastomeric component which is actuated to perform an "opening" or "closing" action.

Figure 1:
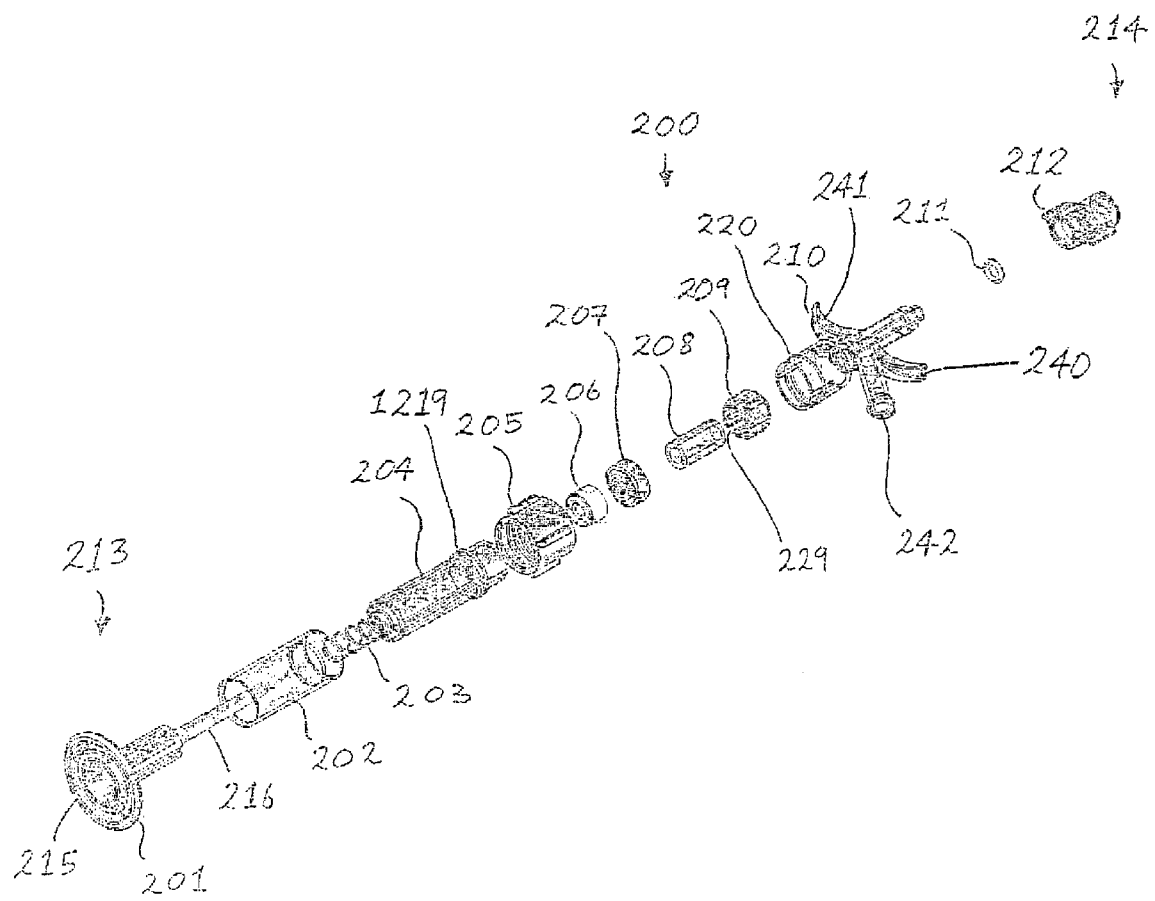
FIG. 1 is an exploded, perspective view of a haemostasis device according to the invention.
Figure 2:
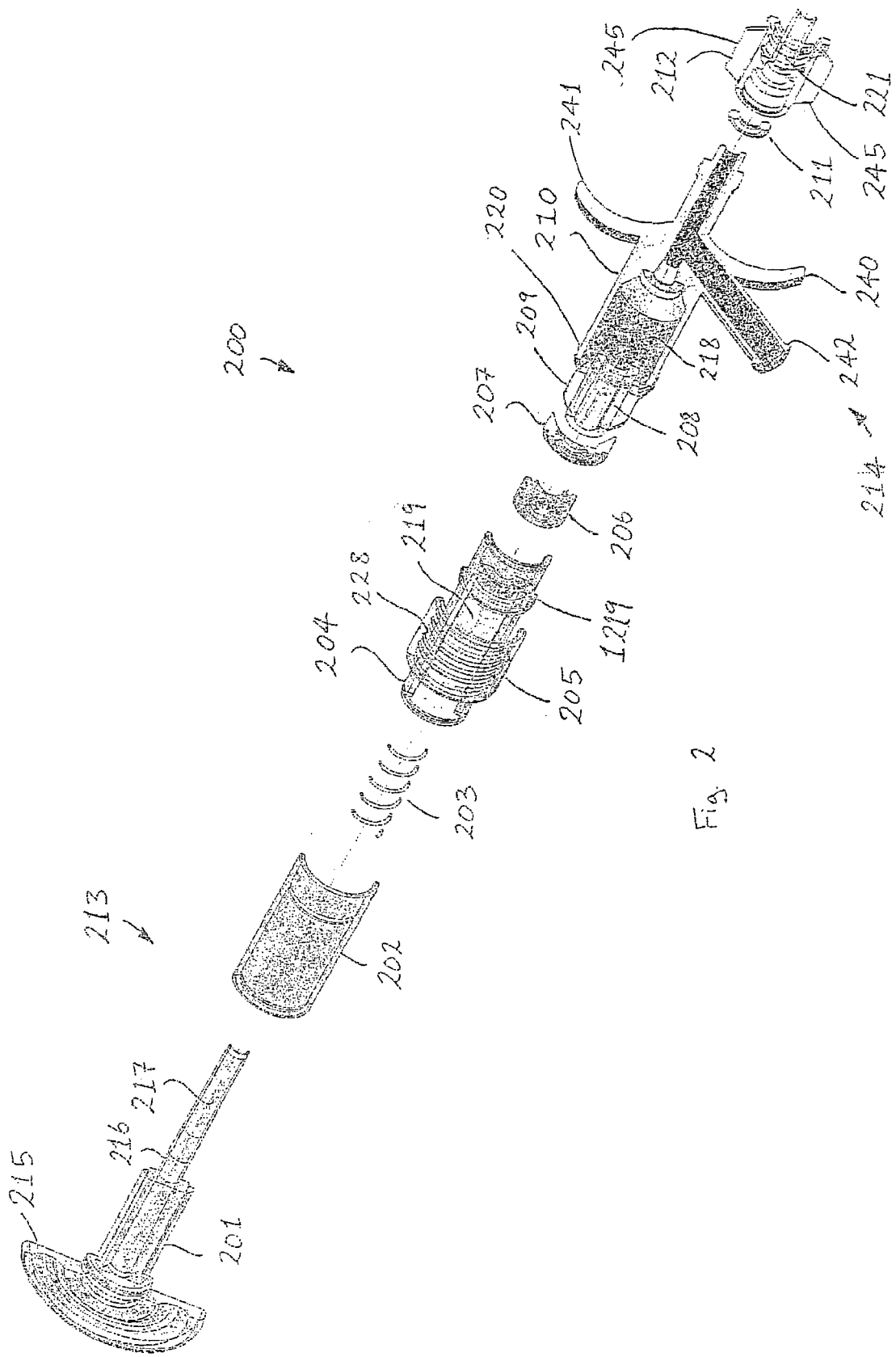
FIG. 2 is an exploded, cut-away, perspective view of the device of FIG. 1.

As illustrated in FIGS. 1 and 2, moving from the proximal end 213 to the distal end 214, the device 200 comprises:
a bayonet 201;
a skirt 202;
a coiled spring 203;
an upper body housing 204;
a roto-lock nut 205;
a low pressure seal 206;
a spacer 207;
a high pressure seal 208;
a collet 209;
a lower main body portion 210;
an O-ring 211; and
a luer 212.

The bayonet 201 comprises a proximal end cap 215 and a tubular plunger member 216 extending distally from the end cap 215. A lumen 217 extends through the bayonet 201.

Figure 11:
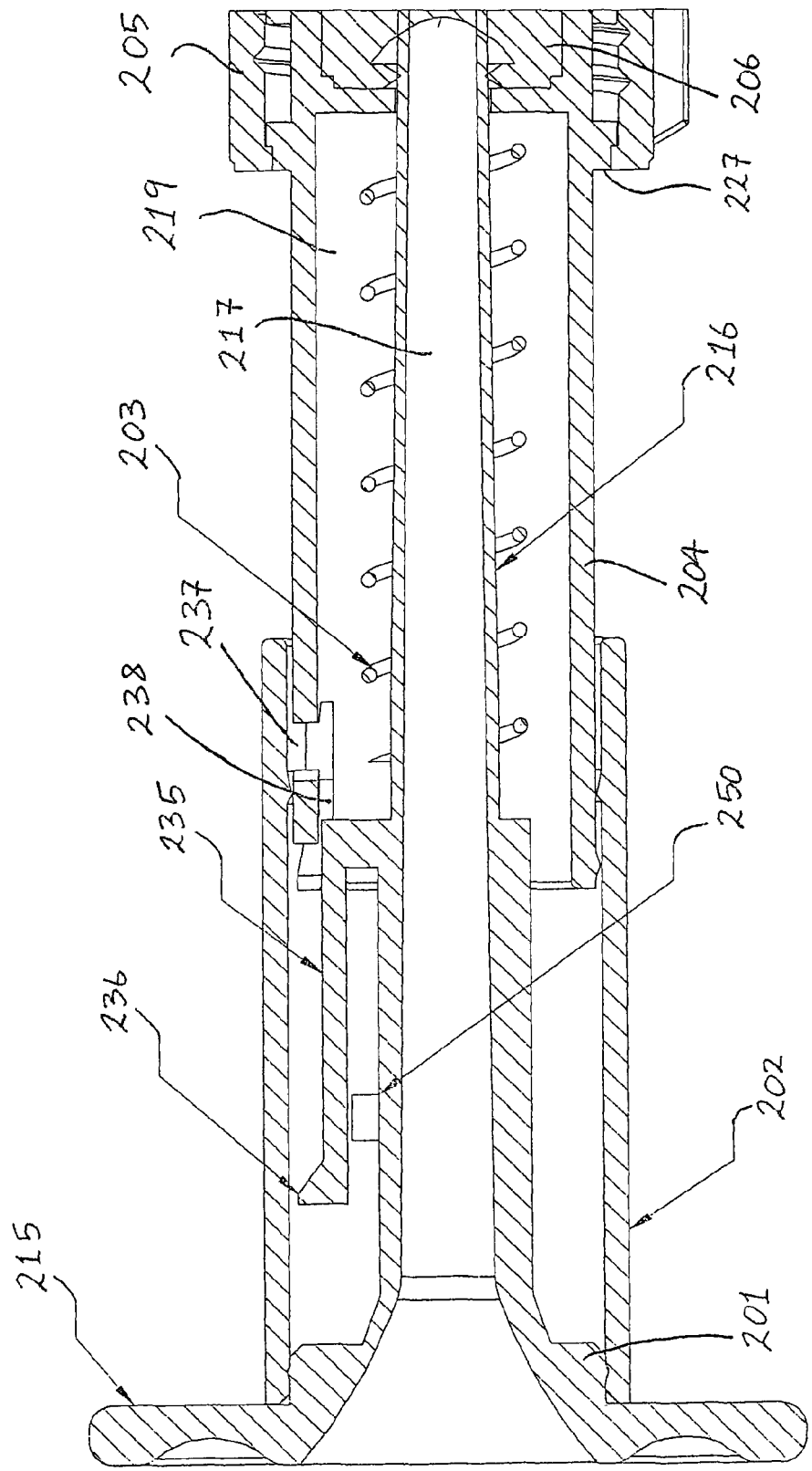
FIG. 11 is an enlarged, cross-sectional, side view of a proximal end of the device of FIG. 3.
Figure 12:
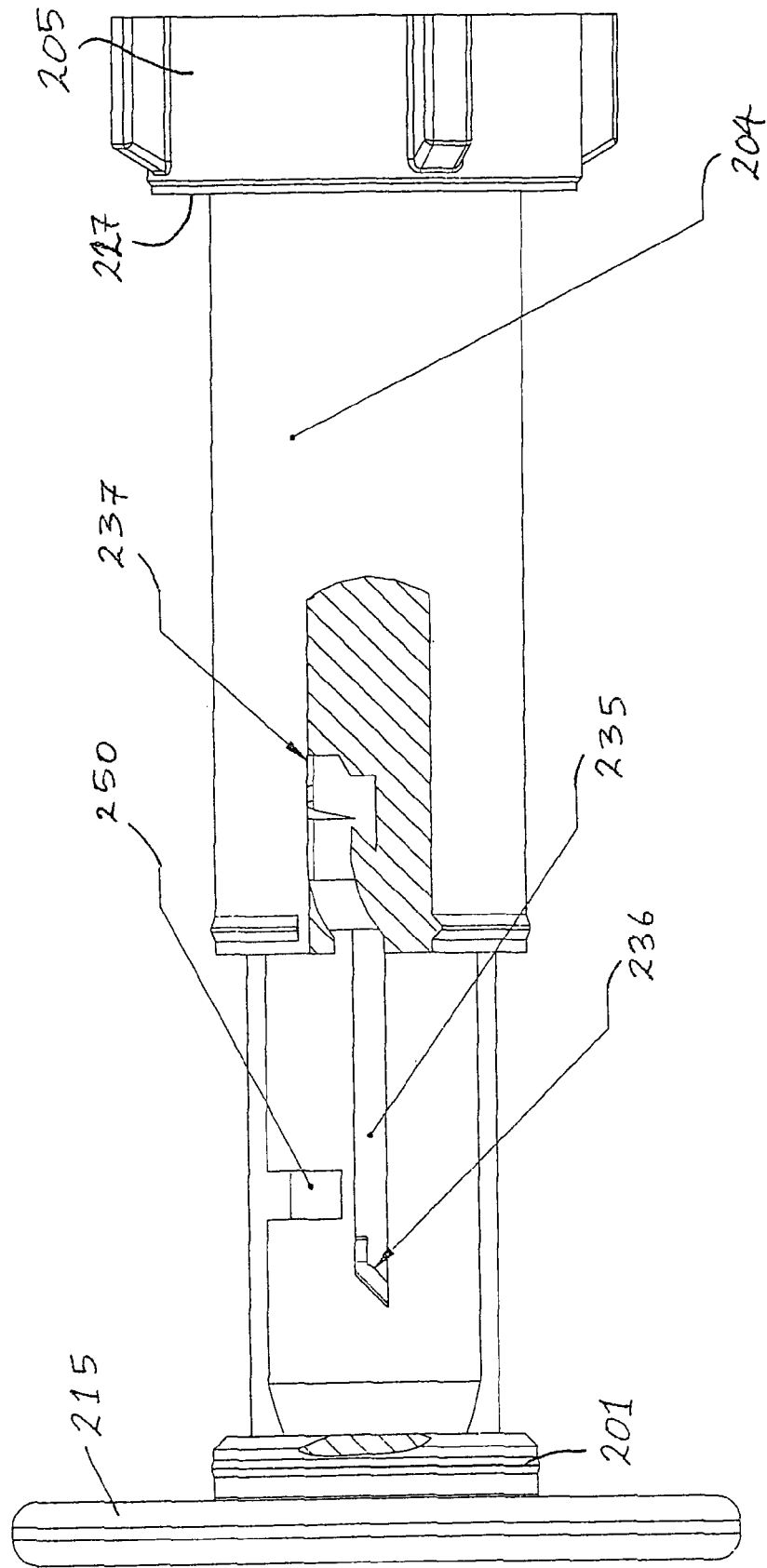
FIG. 12 is an enlarged, partially cut-away, plan view of the proximal end of the device of FIG. 3.

The tubular member 216 supports a cantilever arm 235 with an upstanding finger 236 at the free proximal end of the cantilever arm 235 (FIG. 11). The cantilever arm 235 extends longitudinally proximally, and the finger 236 upstands radially outwardly. The finger 236 at the proximal end of the cantilever arm 235 is movable relative to the tubular member 216 in the radial direction and in the circumferential direction.

A platform 250 is provided upstanding radially outwardly from the wall of the tubular member 216. The platform 250 is located radially inwardly of the cantilever arm 235.

The end cap 215 may be engaged by a finger of a user, typically the user's thumb, to grip or move the bayonet 201.

The skirt 202 is fixedly attached to the proximal end cap 215 radially outwardly of the tubular member 216 and the cantilever arm 235, and the skirt 202 extends distally of the proximal end cap 215 to shield the cantilever arm 235 and the finger 236 (FIG. 11).

A lumen 219 extends longitudinally through the housing 204. When the device 200 is assembled (FIG. 3), the tubular member 216 extends distally into the housing lumen 219 with the bayonet lumen 217 aligned with the housing lumen 219, and the coiled spring 203 is mounted around the distal end of the tubular member 216 in the housing lumen 219.

A slot 237 is provided in the wall of the housing 204 (FIG. 12), and a passage 238 is defined through the housing lumen 219 radially inwardly of the wall of the housing 204 (FIG. 14). The finger 236 of the bayonet 201 may be slidably moved through the slot 237 and may be passed through the passage 238. In this manner, the slot 237 acts as a first guide path to guide movement of the finger 236, and the passage 238 acts as a second guide path to guide movement of the finger 236.

Figure 13:
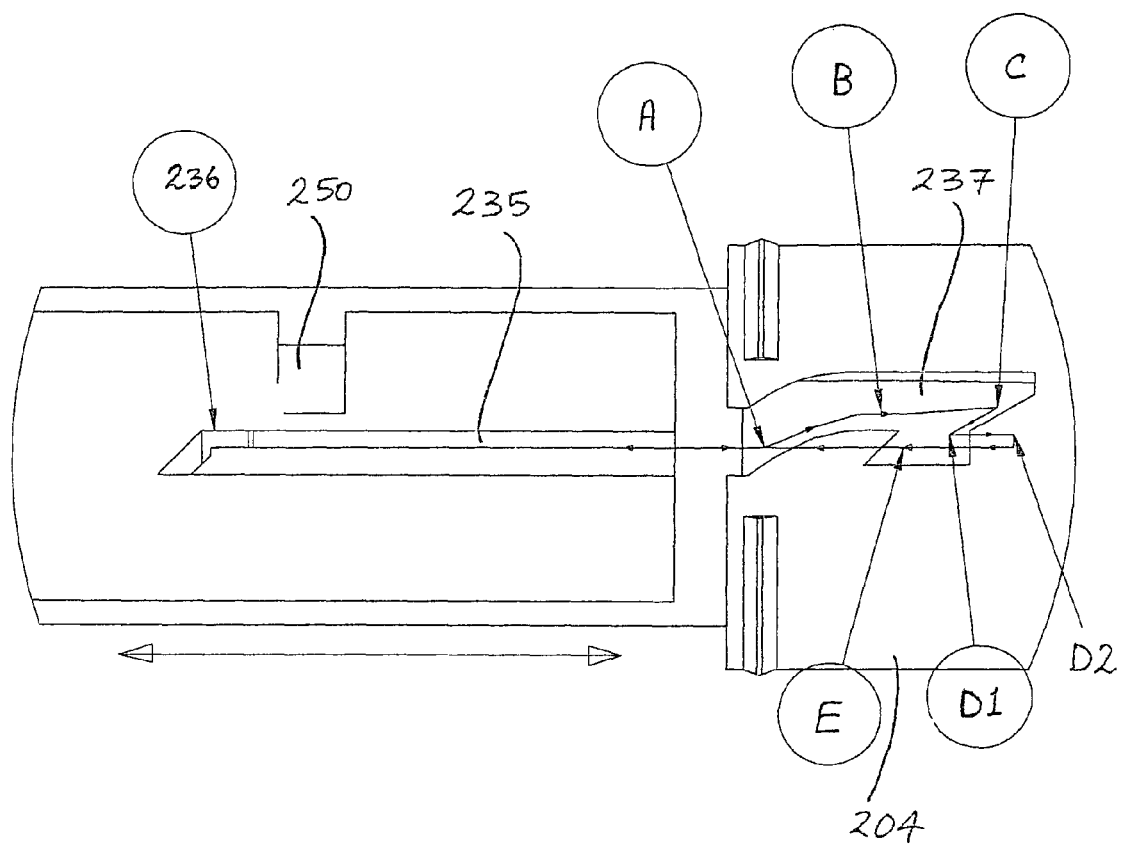
FIG. 13 is a schematic plan view of a part of the device of FIG. 12 illustrating operation of the device.

As illustrated in FIG. 13, the slot 237 is circumferentially offset from the passage 238, and as illustrated in FIGS. 21 to 39, the slot 237 is also radially offset from the passage 238.

A lumen 218 extends longitudinally through the main body portion 210. When the device 200 is assembled (FIG. 3), the low pressure seal 206, the spacer 207, the high pressure seal 208 and the collet 209 are housed within the main body portion lumen 218. In particular the low pressure seal 206 is located proximally of the high pressure seal 208 with the spacer 207 located between the low pressure seal 206 and the high pressure seal 208. The collet 209 is located radially outwardly of the high pressure seal 208 extending longitudinally along a portion of the high pressure seal 208.

Figures 32, 33:
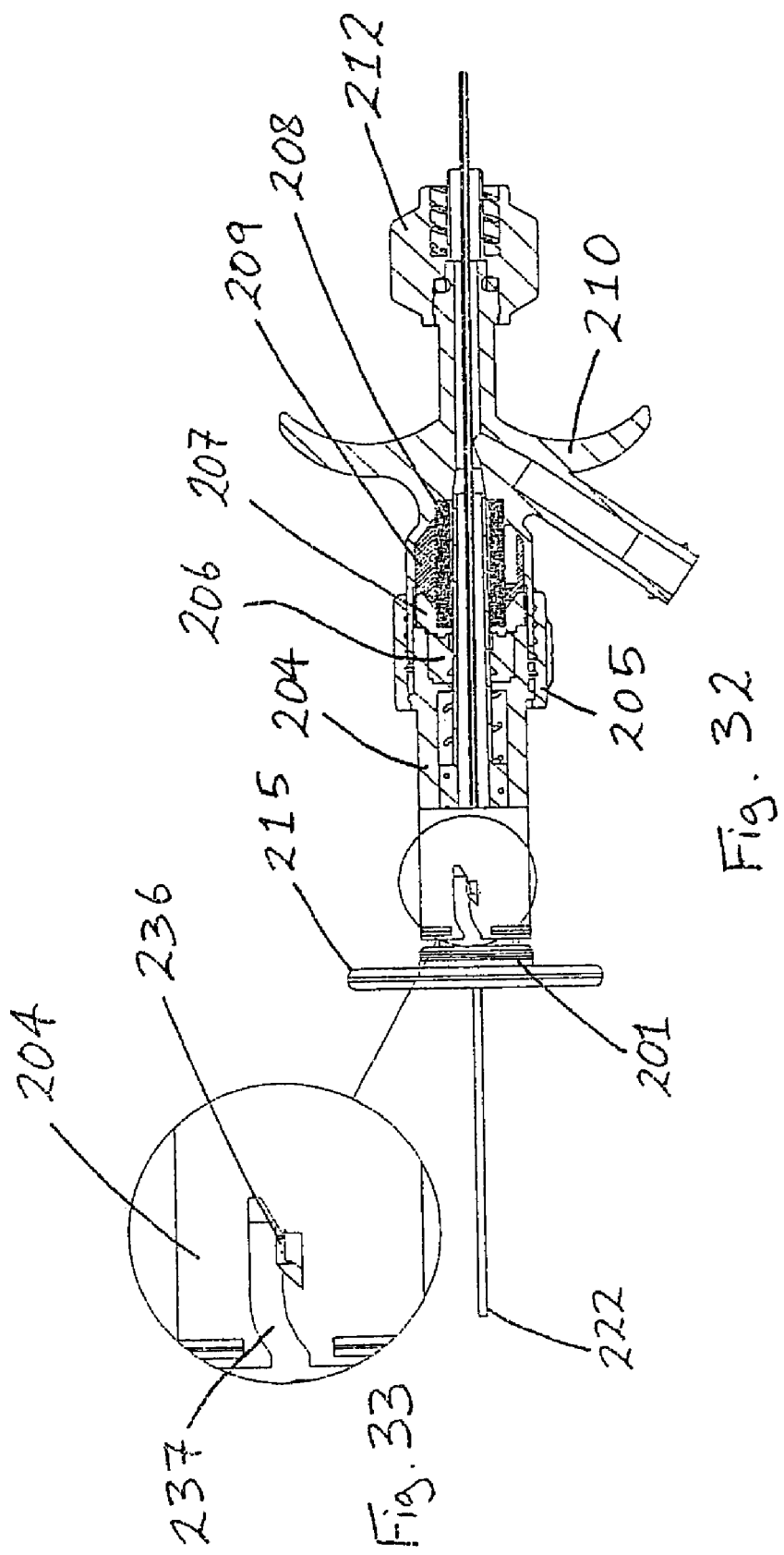
FIG. 32 is a partially cross-sectional, side view of the device of FIG. 3 in an in-use position corresponding to FIGS. 30 and 31.
FIG. 33 is an enlarged view of a part of the device of FIG. 32.
Figure 40:
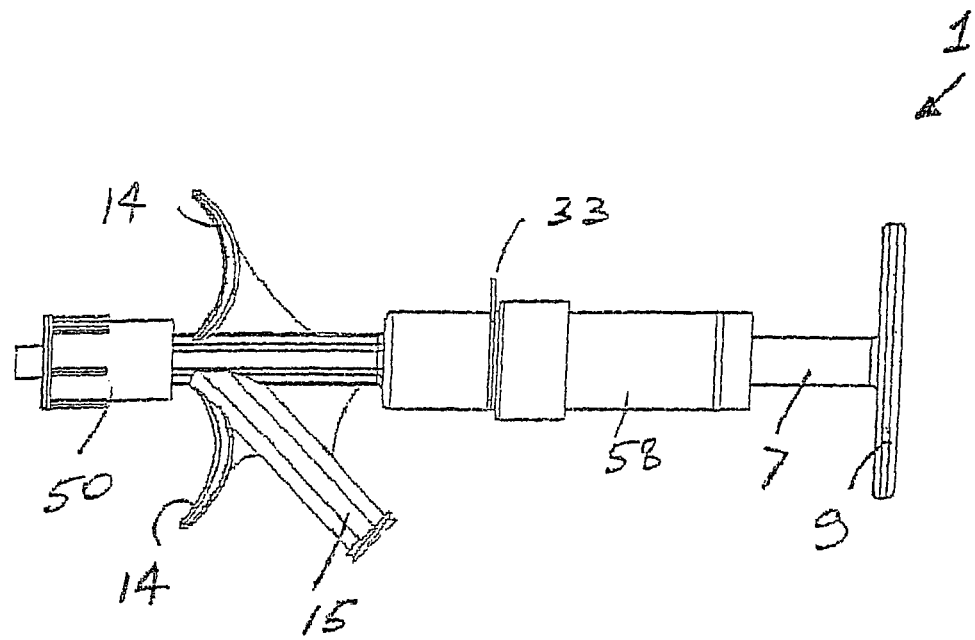
FIG. 40 is an elevational view of a haemostasis device according to the invention with a plunger in an extended configuration.
Figure 41:
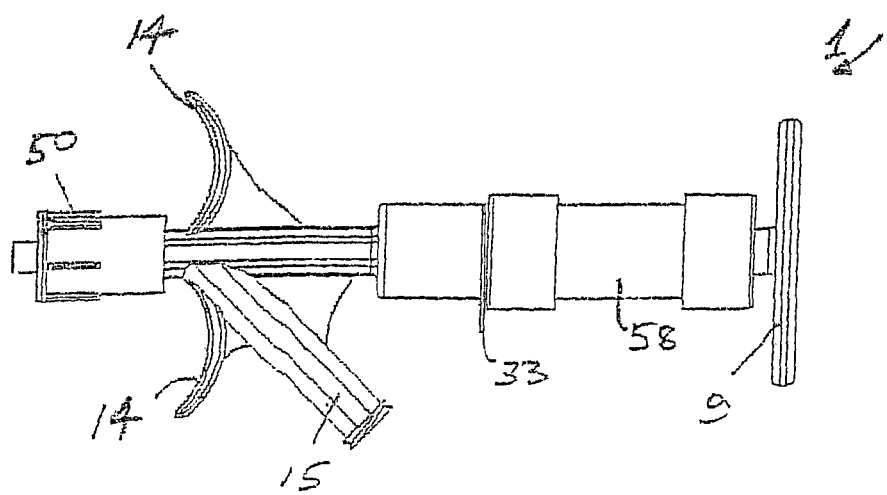
FIG. 41 is a view of the device of FIG. 40 with the plunger depressed.
Figure 42:
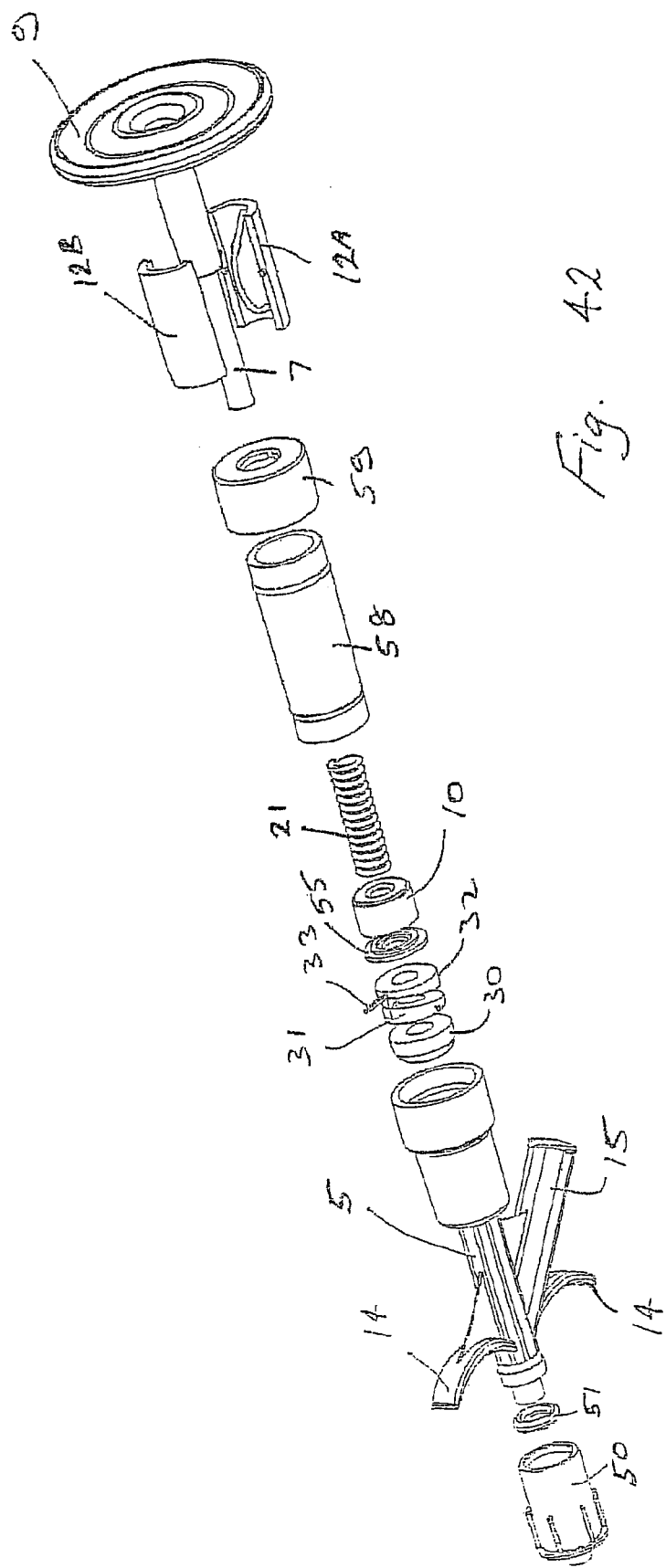
FIG. 42 is an exploded perspective view of another haemostasis device.
Figure 45:
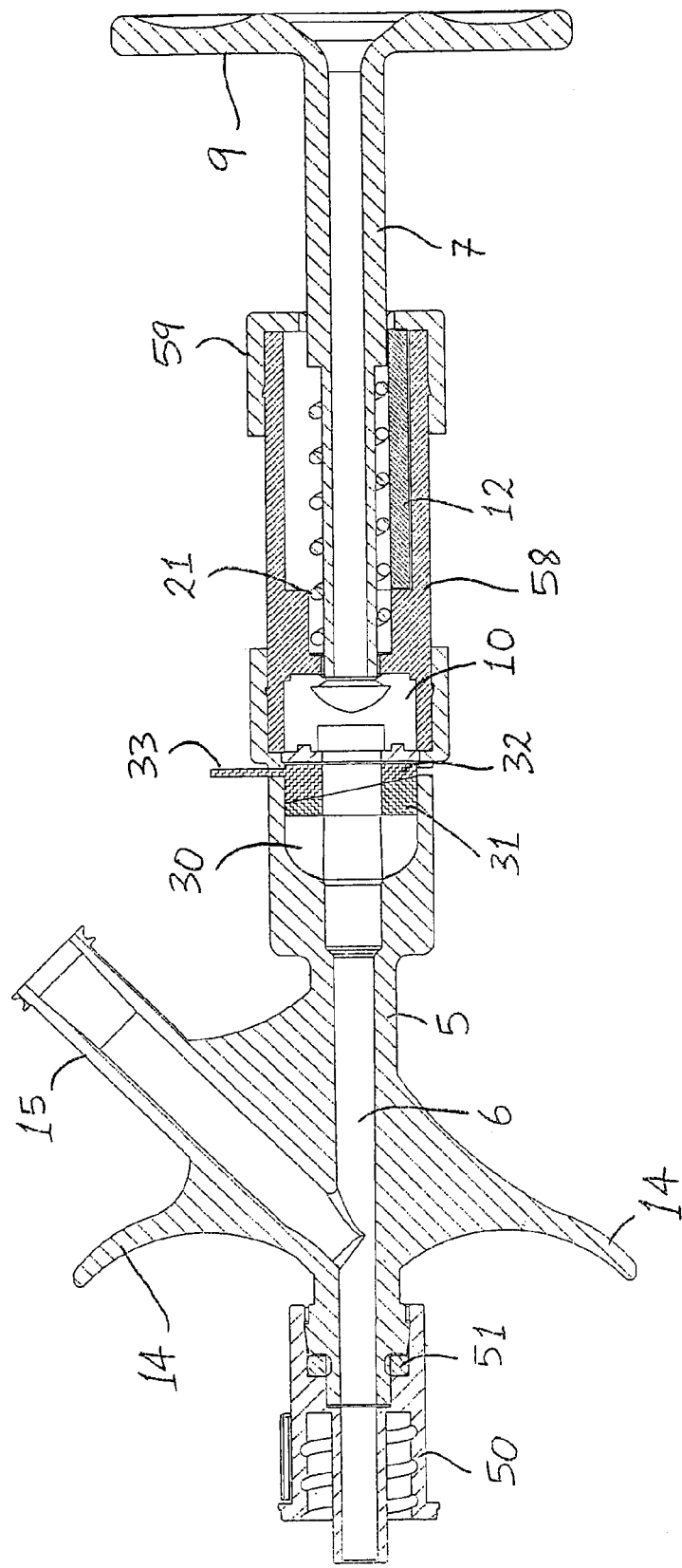
FIG. 45 is a cross sectional view of the device with the plunger extended, the cams closed and the high pressure seal open.

The low pressure seal 206 has a closed configuration to seal across the housing lumen 219 (FIGS. 3 to 6) or to seal around a medical device, such as a guidewire 222, passing through the housing lumen 219 (FIGS. 7 to 10), and an open configuration to facilitate passage of a medical device through the housing lumen 219 (FIGS. 25, 26, 32).

When the low pressure seal 206 is in the closed configuration sealing around a medical device, such as a guidewire 222, it is possible to slide the guidewire 222 through the low pressure seal 206 while still maintaining sealing around the guidewire 222.

The low pressure seal 206 is provided, in this case, in the form of polyisoprene rubber. The design of the low pressure seal 206 and the resilient nature of this material ensures that the low pressure seal 206 is biased towards the closed configuration (FIGS. 3 to 10).

The high pressure seal 208 has an open configuration (FIGS. 3, 4, 7, 8) to facilitate passage of a medical device, such as a guidewire 222, through the main body portion lumen 218, and a sealing configuration to seal across the main body portion lumen 218 (FIG. 6) or to seal around a medical device passing through the main body portion lumen 218 (FIG. 10).

In this case, the high pressure seal 208 is a locking seal. When the locking seal 208 is in the sealing configuration sealing around a medical device, such as a guidewire 222, the guidewire 222 is locked in position relative to the seal 208. It is not possible to slide the guidewire 222 through the seal 208 when in the sealing configuration. The seal 208 thus effects the dual functions of sealing around the guidewire 222 and maintaining the guidewire 222 in position.

Figure 6:
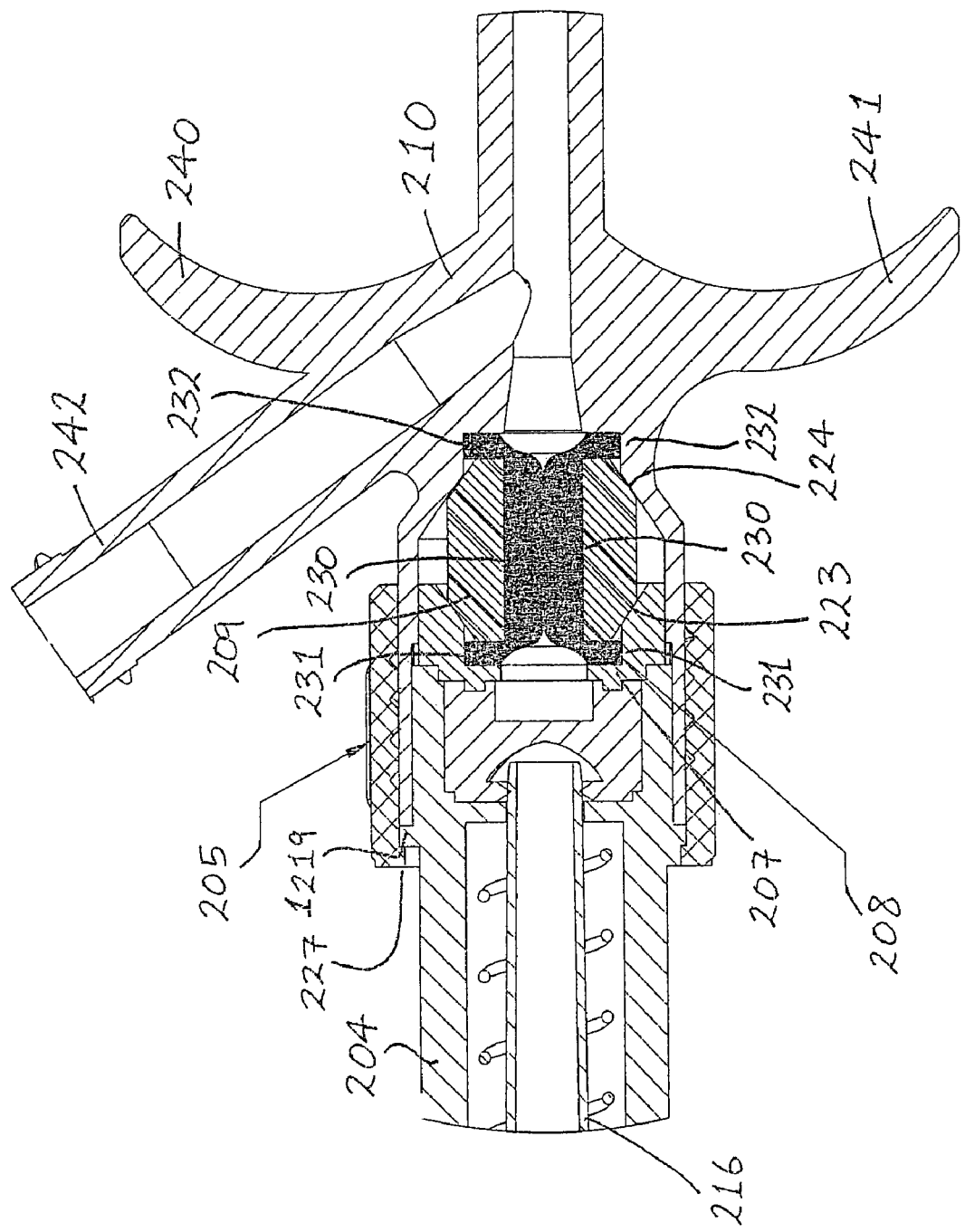
Figure 7:
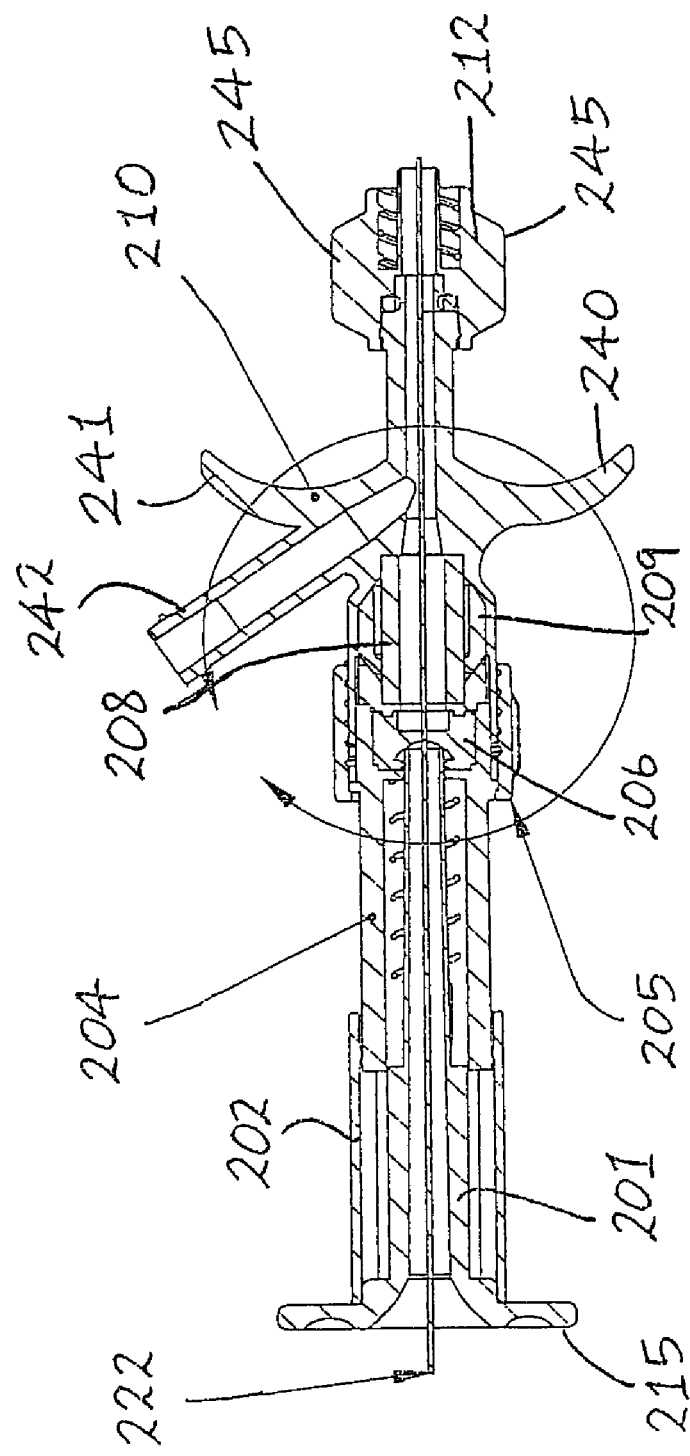
FIG. 7 is a cross-sectional view of the device of FIG. 3 and a guidewire.

The high pressure seal 208 comprises a tubular sealing portion 230 and an anchor portion 231, 232 at each end of the sealing portion 230. The sealing portion 230 is movable in a substantially radial direction relative to the main body portion 210 between the open configuration (FIGS. 3, 4, 7, 8) and the sealing configuration (FIGS. 6, 10). The radial position of each anchor portion 231, 232 is fixed relative to the main body portion 210.

The longitudinal length of the sealing portion 230 is preferably at least 6 mm, and in this case is approximately 9 mm.

When the device 200 is assembled (FIG. 3), the collet 209 extends longitudinally along the sealing portion 230.

The high pressure seal 208 is provided, in this case, in the form of silicon rubber. The design of the high pressure seal 208 and the resilient nature of this material ensures that the high pressure seal 208 is biased towards the open configuration (FIGS. 3, 4, 7, 8).

The collet 209 has a slit 229 extending longitudinally along the collet 209. The slit 229 enables the collet 209 to compress radially inwardly from an open configuration (FIG. 4) to a sealing configuration (FIG. 6). The collet 209 is self-biased towards the open configuration.

The main body portion 210 comprises two grips 240, 241 diametrically opposing each other on opposite sides of the main body portion 210. The finger grips 240, 241 are provided at the same region along the length of the main body portion 210 distally of the high pressure seal 208. Each finger grip 240, 241 is substantially arcuate in shape and extends outwardly from the main body portion 210 with the concave side of the arc facing substantially distally. The first finger grip 240 is suitable for being engaged by a first finger of a user, typically the user's index finger, and the second finger grip 241 is suitable for being engaged by a second finger of the user, typically the user's long finger. In this manner, the finger grips 240, 241 act as a gripping element to facilitate gripping of the device 200 by a user.

A side port 242 is provided in the main body portion 210 in communication with the main body portion lumen 218. The side port 242 is located distally of the high pressure seal 208 and located proximally of the finger grips 240, 241.

An injector member may be employed to inject a fluid, such as a contrast medium, into the side port 242.

The housing 204 is mateable with the main body portion 210 with the housing lumen 219 aligned with the main body portion lumen 218. When the device 200 is assembled (FIG. 3), the distal end of the housing 204 extends into the proximal end of the main body portion lumen 218 to engage the low pressure seal 206 to hold the low pressure seal 206, the spacer 207, the high pressure seal 208 and the collet 209 within the main body portion lumen 218. In the assembled device 200 (FIG. 3), the main body portion 210 extends distally of the distal end of the housing 204.

An outwardly protruding male spline is provided extending longitudinally along the housing 204, and a corresponding female recess is provided extending longitudinally along the wall of the main body portion lumen 218. The spline is received in the recess to assist alignment of the housing 204 relative to the main body portion 210 upon mating of the housing 204 with the main body portion 210.

Figure 3:
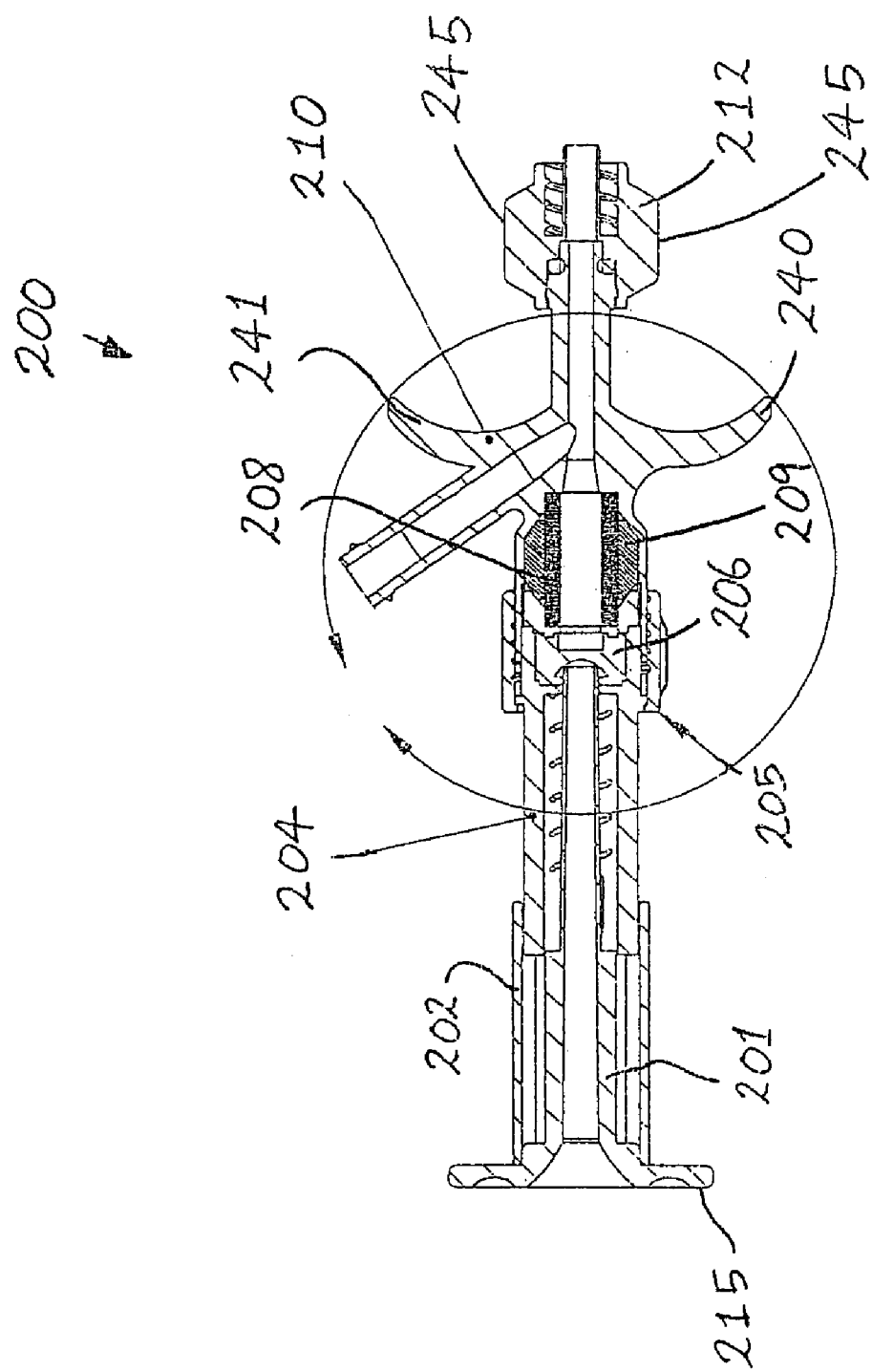
FIG. 3 is a cross-sectional, side view of the device of FIG. 1, when assembled.

The roto-lock nut 205 is mounted around the housing 204 and the main body portion 210 to hold the housing 204 and the main body portion 210 together, when the device 200 is assembled (FIG. 3). In particular, a shoulder 227 of the roto-lock nut 205 engages an outwardly protruding shoulder 1219 on the housing 204, and an internal nut thread 228 engages an outwardly protruding tooth 220 on the main body portion 210.

The tubular member 216 is selectively movable in a longitudinal direction relative to the housing 204 and relative to the main body portion 210 between a retracted configuration (FIGS. 3 to 10, 16 to 18) and an inserted configuration (FIGS. 25 to 27, 32) for movement of the low pressure seal 206 between the closed configuration and the open configuration. In particular the tubular member 216 may be moved distally through the low pressure seal 206 to move the low pressure seal 206 from the closed configuration to the open configuration.

The coiled spring 203 acts to bias the tubular member 216 towards the retracted configuration.

As the tubular member 216 moves from the retracted configuration to the inserted configuration, the finger 236 moves through the slot 237 along the first guide path (FIGS. 21 to 33). As the tubular member 216 moves from the inserted configuration to the retracted configuration, the finger 236 passes through the passage 238 along the second guide path (FIGS. 38 and 39).

In the inserted configuration, the tubular member 216 extends through both the low pressure seal 206 and the high pressure seal 208, with the distal end of the tubular member 216 being located distally of the high pressure seal 208 (FIG. 32).

The low pressure sealing mechanism is referred to by us as a Quikloc mechanism. This Quikloc sealing mechanism forces a tube 216 through the centre of a rubber low pressure seal 206 thus opening it and allowing flow of liquids or gases. The Quikloc mechanism uses a series of angled faces to guide a pin 236 and arm 235 which is fixed to the tube 216 through a pattern. The pattern comprises two mutually exclusive 'stop' positions, one for the closed position and one for the open position. A metal spring 203 returns the mechanism to its closed position from its open position.

As illustrated in FIGS. 4 to 6 and 7 to 10, rotation of the roto-lock nut 205 relative to the main body portion 210 causes longitudinal movement of the roto-lock nut 205 relative to the main body portion 210 due to the inter-engagement of the tooth 220 with the thread 228, which causes longitudinal movement of the housing 204 relative to the main body portion 210 due to the inter-engagement of the nut shoulder 227 with the housing shoulder 1219, which in turn causes longitudinal movement of the spacer 207 relative to the main body portion 210 due to the engagement of the housing 204 with the spacer 207.

The collet 209 has a proximal tapered wedge surface 223 which engages with a corresponding tapered wedge surface 225 on the spacer 207, and a distal tapered wedge surface 224 which engages with a corresponding tapered wedge surface 226 on the main body portion 210. Longitudinal movement of the spacer 207 relative to the main body portion 210 thus causes the spacer wedge surface 225 to slidably engage with the collet proximal wedge surface 223 and the distal wedge surface 224 to slidably engage the main body portion wedge surface 226. In this manner the collet 209 is selectively moved inwardly in a substantially radial direction to move the high pressure seal 208 from the open configuration (FIGS. 3, 4, 7, 8) to the sealing configuration (FIGS. 6, 10). In this way, the collet 209 acts as a collar member for the high pressure seal 208.

The collet sealing mechanism uses two tapered cones to exert force on the split collet 209 and cause it to collapse. The collapsing collet 209 exerts radial force on the seal tube 208 inside it and thus the seal tube 208 collapses. Once closed, the seal tube 208 is held by the threaded nut-to-body 205 and cannot re-open until the nut 205 is turned allowing the tapered cones to move apart. The collet 209 is a flexible plastic and its inherent spring characteristics cause it to re-open and the seal tube 208 opens with it.

A lumen 221 extends longitudinally through the luer 212.

When the device 200 is assembled (FIG. 3), the luer 212 is rotatably mounted to the distal end of the main body portion 210 extending distally of the distal end of the main body portion 210, with the luer lumen 221 aligned with the main body portion lumen 218. The O-ring 211 is enclosed between the distal end of the main body portion 210 and the luer 212. The luer 212 may be rotated while maintaining the position of the main body portion 210 fixed.

The luer 212 may be employed to connect the distal end 214 of the haemostasis device 200 to a proximal end of a catheter. The luer 212 defines an internal thread formation for coupling the luer 212 to a catheter.

Two elongate side wings 245 upstand from the outer surface of the luer 212 by at least 2 mm, and in this case by approximately 3 mm. The wings 245 are provided on opposite sides of the luer 212 diametrically opposing one another. The side wings 245 extend substantially longitudinally along the luer 212, and between the side wings 245 the outer surface of the luer 212 is substantially smooth.

The side wings 245 provide a means by which a user may grip the luer 212. In use, the user will typically engage one side wing 245 with a first finger, such as the user's thumb, and engage the other side wing 245 with a second finger, such as the user's index finger.

The haemostasis device 200 has a rest position, as illustrated in FIG. 3, with the low pressure seal 206 in the closed configuration and the high pressure seal 208 in the open configuration.

To connect the distal end 214 of the device 200 to a proximal end of a catheter, the device distal end 214 is mated with the catheter proximal end. The device distal end 214 is coupled to the catheter proximal end by rotating the luer 212 relative to the catheter proximal end to engage the luer internal thread with the catheter proximal end. In this manner the device 200 is connected to the catheter.

To insert a medical device, such as the guidewire 222, through the device 200, the tubular member 216 is moved from the retracted configuration to the inserted configuration through the low pressure seal 206 to move the low pressure seal 206 from the closed configuration to the open configuration.

In further detail and with reference to FIG. 13, the device 200 comprises the shaped profile slot 237, the plastic pin 236 mounted on the plastic cantilever arm 235 which is free to bend up and down and from side to side, and a series of channels 237, 238 to guide the plunger tube 216 up and down within the upper body housing 204, as the device 200 is actuated.

At rest, the device 200 is in the position illustrated in FIGS. 14 to 18. The return spring 203 is extended to its maximum length and the plastic pin 236 is not engaged by the profile slot 237.

As the device 200 is actuated, the cap 215 is pressed and the plunger tube 216 begins its descent through the upper body housing 204, as illustrated in FIGS. 19 and 20. Position A in FIG. 13 and FIGS. 21 and 22 show the plastic pin 236 as it engages the profile slot 237.

In Position B in FIG. 13 and FIGS. 23 to 27, the plastic pin 236 is under maximum strain and has moved over so that it sits on the platform 250, which prevents the plastic cantilever arm 235 from moving down inside the upper body housing 204.

At the end of its actuation stroke, the plastic pin 236 reaches Position C in FIG. 13 and FIGS. 28 and 29 and stops. The cap 215 is released and the return spring 203 forces the cap 215 to begin its return stroke.

The natural spring in the plastic cantilever arm 235 forces the plastic pin 236 into the acute angle of the profile slot 237 and it engages Position D1 in FIG. 13 and FIGS. 30 to 33. The plunger tube 204 cannot be retracted as the plastic pin 236 is held in place by the force of the return spring 203. The tubular member 216 is now in the inserted configuration with the low pressure seal 206 in the open configuration. The guidewire 222 can then be inserted through the open low pressure seal 206.

To seal around the guidewire 222 passing through the device 200, the tubular member 216 is moved from the inserted configuration to the retracted configuration while the guidewire 222 remains passing through the device 200. The resilience of the low pressure seal 206 causes the low pressure seal 206 to move from the open configuration to a sealing configuration sealing around the guidewire 222, as illustrated in FIGS. 7 to 10.

In this sealing configuration, the low pressure seal 206 effects a fluid tight seal around the guidewire 222 preventing blood loss. In this sealing configuration, it is possible to slide the guidewire 222 through the low pressure seal 206. This sealing configuration may typically be used during delivery of the guidewire 222 through the vasculature of a patient.

In further detail and with reference to FIG. 13 to disengage the plastic pin 236 from the profile slot 237, the cap 215 is pressed again, forcing the plastic cantilever arm 235 to flex downward inside the upper body housing 204 (Position D2 in FIG. 13, and FIGS. 34 to 37). When the cap 215 is released, the plastic pin 236 travels under the surface of the upper body housing 204 through the passage 238 (Position E in FIG. 13, and FIGS. 38 and 39) and coming to rest again at the position illustrated in FIGS. 14 to 18. The tubular member 216 is now in the retracted configuration with the low pressure seal 206 in the closed configuration.

The plastic pin 236 follows a unidirectional path as it travels through the actuation profile.

To effect the high pressure seal around the guidewire 222, the collet 209 is moved radially inwardly to move the high pressure seal 208 from the open configuration to the sealing configuration.

In further detail and with reference to FIGS. 8 to 10, the roto-lock nut 205 is rotated relative to the main body portion 210, which causes longitudinal movement of the roto-lock nut 205 relative to the main body portion 210, which in turns causes longitudinal movement of the housing 204 relative to the main body portion 210, which in turn causes longitudinal movement of the spacer 207 relative to the main body portion 210. As the spacer 207 moves longitudinally relative to the main body portion 210, the collet 209 is forced by the wedge action to compress radially inwardly to move the high pressure seal 208 from the open configuration to the sealing configuration (FIG. 10).

In this sealing configuration, the high pressure seal 208 effects a fluid-tight seal around the guidewire 222 preventing blood loss. In this sealing configuration, the high pressure seal 208 also locks the guidewire 222 in position preventing any sliding of the guidewire 222 relative to the device 200. This sealing configuration may typically be used after delivery of the guidewire 222 or a catheter has been completed, or when the clinician wishes to temporarily stop the interventional procedure.

To release the seal due to the high pressure seal 208 around the guidewire 222, the roto-lock nut 205 is rotated relative to the main body portion 210 in the opposite direction. The resilience incorporated into the design of the high pressure seal 208 moves the high pressure seal 208 from the sealing configuration (FIG. 10) to the open configuration (FIG. 8), and the self-biasing of the collet 209 moves the collet 208 from the sealing configuration (FIG. 10) to the open configuration (FIG. 8).

The guidewire 222 may be removed from the device 200 by sliding the guidewire 222 proximally through the low pressure seal 206 in the sealing configuration.

Figure 4:
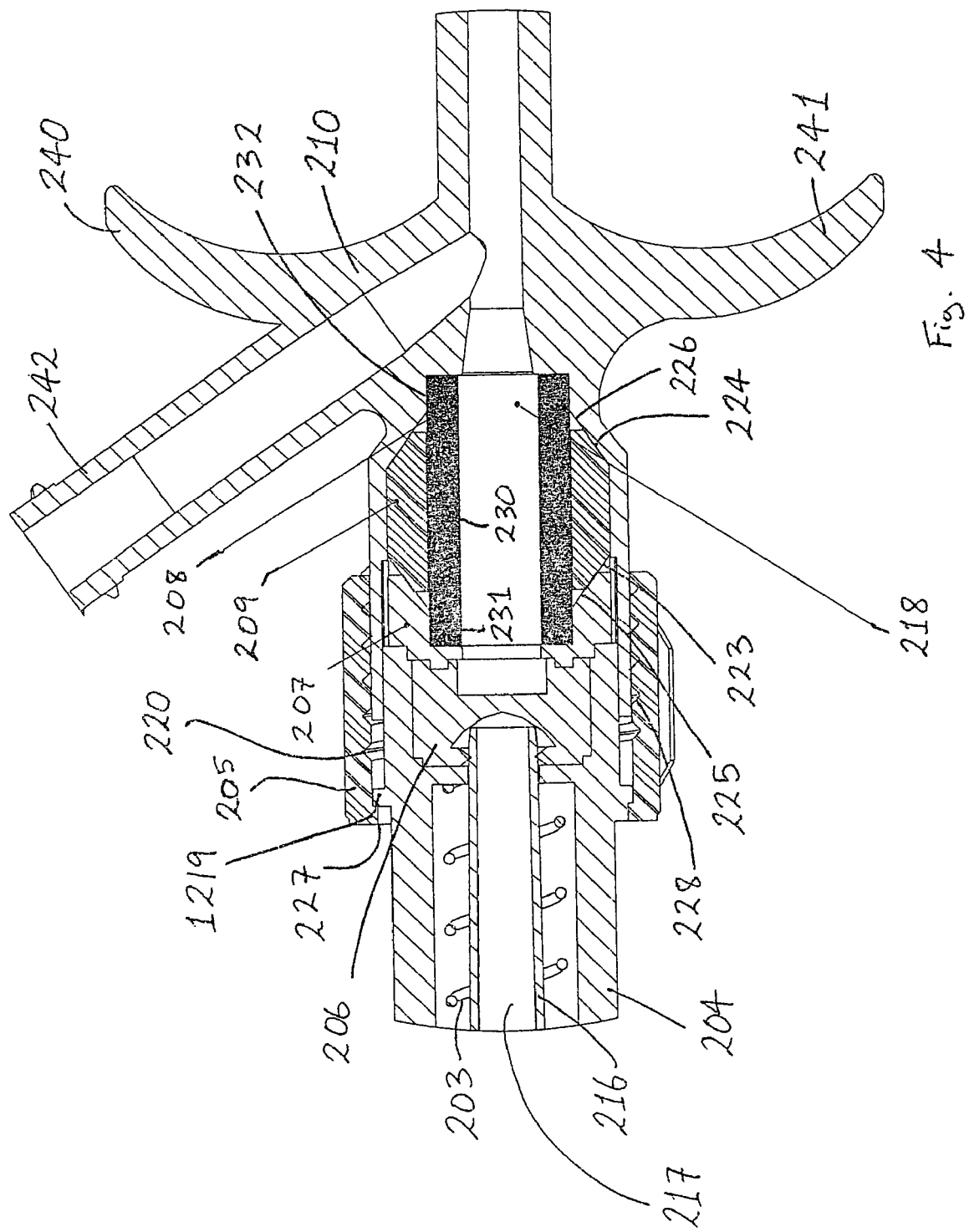
FIGS. 4 to 6 are enlarged, cross-sectional, side views of the device of FIG. 3, in use.
Figure 5:
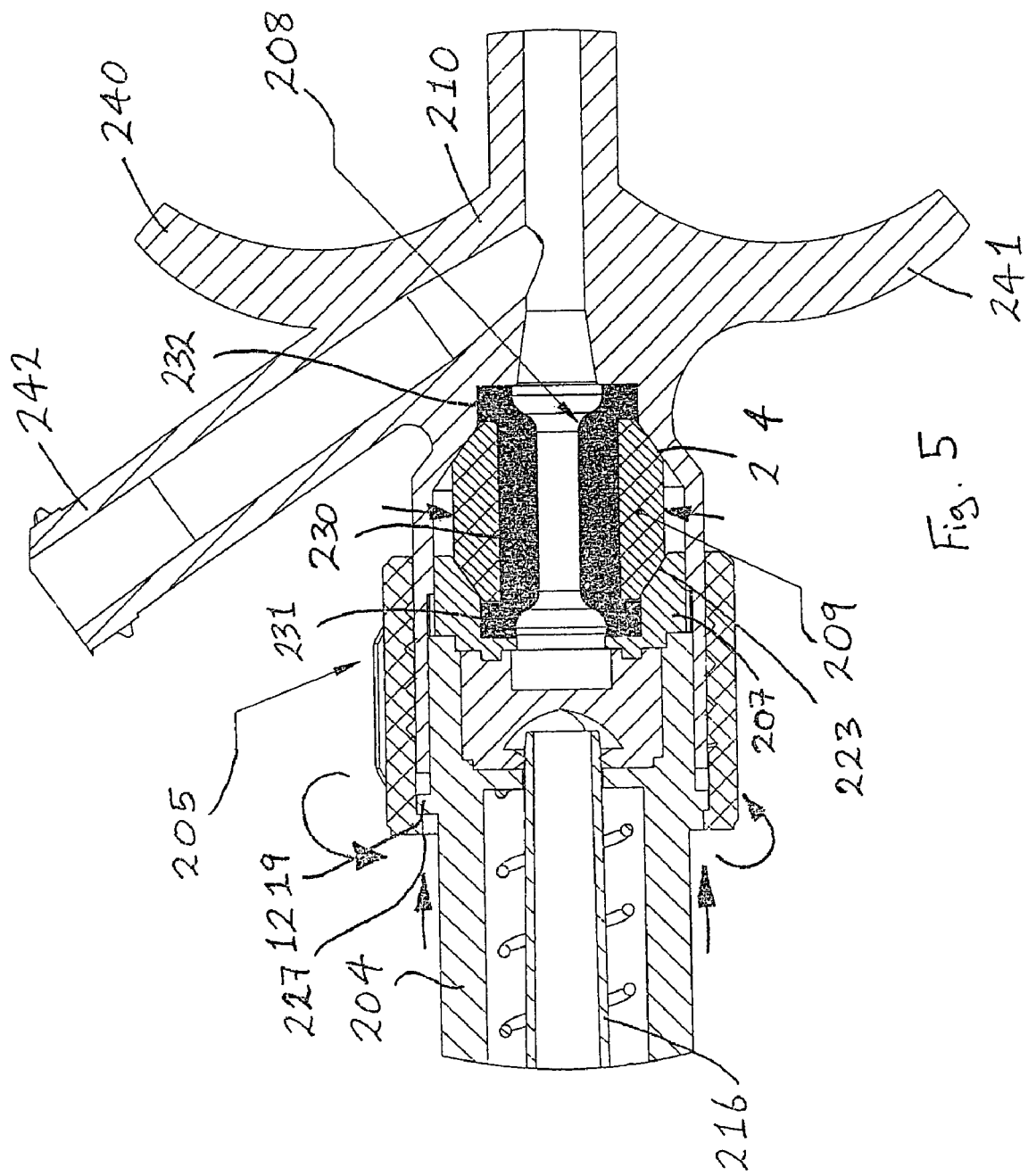

It will be appreciated that the high pressure seal 208 is also suitable for sealing down to close across the main body portion lumen 218 even when there is no guidewire or other medical device passing through the device 200, as illustrated in FIGS. 4 to 6.

There are a variety of possible applications for the collet 209 sealing/closing mechanism, which are not necessarily limited to haemostasis applications. For example, a possible application would be in the controlled restriction (constriction) of the inner lumen of a flexible tube, whereby the lumen can be progressively reduced in size down to fully closed and reversibly opened in a controlled process to fully opened. This closing/opening cycle can be performed many times with the device. The device may also have a graduated scale to show its stage of closure.

The collet mechanism may be combined with an automated motorised system to allow computer control of the metering device. Examples of such an application are in IV bag fluid dose management, tube feeding systems, metered fluid delivery systems such as the Patient Controlled Analgesia (PCA) pump for patient medication, and aerosol based medication systems.

Another possible application of the collet mechanism is as a gripper where it closes down securely onto a shaft. Examples of such an application would be as a guidewire torquer device.

Figure 48:
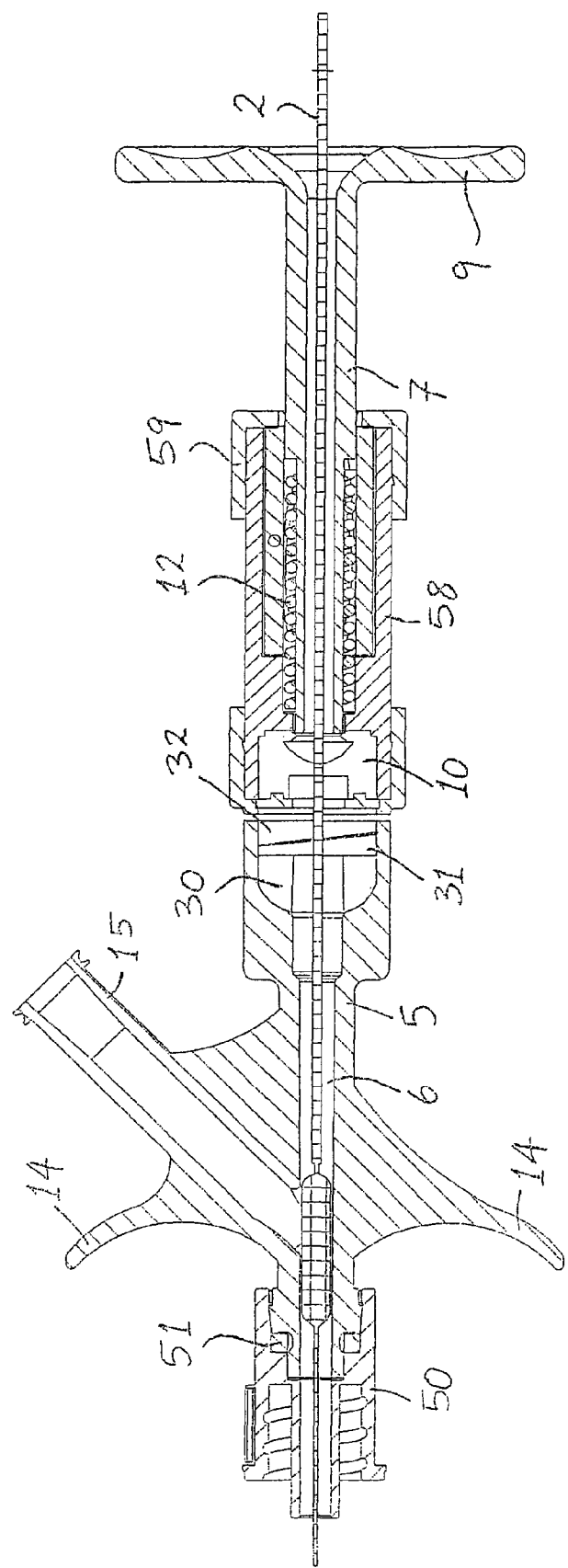
FIG. 48 is a cross sectional view of the device with the plunger extended with the cams closed and a guidewire in position.
Figure 49:
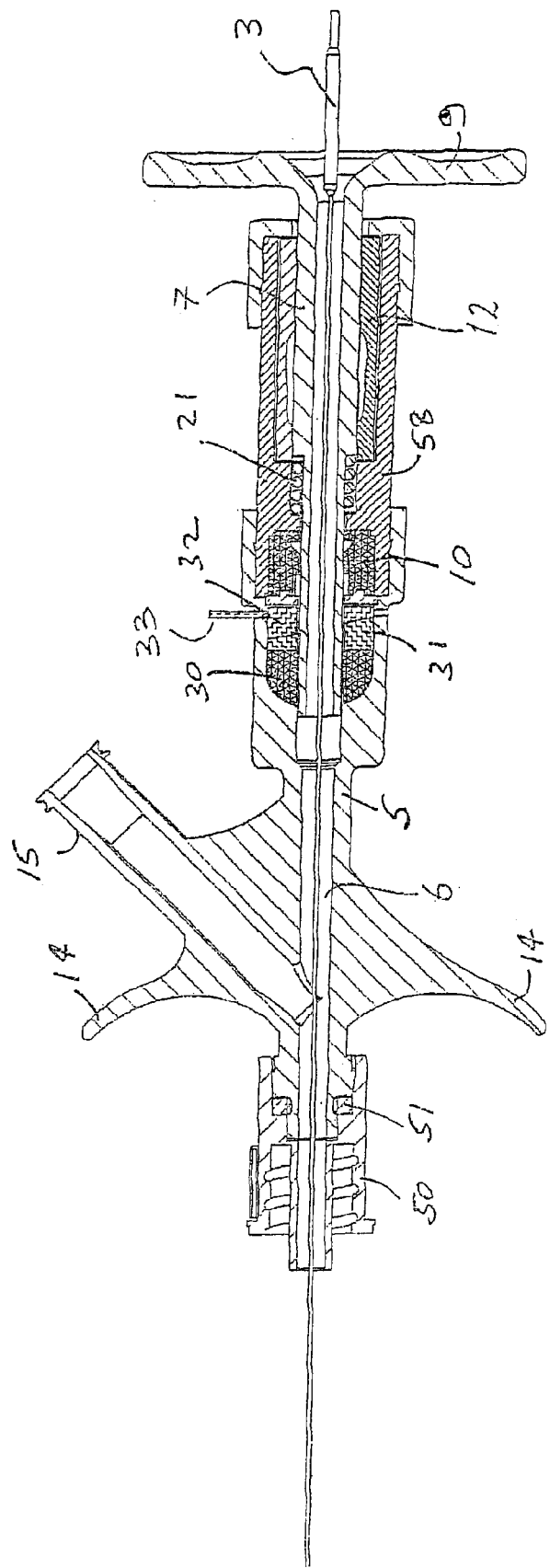
FIG. 49 is a cross sectional view of the device with the plunger depressed, the cams closed and a guidewire in place and a balloon catheter being introduced.
Figure 50:
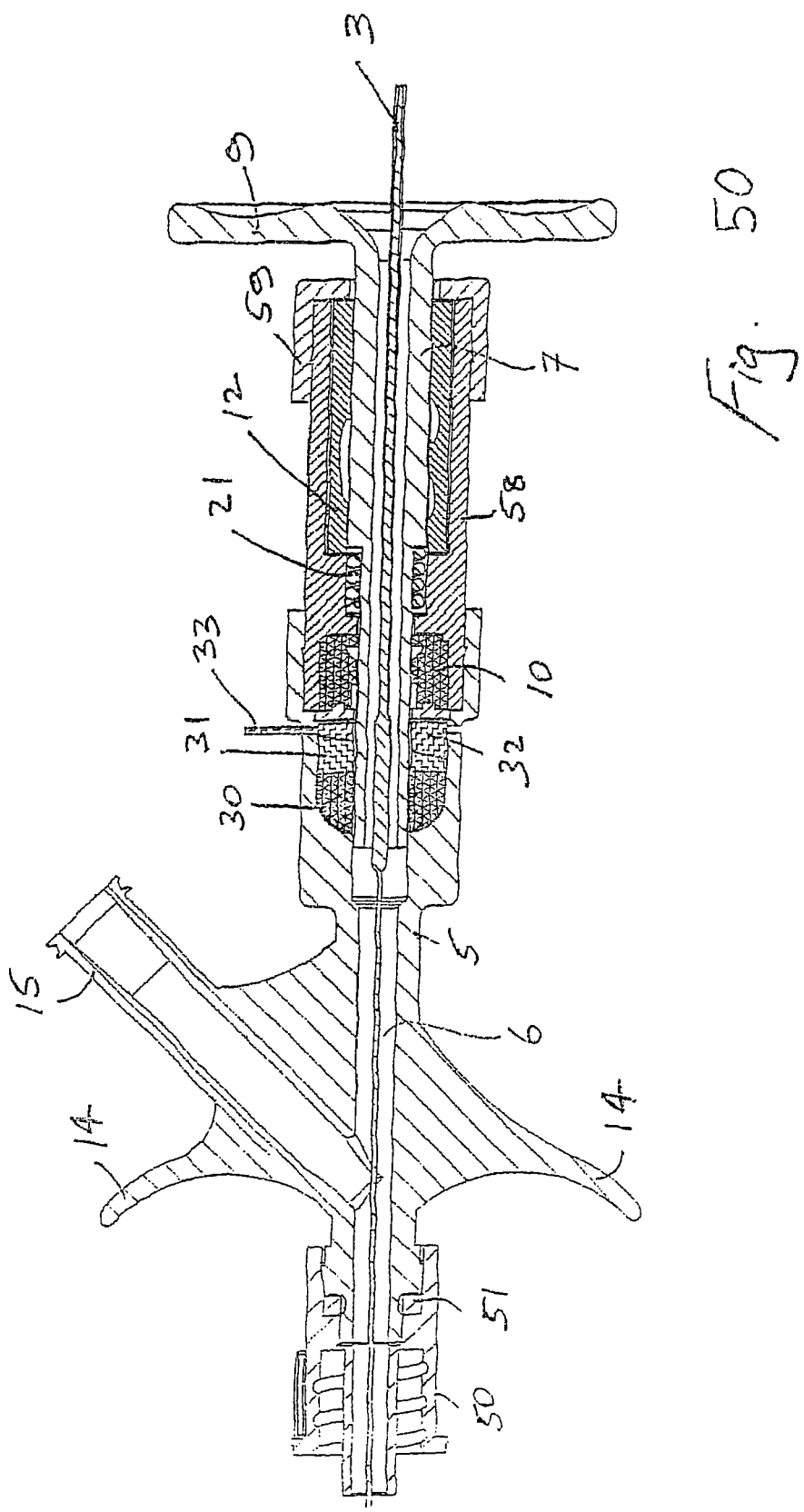
FIG. 50 is a cross sectional view of the device in the configuration of FIG. 49 with the plunger still depressed and the balloon catheter further advanced through the device.
Figure 51:
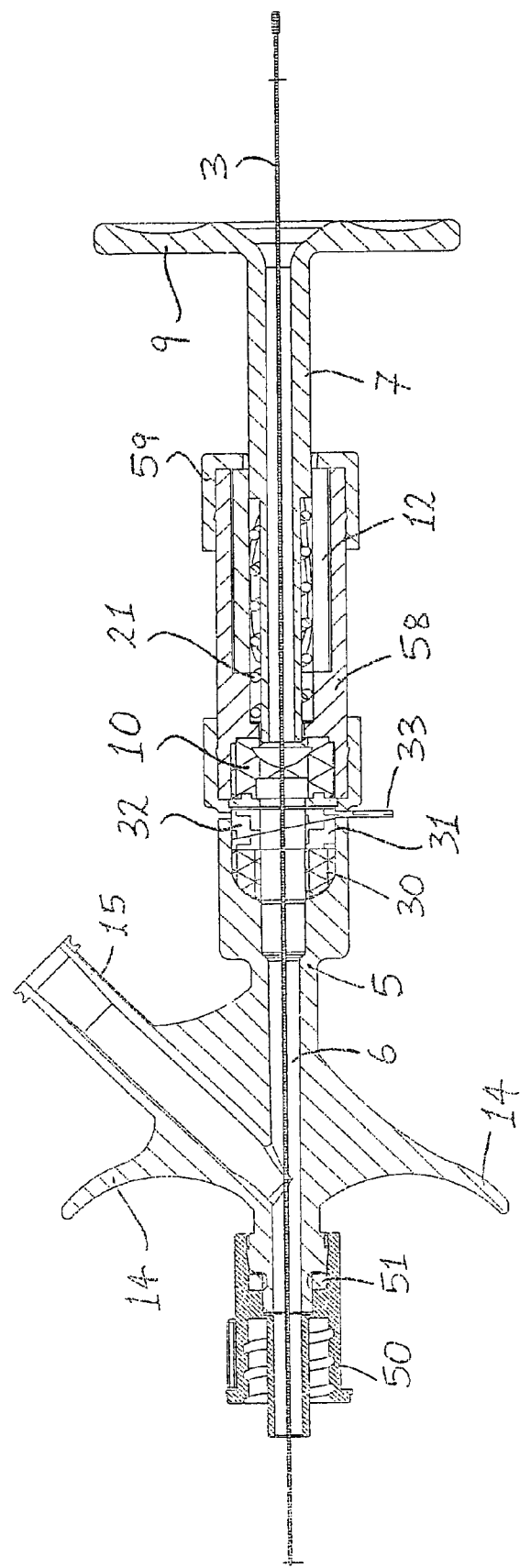
FIG. 51 is a cross sectional view of the device with the plunger extended and a balloon catheter exiting the device.
Figure 52:
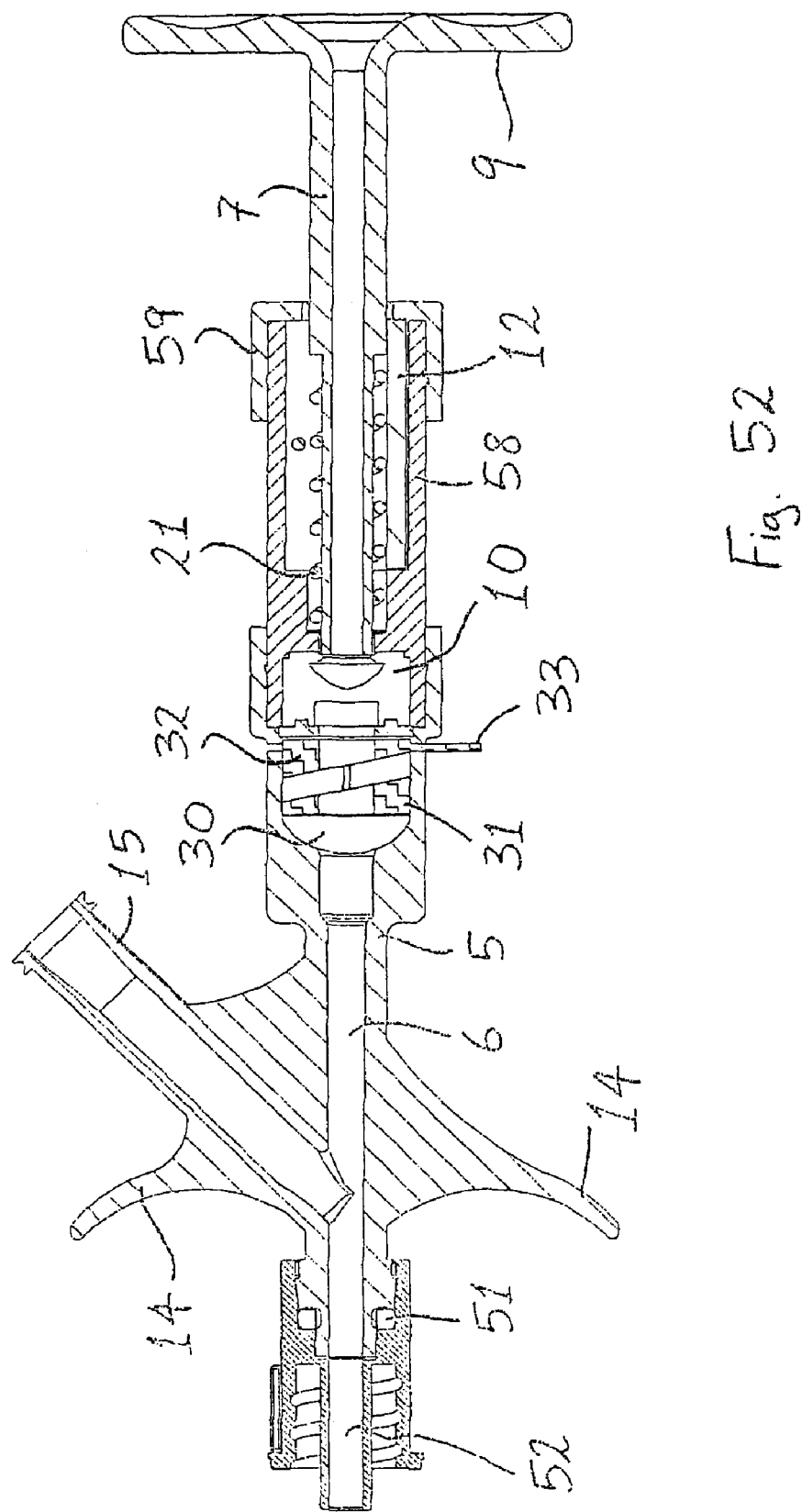
FIG. 52 is a cross sectional view of the device with the plunger extended and the cams open.
Figure 53:
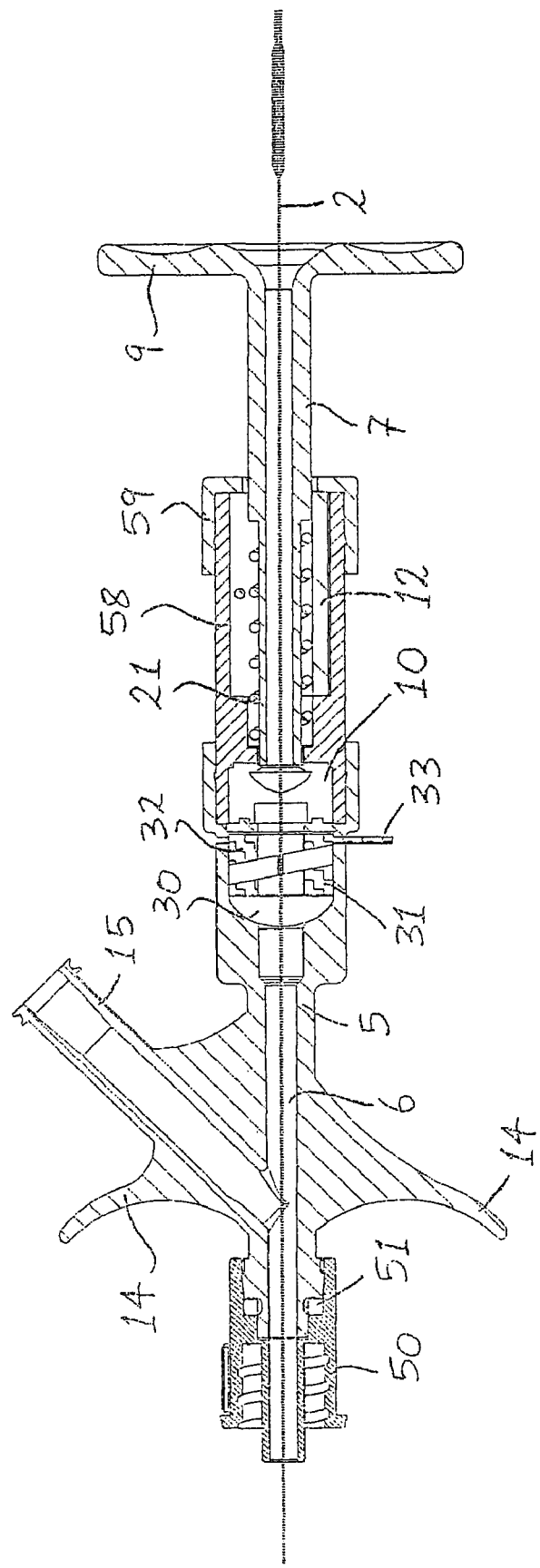
FIG. 53 is a cross sectional view of the device with the plunger extended and the cams open with a guidewire in place.
Figure 54:
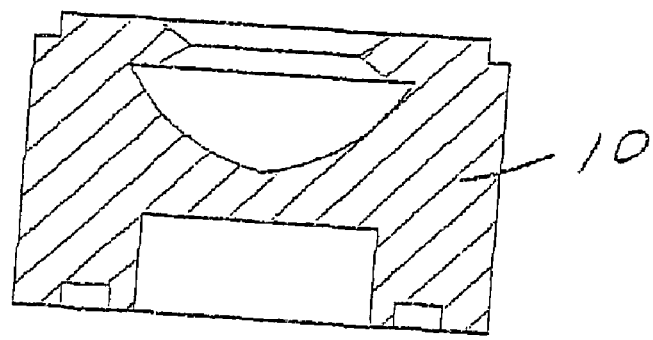
FIG. 54 is a cross sectional view on an enlarged scale of a low pressure seal of the device.
Figure 55:
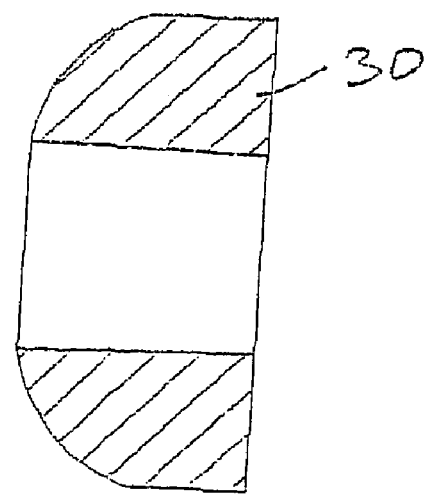
FIG. 55 is a cross sectional view on an enlarged scale of a high pressure seal of the device.
Figure 58:
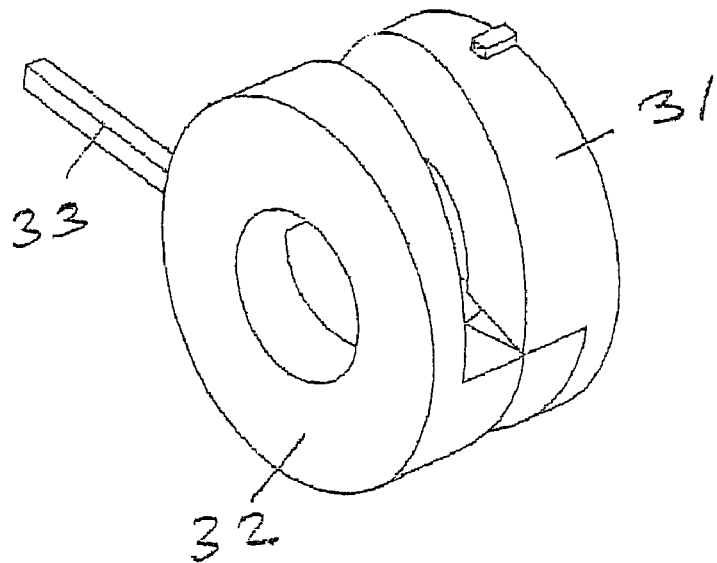
FIG. 58 is a perspective view of the cams of FIGS. 56 and 57 assembled in an open configuration.
Figure 59:
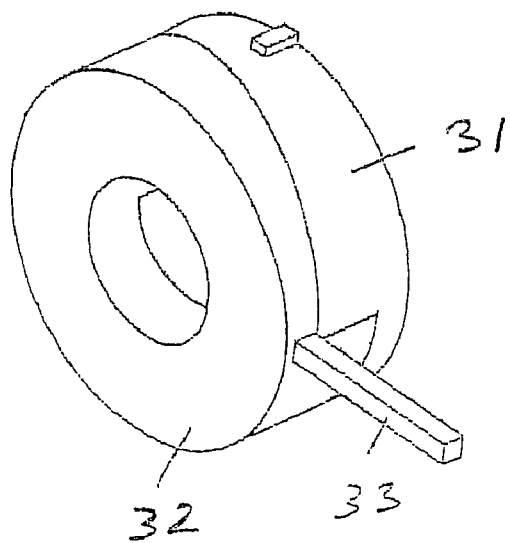
FIG. 59 is a perspective view of the cams assembled in a closed configuration.
Figure 60A:
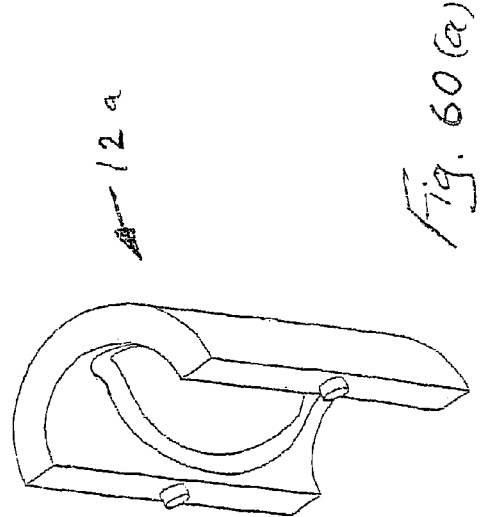
FIGS. 60(a) to 60(d) are views of one half of a shuttle of the device.
Figure 60D:
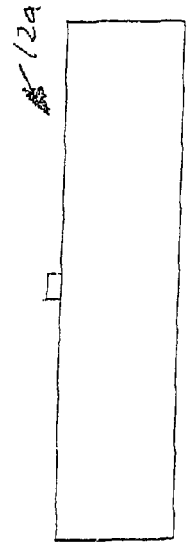
Figure 60B:
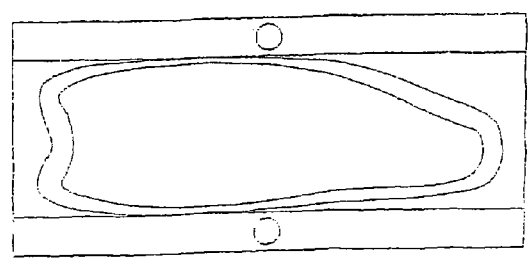
Figure 60C:
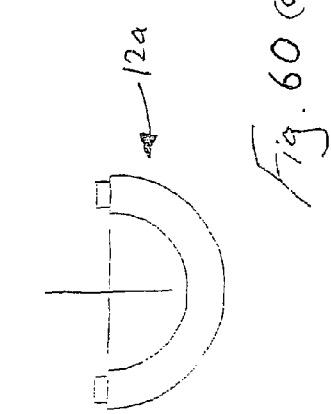
Figure 62C:
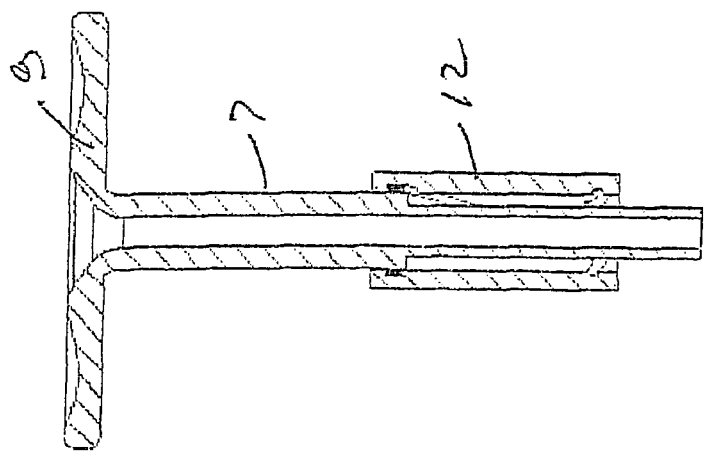
FIGS. 62(a) to 62(c) are cross sectional views illustrating the movement of the plunger relative to the assembled shuttle (in reverse order)
Figure 62B:
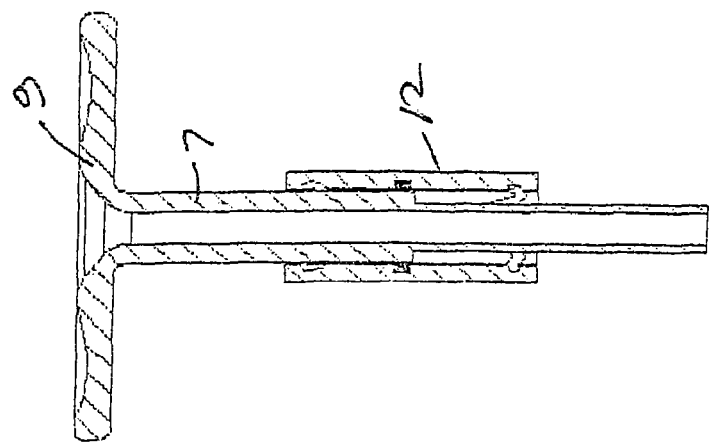
Figure 62A:
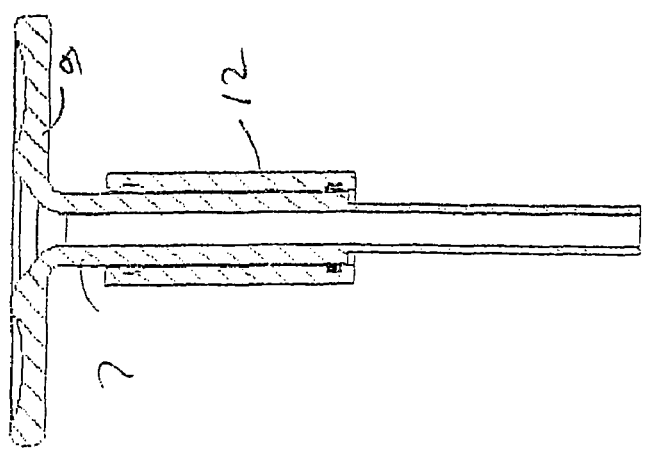
Figure 63A:
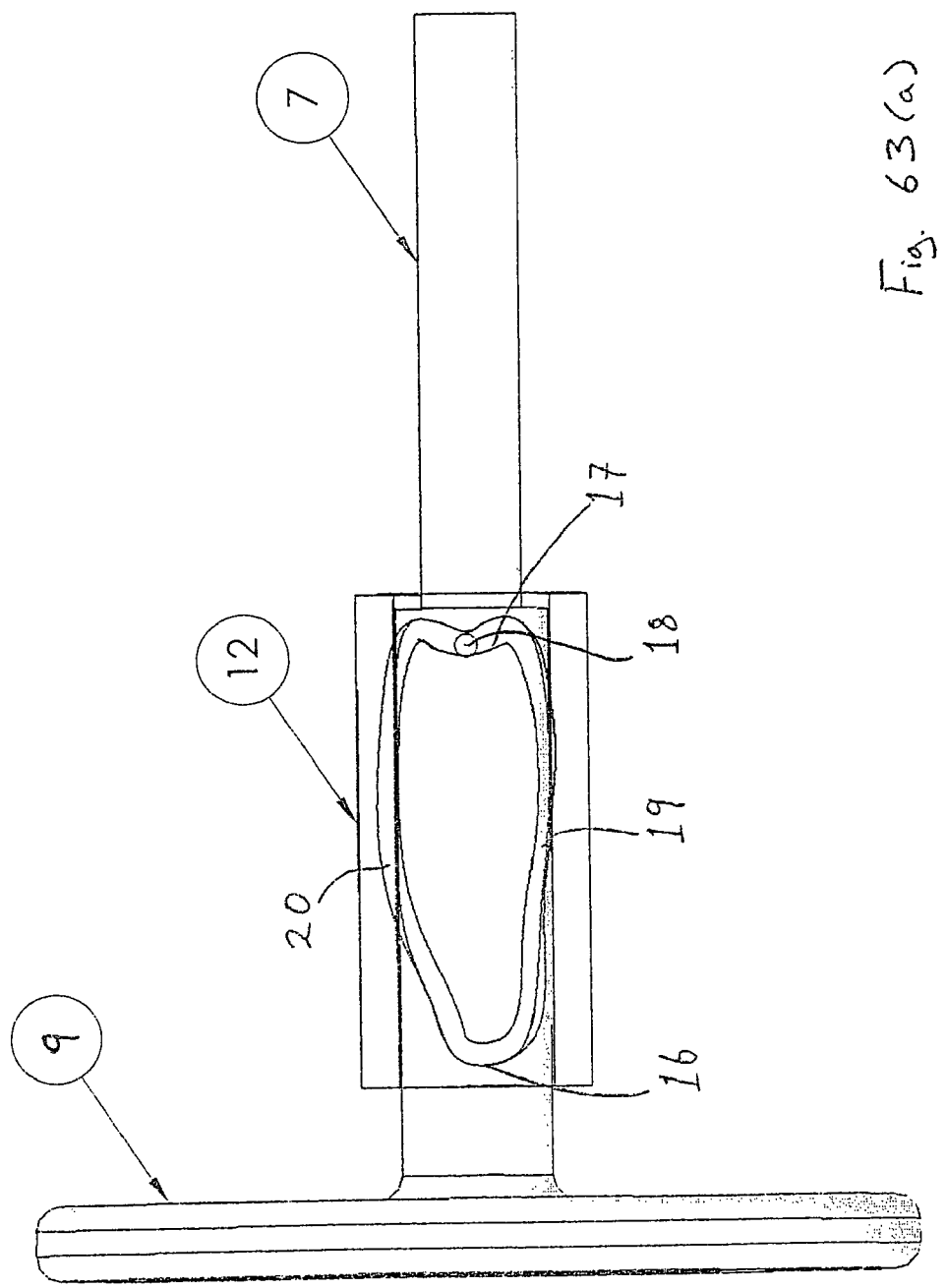
Figure 63B:
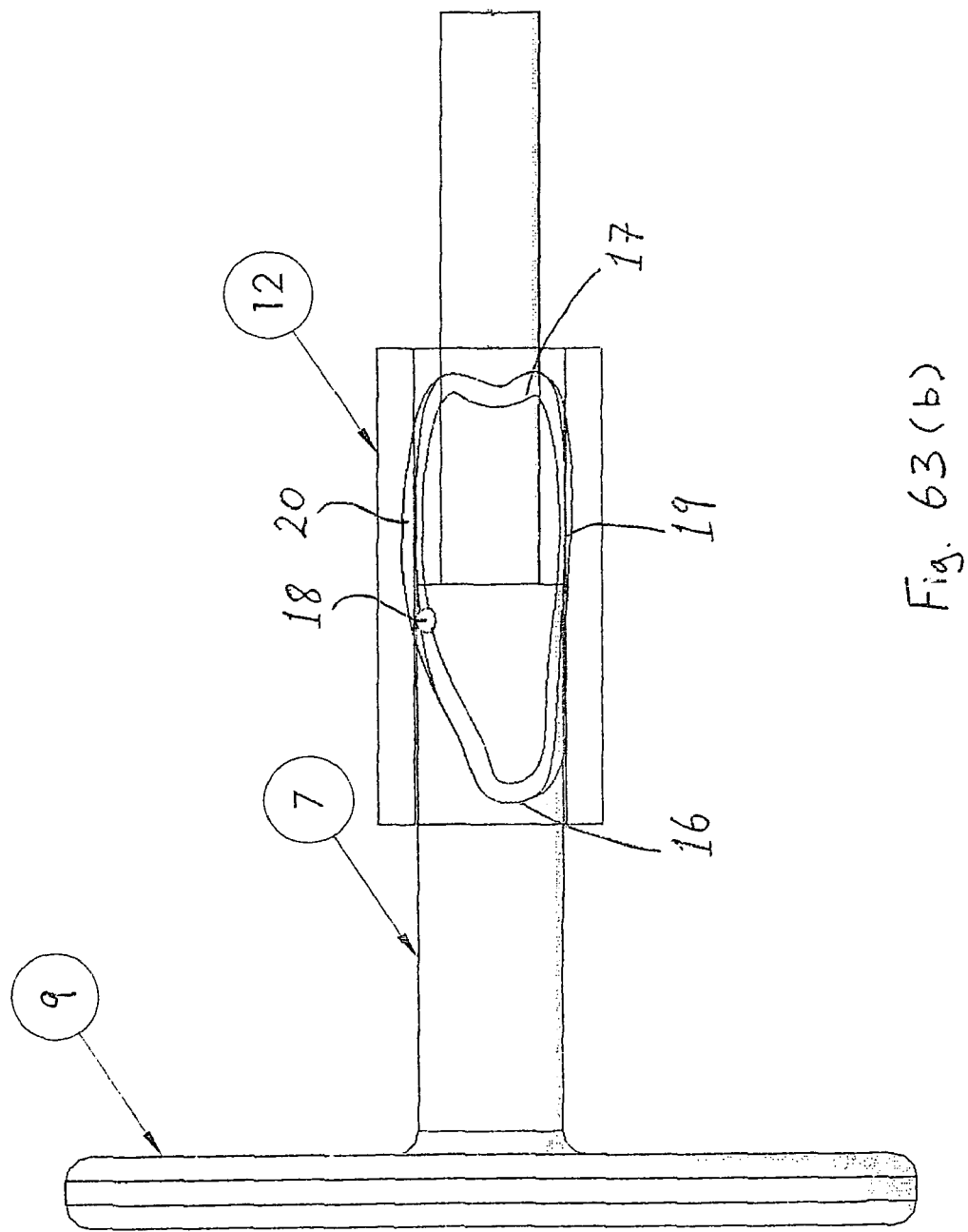
Figure 70:
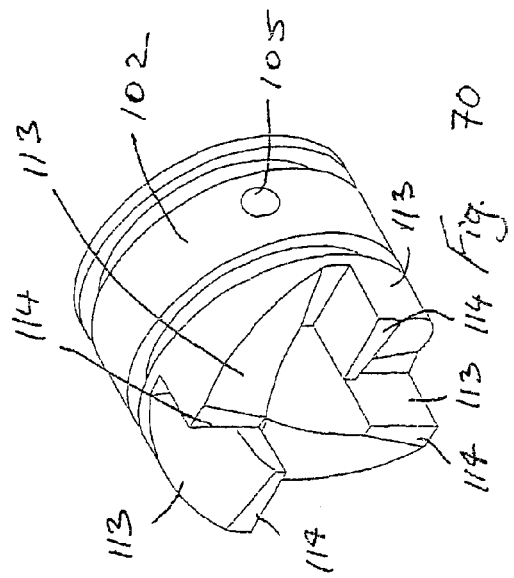
FIGS. 70 to 73 are views of an upper cam of the cam system of FIG. 65.
Figure 71:
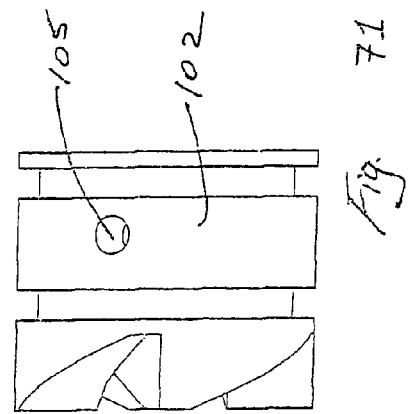
Figure 72:
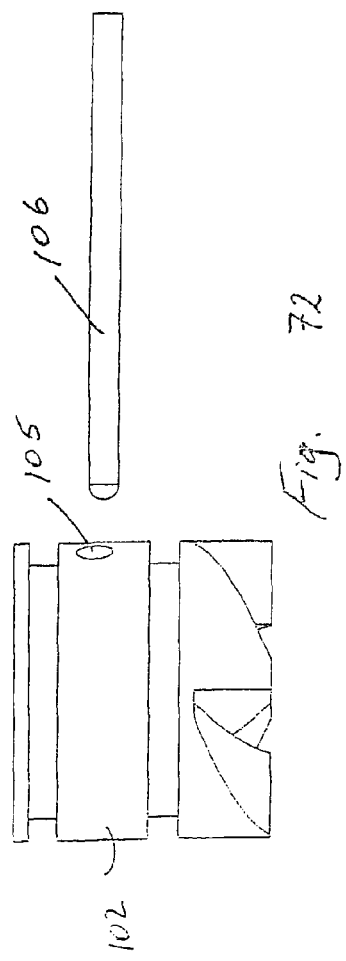
Figure 73:
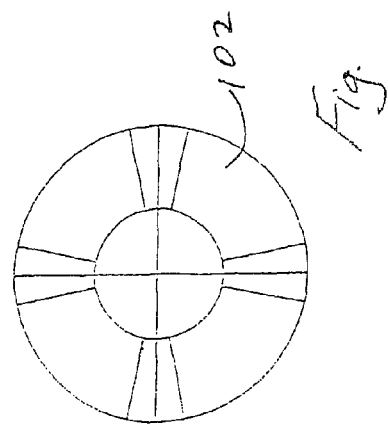

Referring to FIGS. 40 to 64(g), there is illustrated another medical device 1 for providing haemostasis whilst facilitating introduction of an elongate member such as a guidewire 2 (FIG. 48) and/or a catheter such as a balloon catheter 3 (FIG. 50) into a patient's vasculature.

Figure 46:
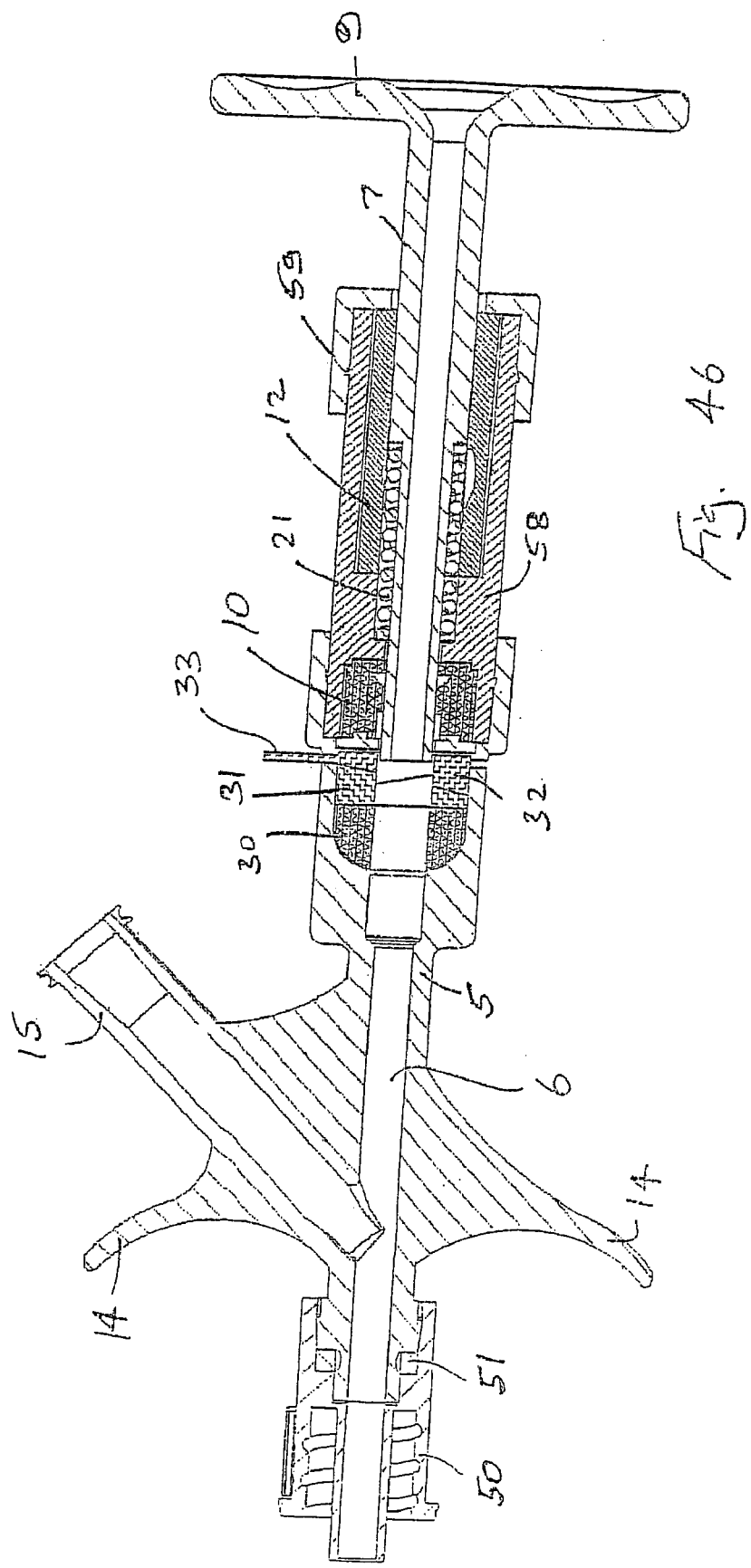
FIG. 46 is a cross sectional view of the device with the plunger partially depressed and the high pressure seal open.
Figure 47:
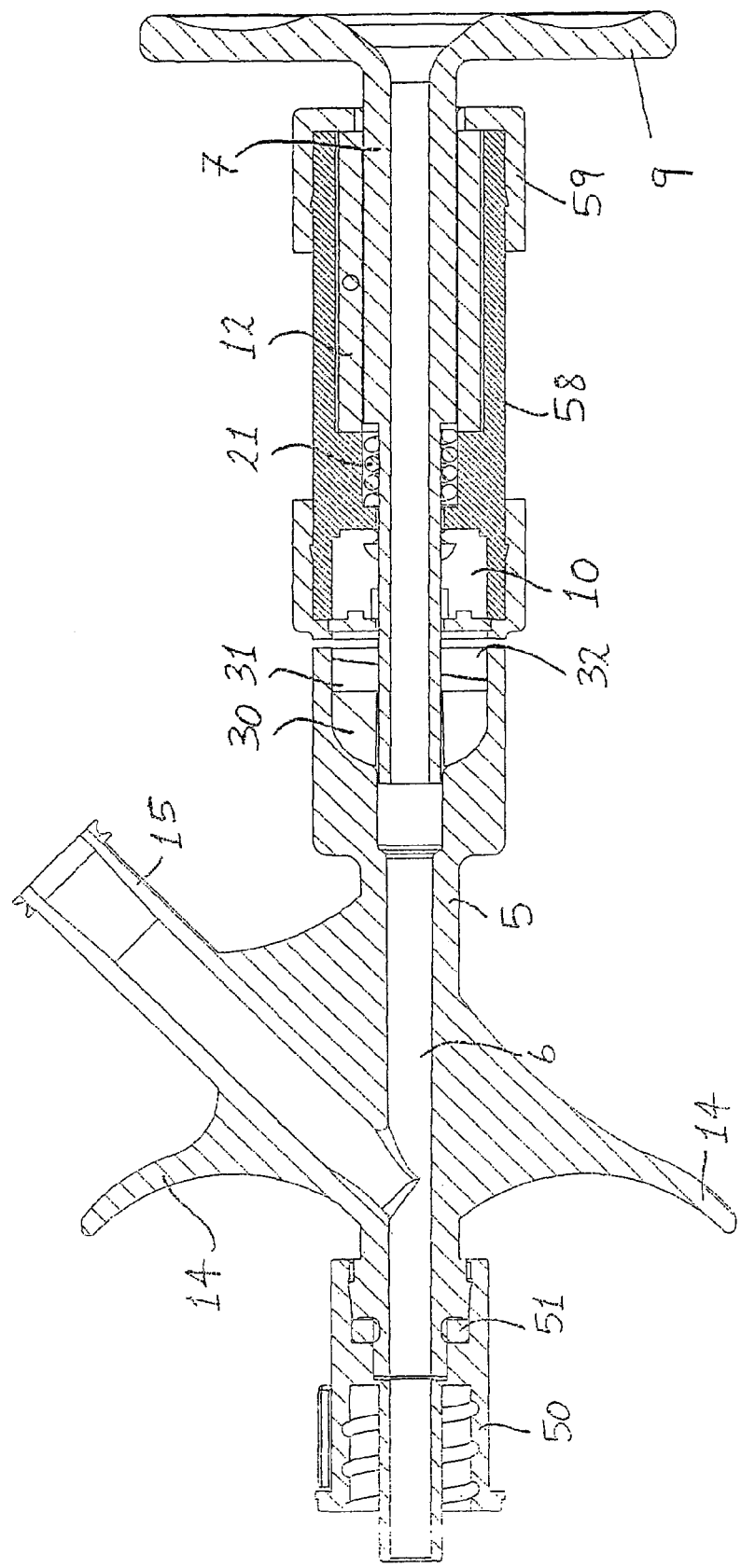
FIG. 47 is a cross sectional view of the device with the plunger fully depressed and the high pressure seal open.

The device 1 comprises a main body member 5 having a lumen 6 extending therethrough for passage of the elongate member. The device 1 also comprises a plunger 7 having a plunger lumen 8 extending therethrough, the plunger lumen 8 being in alignment with the lumen 6 in the main body member 5. The plunger 7 has a proximal head piece 9 which is engagable by a user's thumb. A low pressure seal 10 is provided between the main body member 5 and the plunger 7. The plunger 7 is movable relative to the main body member 5 from a first position in which the low pressure seal 10 is closed (FIG. 45) to a second position in which the low pressure seal 10 is open and the lumen 6 of the main body member 5 is in communication with the plunger lumen 8 (FIG. 46).

The main body member 5 has two oppositely directed integral finger grips 14 which a clinician grips during operation of the device 1, whilst actuating the plunger 7 by engaging the proximal headpiece 9 with a thumb. The main body member 5 also has a side port 15 communicating with the lumen 6 of the main body member 5. The side port 15 may be either a male luer lock or tubing with a connecting luer lock to attach syringes and/or pumps for injection of a fluid, such as a contrast medium.

The movement of the plunger 7 is controlled by a shuttle 12 which in this case is formed by two generally half cylinder shaped shuttle parts 12a (FIGS. 60(a) to 60(d)), 12b (FIGS. 61(a) to 61(d)) which are mated together, on assembly. Referring in particular to FIGS. 60(a) through 64(g), the shuttle 12 has in this case two locators formed by regions 16, 17 in which lugs 18 on the plunger 7 are retained. These rest or retained regions 16, 17 are particularly illustrated in FIGS. 64(a) and 63(c) in the case of region 16, and in FIGS. 63(a) and 64(d) in the case of region 17. The locators are joined by channels or pathways 19, 20 along which the lugs 18 travel as the plunger 7 is moved. The shuttle 12 and plunger 7 act in combination with a coil spring 21 to control the movement of the plunger 7 as it is operated by the user.

Referring in particular to FIGS. 64(a) to 64(g) the following will be apparent:

Shuttle Mechanism Actuation

The sequence below describes the movement of the lugs 18 through the channels 19, 20 in the shuttle mechanism. It is shown in 2-D for clarity.

Shuttle Mechanism Actuation (Description of Lug Travel Through Channel)

| Lug Position | Movement Driver | Action/Direction | Comment |
|---|---|---|---|
| 64(a) | Resting | No movement. | Starting location of lug 18 |
| 64(a) to 64(b) | User | Downward pressure/ vertical on plunger 7. | Lug 18 moves down through shuttle channel 20. Spring 21 being compressed. |
| 64(b) to 64(c) | User | Downward pressure/ vertical on plunger 7. | Lug 18 continues to bottom of shuttle channel 20. Spring 21 compression at maximum. |
| 64(c) to 64(d) | Spring 21 | Upward pressure/ vertical on plunger 7. | Upward force from compressed spring 21 pushes lug 18 through channel 20 into locator region 17. |
| 64(d) to 64(e) | User | Downward pressure/ vertical on plunger 7. | Lug 18 moves down shuttle channel 19 to position 64(e). Spring 21 being compressed. |
| 64(e) to 64(f) | Spring 21 | Upward pressure/ vertical on plunger 7. | Upward force from compressed spring 21 pushes lug 18 through channel 19 into position 64(f). |
| 64(f) to 64(g) | Spring 21 | Upward pressure/ vertical on plunger 7. | Upward force from compressed spring 21 continues to push lug 18 upward through channel 19 into locator region 16: |

The device 1 has a high pressure seal 30 between the plunger 7 and the main body 5. In this case the high pressure seal 30 is provided in the form of a locking valve seal. The locking seal 30 is movable from a closed sealing position (FIG. 52) to an open position (FIG. 51) by a user activated operator. In this case the operator for the seal 30 comprises a pair of camming members 31, 32 which are movable relative to one another to open and close the locking seal 30. One of the camming members 32 has an attached handle 33 for rotating the cam 32 and hence the cam 31 to positively open the locking seal 30. The handle position acts as an indicator of the open or closed configuration of the locking seal 30. For insertion of an elongate member through the device 1, the locking seal 30 is opened. In some cases it is desirable to inject a contrast medium or other fluid through the side port 15. In this case the locking valve 30 is closed by turning the handle 33 to prevent leakage through the system, on injection.

Other features of the device 1 include a rotating Luer lock 50 for use in attaching to a guide catheter which is attached to the main body member 5 at the distal end with an o-ring seal 51 being interposed therebetween. A spacer 55 is located between the low pressure seal 10 and the cam 32. The low pressure seal 10, shuttle 12, spring 21 and plunger 7 are housed in a proximal body 58 fitted with a cap 59.

The means to open and close the low pressure seal 10 is easy to use, ergonomic and allows a clinician to deploy single handedly. The means to open and close the locking valve seal 30 is easy to use and clearly shows open and closed positions.

The low pressure seal 10 uses a mechanism which is easy-to-use, intuitive and readily operable single-handedly. Moreover, there is a distinct time saving for the physician, particularly over the course of a number of procedures. The mechanism does not require stiff guidewires to be introduced in this way, as its smaller diameter should allow it to pass easily through seal 10 (assuming seal 30 is open). Flexible tip guidewires will require seal 10 to be opened for introduction and this can be readily accomplished using the described mechanism. Seal 30 is default open for >98% of cases. The cam-operation allows it to be readily turned into a closed-seal position.

Referring to FIGS. 65 to 73 there is illustrated an alternative cam system 100 for the device 1 described above. The cam system 100 comprises an upper cam 102 and a lower cam 101. The larger upper cam 102 accommodates a bearing and sealing ring system to facilitate rotational movement of the locking seal 30 and better haemostasis. It also has a slot 105 to accommodate a lever 106 for rotating the upper cam 102.

The lower cam 101 has lugs 107 which fit into slots in the main body member 5 and restrict rotational motion.

The lower cam 101 has four projecting teeth 110 with flattened regions 112. The upper cam 102 also has four teeth 113 with flattened regions 114.

This four tooth cam design provides locking seal compression (open-to-closed) by rotating the upper cam 102 through approximately 90 degrees.

The flat tops 112, 114 on the upper and lower cam teeth 110, 113 provide a holding platform for the cams 101, 102 when they are opened with the seal 30 compressed.

When the plunger mechanism of the invention is deployed, the plunger 7 is either down or up, i.e. no half-open positions are possible. Moreover, due to the actuation mechanism, it is easily distinguishable to the physician whether the mechanism is in the up or down position. Ease of open/close mechanism by use of single-handed operation will facilitate physicians' closure of valves to ensure that patients' blood loss is minimised.

In addition, because half-open/half-closed positions are not possible the risk of stents being damaged by being dragged through half-open seals is minimised.

The cap and tube mechanism of the device will allow a tube to pass through both seals 10, 30, thereby ensuring there is no direct contact between the stent and either of the seals 10, 30 at any time during introduction through the valve inner lumen. Thus, there is no risk of value-added stent coatings being scraped-off when being delivered through the seals 10, 30 to the patient's vasculature.

The interlinking of cap design/finger rests provides comfortable "syringe-style" operation for a physician. The device includes two finger rests 14. Moreover, the cap has a generous ledge, which facilitates gripping by the user when required.

In FIGS. 74 to 77 there is illustrated an alternative mechanism 300 for selectively opening the low pressure seal 206. The mechanism is suitable for use with a haemostasis device similar to the device 200 described previously with reference to FIGS. 1 to 39.

Instead of employing the arrangement of the bayonet 201 and the housing 204 with the slot 237 and the pin 236, the mechanism 300 comprises a tubular member 301 and a housing 302.

The tubular member 301 comprises a leaf-spring cantilever arm 303 with an upstanding finger 304 at the free end of the cantilever arm 303.

Two openings 305, 306 are provided in the wall of the housing 302 corresponding to the retracted and inserted configurations of the tubular member 301 respectively.

Figure 75:
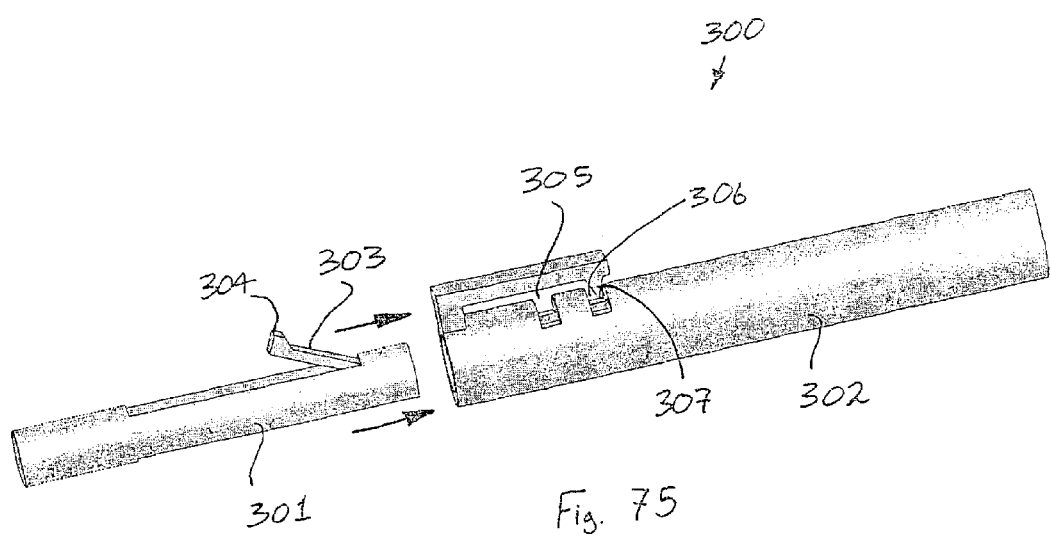
FIG. 75 is a perspective view illustrating assembly of the two parts of FIG. 74.

To assemble the mechanism 300, the tubular member 301 is inserted into the housing 302 (FIG. 75). When the finger 304 reaches the first opening 305, the leaf-spring nature of the arm 303 forces the finger 304 radially outwardly to engage the first opening 305. The tubular member 301 is thus held in the retracted configuration with the low pressure seal 206 in the closed configuration.

Figure 76:
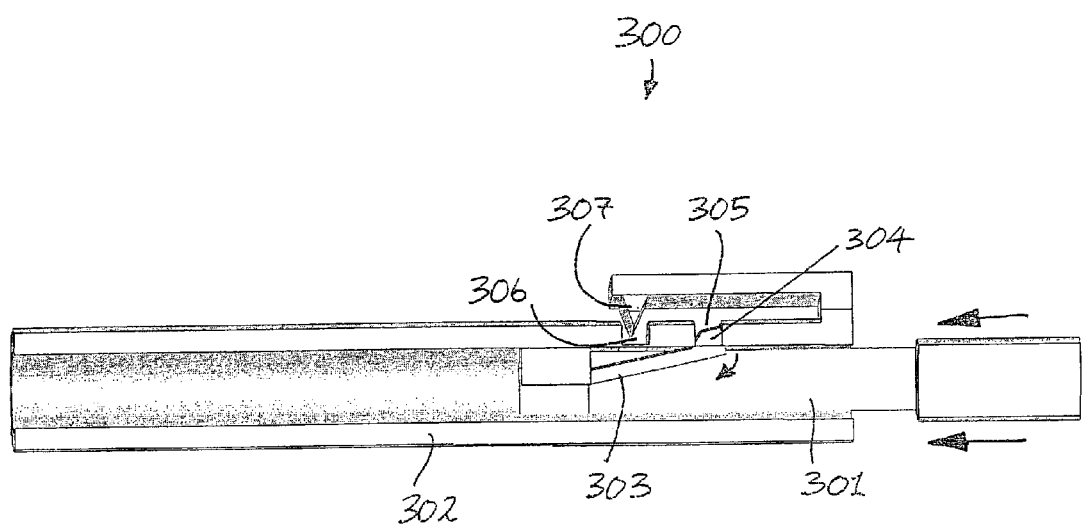
FIGS. 76 and 77 are cross-sectional, side views of the two parts of FIG. 74, in use.

To move the tubular member 301 from the retracted configuration to the inserted configuration, and thus move the low pressure seal 206 from the closed configuration to the open configuration, the tubular member 301 is pushed distally forcing the finger 304 radially inwardly (FIG. 76). When the finger 304 reaches the second opening 306, the leaf-spring nature of the arm 303 forces the finger 304 radially outwardly to engage in the second opening 306. The tubular member 301 is thus held in the inserted configuration with the low pressure seal 206 in the open configuration.

Figure 77:
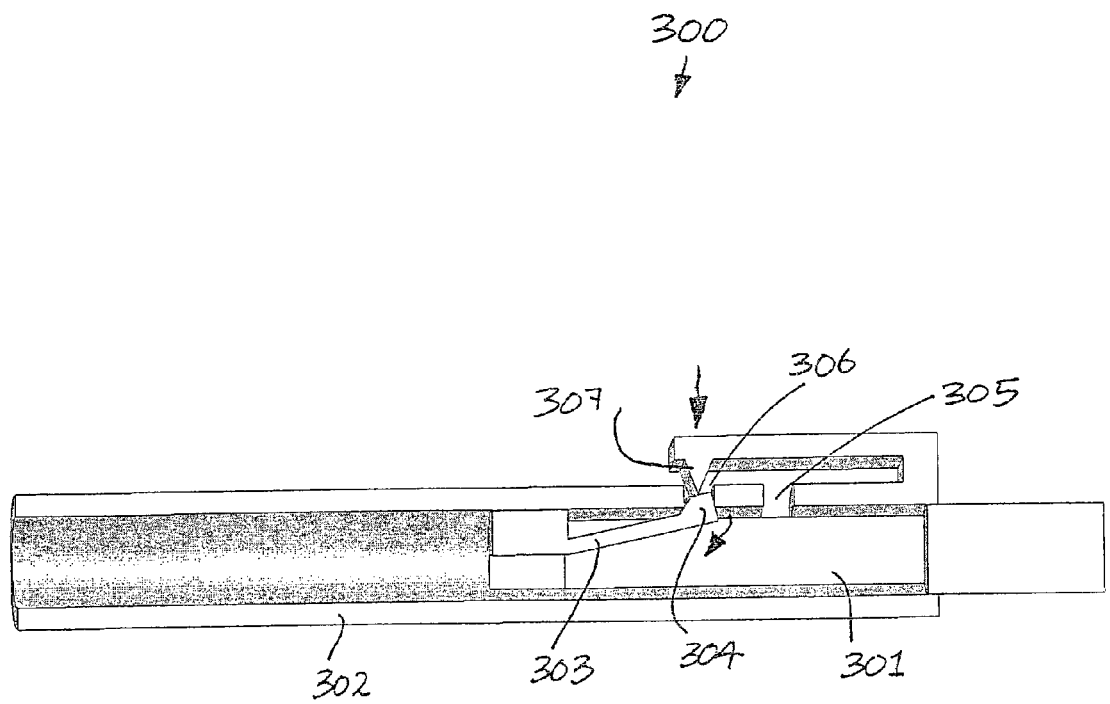

To move the tubular member 301 from the inserted configuration to the retracted configuration, the finger 304 is forced radially inwardly using a pointed tool 307 supported on the housing 302 (FIG. 77). The tubular member 301 is thus released and free to move proximally to the retracted configuration under the biasing force of the coiled spring 203.

The invention is not limited to the embodiments hereinbefore described, with reference to the accompanying drawings, which may be varied in construction and detail.

The invention claimed is:

1. A haemostasis device comprising:
a housing defining a lumen extending therethrough;
a first seal having a closed configuration to seal across the lumen, and an open configuration to facilitate passage of a medical device through the lumen;
a second seal having an open configuration to facilitate passage of the medical device through the lumen, and a sealing configuration to seal around the medical device passing through the lumen;
a tubular member selectively moveable between a retracted configuration and an inserted configuration for movement of the first seal between the closed configuration and the open configuration, the tubular member extending through both the first seal and the second seal with a distal end of the tubular member extending distally of the second seal in the inserted configuration; and
a first guide path and a second guide path,
the tubular member having a guide element movable along the first guide path upon movement of the tubular member from the retracted configuration to the inserted configuration, and movable along the second guide path upon movement of the tubular member from the inserted configuration to the retracted configuration.

2. A device as claimed in claim 1 wherein the first guide path is offset from the second guide path.

3. A device as claimed in claim 2 wherein the first guide path is circumferentially offset from the second guide path.

4. A device as claimed in claim 2 wherein the first guide path is radially offset from the second guide path.

5. A device as claimed in claim 1 wherein the housing defines at least one of the guide paths.

6. A device as claimed in claim 5 wherein at least one of the guide paths comprises a slot in a wall of the housing.

7. A device as claimed in claim 6 wherein the first guide path comprises a slot in a wall of the housing.

8. A device as claimed in claim 5 wherein at least one of the guide paths comprises a passage radially inwardly of a wall of the housing.

9. A device as claimed in claim 8 wherein the second guide path comprises a passage radially inwardly of a wall of the housing.

10. A device as claimed in claim 1 wherein the guide element is carried by the tubular member.

11. A device as claimed in claim 10 wherein at least part of the guide element is movable relative to the tubular member.

12. A device as claimed in claim 11 wherein the guide element includes a cantilever arm element.

13. A device of claim 12 wherein at least part of the cantilever element is movable relative to the tubular member in a radial direction.

14. A device as claimed in claim 12 wherein at least part of the cantilever arm element is movable relative to the tubular member in a circumferential direction.

15. A device as claimed in claim 1 wherein the device comprises a shield extending over the guide element.

16. A device as claimed in claim 15 wherein the shield is provided radially outwardly of the guide element.

17. A device as claimed in claim 1 wherein the tubular member includes a finger grip configured to be engaged by a finger of a user.

18. A device as claimed in claim 1 wherein the tubular member is biased towards the retracted configuration.

19. A device as claimed in claim 1 wherein the tubular member is movable through the first seal to move the first seal from the closed configuration to the open configuration.

20. A device as claimed in claim 1 wherein the tubular member defines a lumen extending therethrough aligned with the lumen of the housing.

21. A device as claimed in claim 1 wherein the first seal is biased towards the closed configuration.

22. A device as claimed in claim 1 wherein the first seal is a low pressure seal.

23. The haemostasis device according to claim 1, further comprising:
a collar member selectively moveable in a substantially radial direction for movement of the second seal between the open configuration and the sealing configuration.

24. A device as claimed in claim 23 wherein the device comprises an actuator member engagable with the collar member to selectively move the collar member in a substantially radial direction.

25. A device as claimed in claim 24 wherein the actuator member is movable longitudinally relative to the housing to selectively move the collar member in a substantially radial direction.

26. A device as claimed in claim 25 wherein at least part of the actuator member is rotatable relative to the housing to move the actuator member longitudinally relative to the housing.

27. A device as claimed in claim 24 wherein the actuator member is slidably engagable with the collar member to selectively move the collar member in a substantially radial direction.

28. A device as claimed in claim 27 wherein the actuator member includes a first wedge surface and the collar member includes a second wedge surface, and the first wedge surface of the actuator member is engagable with the second wedge surface of the collar member to selectively move the collar member in a substantially radial direction.

29. A device as claimed in claim 28 wherein the first wedge surface is slidably engagable with the second wedge surface.

30. A device as claimed in claim 23 wherein the housing is engagable with the collar member to selectively move the collar member in a substantially radial direction.

31. A device as claimed in claim 30 wherein the housing is slidably engagable with the collar member to selectively move the collar member in a substantially radial direction.

32. A device as claimed in claim 31 wherein the housing includes a third wedge surface and the collar member includes a fourth wedge surface, and the third wedge surface of the housing is engagable with the fourth wedge surface of the collar member to selectively move the collar member in a substantially radial direction.

33. A device as claimed in claim 32 wherein the third wedge surface is slidably engagable with the fourth wedge surface.

34. A device as claimed in claim 23 wherein the collar member is radially compressible from an open configuration to the sealing configuration.

35. A device as claimed in claim 34 wherein the collar member is biased towards the open configuration.

36. A device as claimed in claim 23 wherein the second seal includes a sealing portion movable in a substantially radial direction relative to the housing between the open configuration and the sealing configuration.

37. A device as claimed in claim 36 wherein the collar member extends longitudinally along the sealing portion.

38. A device as claimed in claim 36 wherein the longitudinal length of the sealing portion is at least 6 mm.

39. A device as claimed in claim 38 wherein the longitudinal length of the sealing portion is approximately 9 mm.

40. A device as claimed in claim 23 wherein the second seal comprises at least one anchor portion, the radial position of which is fixed relative to the main body portion.

41. A device as claimed in claim 40 wherein the at least one anchor portion is provided at an end of the second seal.

42. A device as claimed in claim 23 wherein the second seal is biased towards the open configuration.

43. A device as claimed in claim 42 wherein the second seal is composed of a resilient material.

44. A device as claimed in claim 42 wherein the second seal is composed of an elastomeric material.

45. A device as claimed in claim 23 wherein the second seal is a high pressure seal.

46. A device as claimed in claim 23 wherein the device comprises a main body portion defining a lumen, the housing being mateable with the main body portion with the lumen of the housing aligned with the lumen of the main body portion.

47. A device as claimed in claim 46 wherein the housing and the main body portion comprise corresponding alignment parts for alignment of the housing relative to the main body portion upon mating.

48. A device as claimed in claim 1 further comprising a gripping element to facilitate gripping of the device by a user; the gripping element including a first finger grip configured to be engaged by a first finger of the user, and a second finger grip configured to be engaged by a second finger of the user.

49. A device as claimed in claim 48 further comprising a side port in communication with the lumen.

50. A homeostasis device comprising:
a housing defining a lumen extending therethrough;
a first seal having a closed configuration to seal across the lumen, and an open configuration to facilitate passage of a medical device through the lumen;
a second seal having an open configuration to facilitate passage of the medical device through the lumen, and a sealing configuration to seal around the medical device passing through the lumen;
a tubular member selectively moveable between a retracted configuration and an inserted configuration, the tubular member extending through both the first seal and the second seal with a distal end of the tubular member extending distally of the second seal in the inserted configuration; and
a first guide path defined by a slot in a wall of the housing and a second guide path disposed radially inwardly of the wall of the housing, the tubular member including a guide element movable along the first guide path upon movement of the tubular member from the retracted configuration to the inserted configuration, and movable along the second guide path upon movement of the tubular member from the inserted configuration to the retracted configuration.

51. A device as claimed in claim 50 wherein the guide element is deflectable from the first guide path to the second guide path upon movement of the tubular member for the inserted configuration to the retracted configuration.

52. A device as claimed in claim 50 wherein a distal end of the guide element is fixed to the tubular member, the guide element extending longitudinally proximally.

53. A device as claimed in claim 52 wherein a proximal portion of the guide element engages a stop in the first guide path when the tubular member is in the inserted configuration.

54. A device as claimed in claim 50 wherein the first seal is biased towards the closed configuration.

55. A device as claimed in claim 50 further comprising a collar selectively moveable in a substantially radial direction for movement of the second seal between the open configuration and the sealing configuration.

56. A device as claimed in claim 55 wherein the device comprises an actuator member engagable with the collar member to selectively move the collar member in the substantially radial direction.

57. A device as claimed in claim 56 wherein the actuator member is disposed around a circumference of the device.

58. A device as claimed in claim 55 wherein second seal includes a sealing portion and at least one terminal anchor portion, the collar member selectively moving the sealing portion relative to the at least one terminal anchor portion.

59. A device as claimed in claim 58 wherein the sealing portion of the second seal is deformable when collar member compresses the sealing portion in the radial direction to constrict a lumen of the second seal.

60. A device as claimed in claim 50 wherein the second seal is biased towards the open configuration.

61. A homeostasis device comprising:
a housing defining a lumen extending therethrough;
a main body portion defining a lumen longitudinally therein, the main body portion being mateable with the housing such that the lumen of the main body portion is aligned with the lumen of the housing;
a first seal biased in a closed configuration to seal across the lumen of the housing;
a second seal having an open configuration to facilitate passage of the medical device through the lumen of the main body portion and a sealing configuration to seal around the medical device passing through the lumen of the main body portion;
a tubular member selectively moveable between a retracted configuration and an inserted configuration for movement of the first seal from the closed configuration to an open configuration, the tubular member extending through both the first seal and the second seal with a distal end of the tubular member extending distally of the second seal in the inserted configuration; and an actuator member disposed around a circumference of the device, the actuator member operating independent of the tubular member to selectively move the second seal between the open configuration and the sealing configuration.

62. A device as claimed in claim 61 wherein the tubular member includes a guide element movable along a first guide path upon movement of the tubular member from the retracted configuration to the inserted configuration, the guide element deflecting from the first guide path to a second guide path and moving along the second guide path upon movement of the tubular member from the inserted configuration to the retracted configuration.

63. A device as claimed in claim 62 wherein a proximal end of the guide element engages a stop in the first guide path when the tubular member is in the inserted configuration.

64. A device as claimed in claim 61 wherein the actuator member selectively moves the second seal into the sealing configuration when the tubular member is in the retracted configuration.

* * * * *